US010946087B2

(12) United States Patent
Tornieporth et al.

(10) Patent No.: US 10,946,087 B2
(45) **Date of Patent: *Mar. 16, 2021**

(54) VACCINE COMPOSITIONS AGAINST DENGUE VIRUS DISEASES

(71) Applicant: Sanofi Pasteur, Lyons (FR)

(72) Inventors: Nadia Tornieporth, Wedemark (DE); Alain Bouckenooghe, Singapore (SG); Fernando Noriega, Cresco, PA (US); Melanie Saville, Saint Didier au Mont d'Or (FR); Nicholas Jackson, Francheville (FR); Yves Girerd-Chambaz, Messimy (FR)

(73) Assignee: SANOFI PASTEUR, Lyons (FR)

(*) Notice: Subject to any disclaimer, the term of this patent is extended or adjusted under 35 U.S.C. 154(b) by 0 days.

This patent is subject to a terminal disclaimer.

(21) Appl. No.: 15/507,952

(22) PCT Filed: Sep. 2, 2015

(86) PCT No.: PCT/EP2015/070060

§ 371 (c)(1),
(2) Date: Mar. 1, 2017

(87) PCT Pub. No.: WO2016/034629

PCT Pub. Date: Mar. 10, 2016

(65) Prior Publication Data

US 2017/0304426 A1 Oct. 26, 2017

(30) Foreign Application Priority Data

Sep. 2, 2014 (EP) .................................... 14306350
Jun. 4, 2015 (EP) .................................... 15305851

(51) Int. Cl.

*A61K 39/12* (2006.01)
*A61K 39/295* (2006.01)
*C12N 7/00* (2006.01)
*A61K 39/00* (2006.01)

(52) U.S. Cl.

CPC ................ *A61K 39/12* (2013.01); *C12N 7/00* (2013.01); *A61K 2039/5252* (2013.01); *A61K 2039/5254* (2013.01); *A61K 2039/5256* (2013.01); *A61K 2039/5258* (2013.01); *C12N 2770/24123* (2013.01); *C12N 2770/24134* (2013.01); *C12N 2770/24144* (2013.01); *Y02A 50/30* (2018.01)

(58) Field of Classification Search

CPC .................. A61K 39/12; A61K 39/295; A61K 2039/5252; A61K 2039/5254; A61K 2039/5256; A61K 2039/5258; A61K 2039/70; C12N 7/00; C12N 2770/24123; C12N 2770/24134; C12N 2770/24144; Y02A 50/386; Y02A 50/388; A61P 37/04; A61P 31/14

See application file for complete search history.

(56) References Cited

U.S. PATENT DOCUMENTS

| | | | | |
|---|---|---|---|---|
| 6,696,281 | B1 | 2/2004 | Chambers et al. | |
| 6,962,708 | B1 | 11/2005 | Chambers et al. | |
| 7,459,160 | B2 | 10/2008 | Monath et al. | |
| 7,641,907 | B2 | 1/2010 | Kinney et al. | |
| 7,641,908 | B2 | 1/2010 | Kinney et al. | |
| 7,718,357 | B2 * | 5/2010 | Guy | A61K 39/12 424/201.1 |
| 7,718,358 | B2 * | 5/2010 | Guy | A61K 39/12 424/201.1 |
| 7,718,359 | B2 * | 5/2010 | Guy | A61K 39/12 424/218.1 |
| 7,968,102 | B2 | 6/2011 | Quentin-Millet | |
| 8,067,565 | B2 | 11/2011 | Kinney et al. | |
| 8,067,566 | B2 | 11/2011 | Kinney et al. | |
| 8,142,795 | B2 | 3/2012 | Francon et al. | |
| 8,227,587 | B2 | 7/2012 | Quentin-Millet | |
| 8,697,353 | B2 | 4/2014 | BouckenooQhe et al. | |
| 8,795,688 | B2 | 8/2014 | Kinney et al. | |
| 8,852,914 | B2 | 10/2014 | Monath et al. | |
| 9,169,298 | B2 | 10/2015 | Kinney et al. | |
| 2004/0259224 | A1 | 12/2004 | Guirakhoo | |
| 2005/0002968 | A1 | 1/2005 | Monath et al. | |
| 2006/0062803 | A1 | 3/2006 | Kinney et al. | |
| 2006/0292172 | A1 | 12/2006 | Kinney et al. | |
| 2008/0014219 | A1 | 1/2008 | Barban et al. | |
| 2008/0085288 | A1 | 4/2008 | Guy et al. | |
| 2008/0131460 | A1 | 6/2008 | Guy et al. | |
| 2009/0169581 | A1 | 7/2009 | Sandrine | |
| 2009/0191240 | A1 | 7/2009 | Monath et al. | |
| 2010/0015180 | A1 | 1/2010 | Francon et al. | |
| 2010/0158938 | A1 | 6/2010 | Guirakhoo | |
| 2010/0215692 | A1 | 8/2010 | Quentin-Millet | |

(Continued)

FOREIGN PATENT DOCUMENTS

| | | | |
|---|---|---|---|
| EP | 1958959 | A2 | 8/2008 |
| WO | WO 1998/037911 | A1 | 9/1998 |

(Continued)

OTHER PUBLICATIONS

Capeding MR, et. al. Lancet. Oct. 11, 2014;384(9951):1358-65. doi: 10.1016/S0140-6736(14)61060-6. Epub Jul. 10, 2014.*

(Continued)

*Primary Examiner* — Rachel B Gill
(74) *Attorney, Agent, or Firm* — McNeill Baur PLLC

(57) ABSTRACT

The present invention relates to vaccine compositions that are useful in a method of protecting a human subject against dengue disease.

27 Claims, 2 Drawing Sheets

Specification includes a Sequence Listing.

(56) References Cited

U.S. PATENT DOCUMENTS

2010/0221285 A1 9/2010 Barban et al.
2010/0239612 A1 9/2010 Guy et al.
2010/0255028 A1 10/2010 Delaqrave et al.
2010/0270202 A1* 10/2010 Guy ........................ A61K 39/12 206/570
2011/0014229 A1 1/2011 Kleanthous et al.
2011/0150771 A1 6/2011 Kinney et al.
2011/0189226 A1 8/2011 Bouckenooghe et al.
2011/0206730 A1 8/2011 Quentin-Millet
2012/0083584 A1 4/2012 Kinney et al.
2012/0083585 A1 4/2012 Kinney et al.
2013/0028934 A1 1/2013 Francon et al.
2013/0095136 A1 4/2013 Guirakhoo
2013/0149338 A1* 6/2013 Stinchcomb ........... A61K 39/12 424/218.1
2014/0220073 A1 8/2014 Bouckenooahe et al.
2015/0024004 A1 1/2015 Monath et al.
2015/0031857 A1 1/2015 Kinney et al.
2015/0196631 A1 7/2015 Bouckenooghe et al.
2015/0265695 A1 9/2015 Yao et al.
2017/0304426 A1 10/2017 Tornieporth et al.

FOREIGN PATENT DOCUMENTS

WO WO 2001/039802 A1 6/2001
WO WO 2002/081754 A1 10/2002
WO WO 2008/047023 A2 4/2008
WO WO 2011/013097 A2 2/2011
WO WO 2011/146933 A2 11/2011
WO WO 2012/051491 A1 4/2012
WO WO 2014/016360 A1 1/2014
WO WO 2014/016362 A1 1/2014
WO WO-2017005654 A1 * 1/2017 ......... A61K 39/0018

OTHER PUBLICATIONS

Houlton S. "Sanofi ordered to pull dengue vaccine." Chemistry World. Dec. 15, 2017. https://www.chemistryworld.com/news/sanofi-ordered-to-pull-dengue-vaccine/3008436.article.*

Roehrig JT. Current status of dengue vaccine development. SAGE/Immunization Meeting, Apr. 2013.*

ClinicalTrials.gov Identifier: NCT01187433. Study of CYD Dengue Vaccine in Healthy Children and Adolescents in South America. First Posted: Aug. 24, 2010, Study record updated Feb. 5, 2013.*

World Health Organization (WHO). Guidelines on the Quality, Safety and Efficacy of Dengue Tetravalent Vaccines (Live, Attenuated). Proposed replacement of TRS 932, Annex 1. May 1, 2011. WHO Press, Geneva, Switzerland.*

Lanata CF, Andrade T, Gil Al, Terrones C, Valladolid O, Zambrano B, Saville M, Crevat D. Immunogenicity and safety of tetravalent dengue vaccine in 2-11 year-olds previously vaccinated against yellow fever: randomized, controlled, phase II study in Piura, Peru. Vaccine. Sep. 7, 2012;30(41):5935-41. Epub Jul. 3, 2012.*

Shang W, Liu J, Yang J, Hu Z, Rao X. Dengue virus-like particles: construction and application. Appl Microbiol Biotechnol. Apr. 2012;94(1):39-46. Epub Mar. 1, 2012.*

Durbin AP, Kirkpatrick BD, Pierce KK, Elwood D, et. al. A single dose of any of four different live attenuated tetravalent dengue vaccines is safe and immunogenic in flavivirus-naive adults: a randomized, double-blind clinical trial. J Infect Dis. Mar. 15, 2013;207(6):957-65. Epub Jan. 17, 2013.*

George SL. Prospects for a dengue vaccine: progress and pitfalls. Mo Med. Jul.-Aug. 2014;111(4):337-42.*

Guirakhoo F, Pugachev K, Zhang Z, Myers G, Levenbook I, Draper K, Lang J, Ocran S, Mitchell F, Parsons M, Brown N, Brandler S , Fournier C, Barrere B, Rizvi F, et. al. Safety and efficacy of chimeric yellow Fever-dengue virus tetravalent vaccine formulations in nonhuman primates. J Virol. May 2004;78(9):4761-75.*

Durbin AP, Whitehead SS. Next-generation dengue vaccines: novel strategies currently under development. Viruses. Oct. 2011;3(10):1800-14. Epub Sep. 26, 2011.*

Poo J, Galan F, Forrat R, Zambrano B, Lang J, Dayan G. Live-attenuated Tetravalent Dengue Vaccine in Dengue-naïve Children, Adolescents, and Adults in Mexico City: Randomized Controlled Phase 1 Trial of Safety and Immunogenicity. Pediatr Infect Dis J. Jan. 2011;30(1):e9-17. (Year: 2011).*

Blaney et. al. (Blaney JE Jr, Matro JM, Murphy BR, Whitehead SS. Recombinant, live-attenuated tetravalent dengue virus vaccine formulations induce a balanced, broad, and protective neutralizing antibody response against each of the four serotypes in rhesus monkeys. J Virol. May 2005;79(9):5516-28. (Year: 2005).*

Capeding RZ, Luna IA, Bomasang E, Lupisan S, Lang J, Forrat R, Wartel A, Crevat D. Live-attenuated, tetravalent dengue vaccine in children, adolescents and adults in a dengue endemic country: randomized controlled phase I trial in the Philippines. Vaccine. May 17, 2011;29(22):3863-72. Epub Apr. 6, 2011. (Year: 2011).*

Guy B. Immunogenicity of sanofi pasteur tetravalent dengue vaccine. J Clin Virol. Oct. 2009; 46 Suppl 2:S16-9.*

Simmons M, Burgess T, Lynch J, Putnak R. Protection against dengue virus by non-replicating and live attenuated vaccines used together in a prime boost vaccination strategy. Virology. Jan. 2, 2010;396(2):280-8. Epub Nov. 1, 2009.*

Asher Mullard, Nature Reviews, Drug Discovery, Nov. 2014, 13:801-802.

Bhamarapravati et al. "Live attenuated tetravalent dengue vaccine" *Vaccine*, 18: 44-47 (2000).

Capeding et al., "Clinical efficacy and safety of a novel tetravalent dengue vaccine in healthy children in Asia: a phase 3, randomised, observer-masked, placebo-controlled trial," Lancet. 384(9951):1358-65 (2014) (8 pages).

Capeding et al., "Live-attenuated, tetravalent dengue vaccine in children, adolescents and adults in a dengue endemic country: randomized controlled phase I trial in the Philippines." Vaccine 29(22):3863-72 (2011).

Clements et al. "Development of a recombinant tetravalent dengue virus vaccine: Immunogenicity and efficacy studies in mice and monkeys" *Vaccine*, 28(15): 2705-2715 (2010).

ClinicalTrials.gov "Efficacy and safety of dengue in healthy children," <https://clinicaltrials.qov/ct2/show/NCT00842530>, updated Sep. 18, 2014 (6 paqes).

Deauvieau et al., "Innate immune responses in human dendritic cells upon infection by chimeric yellow-fever dengue vaccine serotypes 1-4," Am J Trop Med Hyq. 76(1): 144-54 (2007).

Dorigatti et al., "Refining the Characterisation of the Sanofi Pasteur Dengue Vaccine's Efficacy Profile Using Machine Learning," Epidemics6—International Conference on Infectious Disease Dynamics, Sitges, Spain, pp. 1-15 (Nov. 29, 2017-Dec. 1, 2017).

Endy, "Dengue Human Infection Model Performance Parameters" The Journal of Infectious Diseases, S56-S60 (2014).

Guy et al. "Development of Sanofi Pasteur tetravalent dengue vaccine" *Hum Vaccin*. 6(9): 696-705 (2010).

Guy et al., "Cell-mediated immunity induces by chimeric tetravalent dengue vaccine in native or flavivirus-primed subjects." Vaccine. 26(45):5712-21 (2008).

Guy et al., "From research to phase III: vaccine, preclinical, industrial and clinical development of the Sanofi Pasteur tetravalent dengue vaccine.", Vaccine 29(42):7229-41 (2011).

Hadinegoro et al., "Efficacy and Long-Term Safety of a Dengue Vaccine in Regions of Endemic Disease." N Engl J Med 373(13): 1195-206 (2015), Supplementary Appendix (28 pages), and Protocol (917 pages).

International Search Report and Written Opinion for PCT/EP2013/065669, dated Dec. 18, 2013 (24 pages).

International Search Report and Written Opinion for PCT/EP2013/065667, dated Oct. 4, 2013 (12 pages).

International Search Report for PCT/EP2015/070060, dated Mar. 10, 2016, 6 pages.

Lang, Diseases, "Dengue vaccine late stage development update," International Journal of Infectious Diseases, $15^{th}$ ICID Abstracts 165:e5 (2012) (1 page).

Morrison et al., "A novel tetravalent dengue vaccine is well tolerated and immunogenic against all 4 serotypes in flavivirus-naive adults," J dengue Dis. 201(3): 370-7 (2010).

(56) References Cited

OTHER PUBLICATIONS

NCBI Blast for Accession No. AAA73186.1, dated Aug. 2, 1993, retrieved on Oct. 5, 2017 (4 pages).
NCBI Blast for Accession No. ACA58343.1, dated May 21, 2009, retrieved on Oct. 5, 2017 (4 pages).
NCBI Blast for Accession No. AEN71248.1, dated Sep. 4, 2011, retrieved on May 7, 2016 (2 pages).
NCBI Blast for Accession No. CAR65175.2, dated Sep. 13, 2008, retrieved on Oct. 5, 2017 (4 pages).
Office Action form U.S. Appl. No. 14/416,496, dated Apr. 12, 2017.
Office Action form U.S. Appl. No. 14/416,496, dated Sep. 16, 2016.
Osorio et al. "Development of DENVax: A chimeric dengue-2 PDK-53-based tetravalent vaccine for prote for Osorio et protection al. ction against dengue fever" *Vaccine*, 29(42): 7251-7260 (2011).
Poo et al., "Live-attenuated Tetravalent Dengue Vaccine in Dengue-naive Children, Adolescents, and Adults in Mexico City: Randomized Controlled Phase 1 Trial of Safety and Immunogenicity," Pediatr Infect Dis J. 30(1):e9-17 (2011) (9 pages).
Rabaa et al., "Genetic epidemiology of dengue viruses in phase III trials for the CYD tetravalent dengue vaccine and implications for efficacy." eLife 6:e24196 (22 pages) (2017).
Sabchareon et al., "Protective efficacy of the recombinant, live-attenuated, CYD tetravalent dengue vaccine in Thai schoolchildren: a randomized, controlled phase 2b trial." Lancet 380(9853) 1559-67 (2012).
Sanofi Press Release "Sanofi updates information on dengue vaccine" pp. 1-3, Nov. 29, 2017.
Twiddy et al., "Phylogenetic relationships and differential selection pressures among genotypes of dengue-2 virus." Vaccines, Virology, 298(1):63-72 (2002).
Villar et al. "Efficacy of a tetravalent dengue vaccine in children in Latin America." N Engl J Med. 372(2): 113-23 (2015) (11 pages) and Supplemental Appendix (62 pages).
World Dengue Health Organization, Immunization, Vaccines and Biologicals: Questions and Answers on Dengue Vaccines, http://www.who.int/immunization/research/development/dengue_q_and_a/en/>, retrieved Oct. 9, 2017 (3 pages).
Zhang et al. "Vaccination with dengue virus-like particles induces humoral and cellular immune responses in mice" *Virology Journal*, 8(1): 333. Abstract XP021103960 (2011).
Del Angel et al. "Dengue Vaccines: Strong Sought but Not a Reality Just Yet" PLOS 9(10): e1003551 (2013).
Moodie et al. "Neutralizing Antibody Correlates Analysis of Tetravalent Dengue Vaccine Efficacy Trials in Asia and Latin America," The Journal of Infectious Diseases (2018) 217: 742-753.
File history of U.S. Appl. No. 14/416,492, filed Jan. 22, 2015, published as 2015/0265695 on Sep. 24, 2015.
File history of U.S. Appl. No. 14/416,496, filed Jan. 22, 2015, published as 2015/0196631 on Jul. 16, 2015.
File history of U.S. Appl. No. 13/698,719, filed Nov. 19, 2012, published as 2013/0071419 on Mar. 21, 2013, issued as U.S. Pat. No. 8,993,744 on Mar. 31, 2015.
File history of U.S. Appl. No. 15/740,889, filed Dec. 29, 2017, related to PCT Application No. WO2017/005652 published Jan. 12, 2017.
File history of U.S. Appl. No. 11/944,311, filed Nov. 21, 2007, published as 2008/0131460 on Jun. 5, 2008, issued as U.S. Pat. No. 7,718,359 on May 18, 2010.
Qiao et al. "Priming Effect of Dengue and Yellow Fever Vaccination on the Immunogenicity, Infectivity, and Safety of a Tetravalent Dengue Vaccine in Humans," The American Journal of Tropical Medicine and Hygiene, 85(4): 724-731 (2011).
Endy, Timothy P., "Dengue Human Infection Model Performance Parameters", JID 209 (Suppl. 2): S56-S60 (2014).
The American Journal of Topical Medicine and Hygiene, vol. 81, No. 5, Suppl. 1, pp. 113 (2009).
Okowski et al., "Reduced Risk of Disease During Postsecondary Dengue Virus Infections", The Journal of Infectious Diseases, 208, pp. 1026-1033 (Sep. 15, 2013).
Final Office Action in corresponding U.S. Appl. No. 16/123,319, dated Jun. 17, 2020 (14 pages).
Anderson et al., "Interference and Facilitation Between Dengue Serotypes in a Tetravalent Live Dengue Virus Vaccine Candidate," Journal of Infectious Diseases, 204(3), pp. 442-450 (Aug. 1, 2011).
Arredondo-Garcia et al., "Four-year safety follow-up of the tetravalent dengue vaccine efficacy randomized controlled trials in Asia and Latin America", Clinical Microbiology & Infection, vol. 24(7), p. 755-763 (2018).
Carpp et al., "Microneutralization assay titer correlates analysis in two Phase 3 trials of the CYD-TDV tetravalent lengue vaccine in Asia and Latin America", PLoS One, 15(6) (Jun. 15, 2020).
Coudeville et al., "Potential impact of dengue vaccination: Insights from two large-scale phase III trials with a tetravalent dengue vaccine." Vaccine, 34(50):6426-6435 (2016).
Crevat et al., "Safety and immunogeneicity of a tetravalent dengue vaccine in flavivirus-naive and -immune pediatric populations with two vaccination regimens", The American Journal of Topical Medicine and Hygiene, 81(5), Suppl. 1, p. 113, Abstract 395 (2009).
Da Costa et al., "Safety, immunogenicity and efficacy of a recombinant tetravalent dengue vaccine: A meta-analysis of randomized trials", Vaccine, vol. 32(39), pp. 4885-4892 (2014).
Dayan et al., "Assessment of the long-term efficacy of a dengue vaccine against symptomatic, virologically-confirmed dengue disease by baseline dengue serostatus", Vaccine, 38(19), pp. 3531-3536 (Apr. 23, 2020).
Diazgrandos et al., "CYD-TDV dengue vaccine performance by baseline immune profile (monotypic/multitypic) in dengue seropositive individuals", Clinical Infectious Diseases 2020:XX, pp. 1-8 (Mar. 21, 2020).
English translation of Official Action in Japanese Patent Application No. 2017-511914, dated Mar. 3, 2020 (2 pages).
Gailhardou et al., "Safety Overview of a Recombinant Live-Attenuated Tetravalent Dengue Vaccine: Pooled Analysis of Data from 18 Clinical Trials", PLoS Negl Trop Dis., 10(7):e0004821 (Jul. 14, 2016).
Gilbert et al. "Bridging Efficacy of a Tetravalent Dengue Vaccine from Children/Adolescents to Adults in Highly Endemic Countries Based on Neutralizing Antibody Response" American Journal of Tropical Medicine and Hygiene, 101(1), pp. 164-179 (May 20, 2019).
Guy et al., "A recombinant live attenuated tetravalent vaccine for the prevention of dengue", Expert Rev Vaccines;16 (7)1-13 (Jul. 2017).
Guy et al., "Dengue vaccine: hypotheses to understand CYD-TDV-induced protection", Nat Rev Microbio., 14(1):45-54 (Jan. 2016).
Guy et al., "Immunogenicity of Sanofi Pasteur tetravalent dengue vaccine", Journal of Clinical Virology, vol. 46, pp. S16-S19 (Oct. 1, 2009).
Guy et al., "When Can One Vaccinate with a Live Vaccine after Wild-Type Dengue Infection?", Vaccines, 8(2), p. 174 (Apr. 9, 2020).
Kirstein et al., "Immunogenicity of the CYD tetravalent dengue vaccine using an accelerated schedule: randomised phase II study in US adults", BMC Infection Diseases,18(475) 11 pages (Sep. 21, 2018).
Limkittikul et al., "Long-term safety follow-up of children from a randomized controlled phase llb proof of concept efficacy study of the live attenuated tetravalent dengue vaccine (CYD-TDV) in Thailand", Asian Pacific Journal of Tropical Medicine 2019; 12(9), p. 396-403 (Sep. 30, 2019).
Olivera-Botello et al., "CYD-TDV Vaccine Trial Group. Tetravalent Dengue Vaccine Reduces Symptomatic and Asymptomatic Dengue Virus Infections in Healthy Children and Adolescents Aged 2-16 Years in Asia and Latin America", J Infect Dis., 214(7):994-1000 (Oct. 1, 2016).
Park, et al., "Immunogenicity and safety of a dengue vaccine given as a booster in Singapore: a randomized Phase II, placebo-controlled trial evaluating its effects 5-6 years after completion of the primary series", Human Vaccines & Immunotherapeutics, 16(3), 523-529 (2019).

(56) References Cited

OTHER PUBLICATIONS

Reynales et al.,"Secondary Analysis of the Efficacy and Safety Trial Data of the Tetravalent Dengue Vaccine in children and Adolescents in Colombia", The Pediatric Infectious Disease Journal, 39(4), pp. e30-e36 (Apr. 2020).
Sridhar et al., "Effect of Dengue Serostatus on Dengue Vaccine Safety and Efficacy", New England Journal of Medicine, 379(4), pp. 327-340 (Jul. 26, 2018).
Study of a Novel Tetravalent Dengue Vaccine in Healthy Children Aged 2 to 14 Years in Asia; ClinicalTrials.gov identifier: NCT01373281; see Study Details, Tabular View & Study Results (Dec. 17, 2018) (14 pages).
Study of a Novel Tetravalent Dengue Vaccine in Healthy Children and Adolescents Aged 9 to 16 Years in Latin America; ClinicalTrials.gov identifier: NCT01374516; see Study Details, Tabular View & Study Results (Apr. 17, 2019) (14 pages).
Tran et al., "Long-term immunogenicity and safety of tetravalent dengue vaccine (CYD-TDV) in healthy populations in Singapore and Vietnam: 4-year follow-up of randomized, controlled, phase II trials"; Human Vaccines & Immunotherapeutics; vol. 15(10), pp. 2315-2327 (2019).
Vigne et al., "Integrated immunogenicity analysis of a tetravalent dengue vaccine up to 4 y after vaccination", Hum Vaccin Immunother,13(9):2004-2016 (Sep. 2, 2017).
Final Office Action in related U.S. Appl. No. 16/123,319, dated Jun. 17, 2020 (14 pages).
Dayan et al., "Efficacy after 1 and 2 doses of CYD-TDV in dengue endemic areas by dengue serostatus", Vaccine 38, pp. 6472-6477 (Aug. 6, 2020).
Coronel et al., Poster LB5345, American Society of Tropical Medicine and Hygiene (ASTMH) Conference, (Nov. 20-24, 2019).

* cited by examiner

Number at Risk

| | | | | | | | |
|---|---|---|---|---|---|---|---|
| 1 | 13914 | 13829 | 13516 | 13298 | 13133 | 805 | 0 |
| 2 | 6940 | 6860 | 6672 | 6498 | 6363 | 373 | 0 |

SEQUENCE LISTING

```
<160> NUMBER OF SEQ ID NOS: 7

<210> SEQ ID NO 1
<211> LENGTH: 1983
<212> TYPE: RNA
<213> ORGANISM: Artificial Sequence
<220> FEATURE:
<223> OTHER INFORMATION: CYD1 prME

<400> SEQUENCE: 1

uuucaucuga ccacacgagg gggagagccg cauaugauag uuaccaagca ggaaagagga      60

aagucacuuu uguuuaagac cucagcuggu gucaacaugu gcacccuuau ugcgauggau     120

uugggagagu uaugugagga uacaaugacu uacaaauguc cucgaaucac ugaggcggaa     180

ccagaugacg uugauuguug gugcaaugcc acagacacau gggugaccua uggaacgugu     240

ucccaaacug gcgagcaccg acgagacaaa cguuccgucg cacuggcccc acacguggga     300

cuuggucuag aaacaagaac cgaaacgugg auguccucug aaggcgcuug gaaacaaaua     360

caaagagugg agacuugggc ccugagacac ccaggauuca cagugauagc ccuuuuucua     420

gcacaugcca uaggaacauc caucacccag aaagggauua uuuucauuuu guugaugcug     480

guaacaccau ccauggccau gcgaugugug ggaauaggca acagggacuu cguggaagga     540

cugucaggag caacgugggu agaugguua cuggaacaug gaaguugcgu caccaccaug     600

gcaaaagaua aaccaacauu ggacauugaa cucuugaaga cggaagucac aaacccugcc     660

guccuucgaa aacugugcau cgaagcuaaa auaucaaaca ccaccaccga uucaagaugc     720

ccaacacaag gagaagccac acugguggaa gagcaagacg cgaauuuugu gugucgacga     780

acguuugugg acagaggcug gggcaauggc uguggggcucu ucggaaaagg uagccuaaua     840

acgugugcua aguucaagug ugugacaaaa cuggaaggaa agauaguuca auaugaaaac     900

uugaaauauu caguaauagu caccguccac acuggagacc agcaccaggu gggaaaugaa     960

agcacagaac augggacaac agcaacuaua acaccucaag cucccacguc ggaaauacag    1020

cugaccgacu acggagcucu aacauuggau ugcucaccua gaacaggacu agacuucaau    1080

gaaaugggugu uguugacaau gaaagaaaga ucauggcuag uccacaaaca augguuucua    1140

gaccuaccac ugccuuggac cucgggagcu acaacgucac aagagacuug gaacagacaa    1200

gauuugcugg uaacauuuaa gacagcucau gcaaagaagc aggaaguagu cguacuagga    1260

ucacaagaag gagcaaugca cacugcguug accggagcga cagaaaucca aacgucugga    1320
```

-continued

```
acgacaacaa uuuuugcagg acacuugaaa uguagacuaa aaauggacaa acugacucua   1380

aaagggaugu cauaugugau gugcacaggc ucauucaagc uagagaaaga gguggcugag   1440

acccagcaug gaaccguucu agugcagguu aaauacgaag gaacagaugc accaugcaag   1500

aucccuuuuu cgacccaaga ugaaaaagga guaacccaga augggagagu gauaacagcc   1560

aacccuauag ucacugacaa ggaaaaacca gucaacauug aggcagaacc accuuuuggu   1620

gagaguuaca ucgugguagg agcaggugaa aaagcuuuga aacuaagcug guucaagaaa   1680

ggaagcacca uagggaaaau guuugaggca acugcccgag gagcacgaag gauggccaua   1740

cugggagaca ccgcauggga cuuugguucu auaggaggag uguucacauc uguuggaaaa   1800

cuaguacacc agauuuuugg aacugcauau ggaguuuugu ucagcggugu uuccuggacc   1860

augaaaauag gaauaggggu ucugcugaca uggcuaggau uaaacucaag gagcacgucc   1920

cuuucgauga cgugcauugc aguuggccug guaacacugu accuaggagu caugguuggc   1980

gcc                                                                 1983
```

<210> SEQ ID NO 2
<211> LENGTH: 1983
<212> TYPE: RNA
<213> ORGANISM: Artificial Sequence
<220> FEATURE:
<223> OTHER INFORMATION: CYD2 prME

<400> SEQUENCE: 2

```
uuccaucuaa ccacacguaa cggagaacca cacaugaucg ucaguagaca agagaaaggg     60

aaaagucuug uguuuaaaac agaggauggc gugaacaugu gcacccucau ggccauggac    120

cuuggugaau ugugugaaga cacaaucacg uacaaguguc cccuucucag gcagaaugag    180

ccagaagaca uagacugcug gugcaacucc acguccacgu ggguaaccua ugggacuugu    240

accaccacgg gagaacauag aagagaaaaa agaucagugg cacucguucc acauguggga    300

augggacugg agacgcgaac ugaaacaugg augucaucag aaggggcuug gaaacaugcc    360

cagagaauug aaauuuggau ccugagacau ccaggcuuca ccauaauggc agcaauccug    420

gcauacacca uagggacgac acauuuccag agagcacuga uuuucaucuu acugacagcu    480

gucgcuccuu caaugacaau gcguugcaua ggaauaucaa auagagacuu uguagaaggg    540

guuucaggag gaagcugggu ugacauaguc uuagaacaug gaagcugugu gacgacgaug    600

gcaaaaaaca aaccaacauu ggauuuugaa cugauaaaaa cagaagccaa acagccugcc    660

acccuaagga aguacuguau agaggcaaag cuaaccaaca caacaacaga aucucguugc    720

ccaacacaag gggaacccag ccuaaaugaa gagcaggaua aaagguucgu cugcaaacac    780

uccaugguag acagaggaug ggaaaaugga uguggauuau uuggaaaggg aggcauugug    840

accugugcua uguucacaug caaaaagaac auggagggaa aaguugugca gccagaaaac    900

uuggaauaca ccauuguggu aacaccccac ucaggggaag agcaugcggu cggaaaugac    960

acaggaaaac auggcaagga aaucaaagua acaccacaga guuccaucac agaagcagaa   1020

uugacagguu auggcacugu cacgauggag ugcucuccga gaacaggccu cgacuucaau   1080

gagauggugu ugcugcagau ggaaaauaaa gcuuggcugg ugcauaggca augguuccua   1140

gaccugccgu uaccauggcu gcccggagcg gacacacaag ggucaaauug gauacaaaaa   1200

gaaacauugg ucacuuucaa aaauccucau gcgaagaaac aggauguuuu uguuuuagga   1260

ucccaagaag gggccaugca cacagcacuc acaggggcca cagaaaucca aaugucauca   1320

ggaaacuuac ucuucacagg acaucucaag ugcaggcuga gaauggacaa gcuacagcuc   1380
```

```
aaaggaaugu cauacucuau gugcacagga aaguuuaaag uugugaagga aauagcagaa   1440

acacaacaug gaacaauagu uaucagggug caguaugaag gggacggcuc uccauguaaa   1500

aucccuuuug agauaaugga uuuggaaaaa agacaugucu uaggucgccu gaucacaguc   1560

aacccaauug ugacagaaaa agauagccca gucaacauag aagcagaacc uccauucgga   1620

gacagcuaca ucaucauagg aguagagccg ggacaacuga agcucaacug guuuaagaaa   1680

ggaaguucua ucggccaaau guuugagaca acaaugaggg gggcgaagag aauggccauu   1740

uugggugaca cagccuggga uuuuggaucc cugggaggag uguuuacauc uauaggaaaa   1800

gcccuccacc aagucuuugg agcaaucuau ggagcugccu ucaguggggu cucauggacu   1860

augaaaaucc ucauaggagu cauuaucaca uggauaggaa ugaauucacg cagcaccuca   1920

cugucugugu cacuaguauu ggugggaguc gugacgcugu auuugggagu uaugguggc   1980

gcc                                                                 1983
```

```
<210> SEQ ID NO 3
<211> LENGTH: 1977
<212> TYPE: RNA
<213> ORGANISM: Artificial Sequence
<220> FEATURE:
<223> OTHER INFORMATION: CYD3 prME

<400> SEQUENCE: 3

uuccacuuaa cuucacgaga uggagagccg cgcaugauug uggggaagaa ugaaagaggg     60

aaaucccuac uuuuuaagac agcuucugga aucaacaugu gcacacucau agccauggac    120

uugggagaga ugugugauga cacggucacu uacaaaugcc cccucauugc cgaaguggaa    180

ccugaagaca uugacugcug gugcaaccuu acaucgacau gggugacuua uggaacgugc    240

aaucaagcug gggagcauag acgcgacaag agaucagugg cguuagcucc ccaugucggc    300

augggacugg acacacgcac ccaaaccugg augucggcug aaggagcuug gagacaaguc    360

gagaagguag agacaugggc ucuuaggcac ccaggguuca ccauacuagc ucuauuucuu    420

gcucauuaca uaggcacuuc ccugacccag aaaguggua uuuuuauacu acuaaugcug    480

gucacuccau ccauggcaau gagaugcgug ggaguaggaa acagagauuu uguggaaggu    540

cugucgggag cuacgugggu ugauguggug cuggagcacg gugggugugu gaccaccaug    600

gcuaagaaca agccuacgcu ggacauagag cuucagaaga ccgaggccac ccaacuggcg    660

acccuucgaa aguuaugcau ugagggaaaa auuaccaaca uaacaacuga cucaaggugu    720

ccuacccagg gggaagcgau uuuaccugag gagcaggacc agaacuacgu auguaagcac    780

acauaugugg auagaggcug ggaaacggu uguggguugu uuggaaaagg aagcuuggug    840

acaugcgcga aauuucaaug ucuagaauca auagagggaa aaguggugca acaugagaac    900

cucaaauaca cugucaucau uacagugcac acaggaaacc aacaccaggu gggaaaugac    960

acgcagggag ucacggcuga gauaacaccc caggcaucaa ccguugaagc caucuugccu   1020

gaauauggaa cccuugggcu agaaugcuca ccacggacag guuuggauuu caaugaaaug   1080

auuuuauuga caaugaaaaa caaagcaugg augguacaua ggcaaugguu cuuugaccua   1140

ccccuaccau ggacaucagg agcuacaaca gagacaccaa cuuggaacag gaaagagcuu   1200

cuugugacau ucaaaaaugc acaugcaaaa aagcaagaag uaguuguccu uggaucgcaa   1260

gagggagcaa ugcacacagc gcugacagga gcuacagaga uccaaaacuc aggagguaca   1320

agcauuuuug cggggcacuu gaaauguaga cuuaagaugg acaaauugga acucaagggg   1380
```

-continued

```
augagcuaug caaugugcuu gaauaccuuu guguugaaga aagaagucuc cgaaacgcag   1440

caugggacaa uacucauuaa gguugaguac aaaggggaag augcaccuug caagauuccu   1500

uucuccacag aggauggaca agggaaagcu cacaauggua gacugaucac agccaaccca   1560

guggugacca agaaggagga gccugucaac auugaggcug aaccuccuuu uggggaaagu   1620

aacauaguga uuggaauugg agacaaagcc uugaaaauua acugguacaa gaagggaagc   1680

ucgauuggga agauguucga ggccacugcc agaggugcaa ggcgcauggc caucuuggga   1740

gacacagccu gggacuuugg aucagugggu gguguucuaa auucauuagg gaaaauggug   1800

caccaaauau ucggaagugc uuacacagcc cuguuuagug gagucucaug gauaaugaaa   1860

auuggaauag guguccucuu aaccuggaua ggguugaauu caaaaaacac uuccauguca   1920

uuuucaugcg uugcgauagg aauuaucaca cucuaucugg gagccguggu acaggcc      1977
```

<210> SEQ ID NO 4
<211> LENGTH: 1983
<212> TYPE: RNA
<213> ORGANISM: Artificial Sequence
<220> FEATURE:
<223> OTHER INFORMATION: CYD4 prME

<400> SEQUENCE: 4

```
uuucaccugu caacaagaga cggcgaaccc cucaugauag uggcaaaaca cgaaaggggg     60

agaccucucu uguuuaagac aacagaggga aucaacaaau gcacucuuau ugccauggac    120

cugggugaaa ugugugaaga cacuguuacg uauaaaugcc cucuacuggu uaacaccgaa    180

ccugaagaca uugauugcug gugcaaucuc acguccaccu gggucaugua cgggacaugu    240

acccagagcg gagaacggag acgagagaag cgcucaguag cuuuaacacc acauucagga    300

augggauugg aaacaagagc ugagacaugg augucaucgg aaggggcuug gaaacaugcu    360

caaagaguag aaagcuggau acucagaaac ccaggauucg cgcucuuggc aggauuuaug    420

gcuuacauga uugggcaaac aggaauucag cgaacugucu ucuuuguccu aaugaugcug    480

gucgccccau ccuacggaau gcgaugcgua ggaguaggga acagagacuu uguggaagga    540

gucucgggug gagcaugggu cgaccuggug cuggaacaug gaggaugcgu cacaaccaug    600

gcccagggaa aaccaaccuu ggauuuugaa cugaccaaga caacagccaa ggaaguggcu    660

cuacuucgaa ccuauugcau ugaagccucg auaucaaaca uaaccacggc aacaagaugu    720

ccaacgcaag gagagccuua ucucaaagag gaacaagacc aacaguacau uugccggaga    780

gaugugguag acagagggug gggcaauggc uguggcuuau uuggaaaagg aggaguugug    840

acaugugcga aguuuuuaug cucggggaag auaacaggca aucuggucca aauugaaaac    900

cuugaauaua cagugguugu gacaguccac aauggagaca cccaugcagu aggaaaugac    960

acaucuaauc auggagugac agccacgaua acucccaggu caccaucggu agaaguuaaa   1020

uugccggacu auggagaacu aacacucgau ugugaaccca gguccggaau ugauuucaau   1080

gagaugauuc ugaugaaaau gaaaaagaaa acguggcuug ugcauaagca augguuuuug   1140

gaccuaccuc uaccauggac agcaggagca gacacaucag aaguccauug gaauuacaaa   1200

gagagaaugg ugacauucaa gguuccucau gccaagagac aggaugugac agugcuagga   1260

ucucaggagg gagcuaugca uucugcccuc gccggagcca cagaagugga uuccggugau   1320

ggaaaucaca uguuugcagg acaucucaag ugcaaagucc guauggagaa auugagaauu   1380

aaaggaaugu cauacacaau guguucagga aaguucucaa uugacaaaga gauggcagaa   1440

acacagcaug ggacaacagu ggugaaaguc aaguaugaag gcgcuggagc uccguguaaa   1500
```

-continued

```
guccccauag agauaagaga ugugaacaag gaaaaagugg uugggcgcau caucucaucu   1560

accccuuuug cugagaauac caacagcgua accaacauag aauuagaacc cccuuuuggg   1620

gacaguuaca uagugauagg uguuggagau agugcauuaa cacuccauug guucaggaaa   1680

gggagcucca uuggcaagau guuugagucc acauacagag gugcaaaacg aauggccauu   1740

cuaggugaaa cagcuuggga uuuugguucu guugguggaa uguucacauc acugggaaag   1800

gcuguacacc agguuuuugg aagugugugau acaaccaugu uuggaggggu cucauggaug   1860

guuagaaucc uaauugggguu cuuaguauug uggauuggca cgaauucaag aaacacuuca   1920

auggcaauga cgugcauagc uguuggagga aucacucugu uucuagguuu cacaguuggc   1980

gcc                                                                 1983
```

```
<210> SEQ ID NO 5
<211> LENGTH: 1983
<212> TYPE: RNA
<213> ORGANISM: Artificial Sequence
<220> FEATURE:
<223> OTHER INFORMATION: CYD2V prME

<400> SEQUENCE: 5

uuccauuuaa ccacacgaaa uggagaacca cacaugaucg uuggcagaca agagaaaggg     60

aaaagccuuc uguuuaaaac agaggauggu gugaacaugu guacccucau ggccauugau    120

cuuggugaau ugugugaaga uacaaucacg uacaagugcc cccuccucag gcagaaugaa    180

ccagaagaua uagauuguug gugcaacucc acguccacau ggguaacuua ugggacgugu    240

accaccacag gagaacacag aagagaaaaa agaucagugg cacucguucc acaugugggu    300

augggacugg agacacgaac ugaaacaugg augucgucag aaggggccug gaaacacgcu    360

cagagaauug aaacuuggau cuugagacau ccaggcuuua ccauaauggc agcaauccug    420

gcauauaccg uaggaacgac acauuuccaa agggcccuga uuuucaucuu acuggcagcu    480

gucgcuccuu caaugacaau gcguugcaua ggaauaucaa auagagacuu uguagaaggg    540

guuucaggag gaagcugggu ugacauaguc uuagaacaug gaaguugugu gacgacaaug    600

gcaaaaaaua aaccaacacu ggauuuugaa cugauaaaaa cagaagccaa acaaccugcc    660

acucuaagga aguacuguau agaggcaaag cugaccaaua caacaacaga aucucguugc    720

ccaacacaag gggaacccag ucuaaaugaa gagcaggaca aaagguucgu cugcaaacac    780

uccaugguag acagaggaug ggaaaugga ugugggauuau uuggaaaggg aggcauugug    840

accugugcua uguucacaug caaaaagaac auggaaggaa aaaucgugca accagaaaau    900

uuggaauaca ccaucgugau aacaccucac ucaggagaag agcacgcugu agguaaugac    960

acaggaaaac augguaagga aauuaaaaua acaccacaga guuccaucac agaagcagaa   1020

cugacaggcu auggcacagu cacgauggag ugcucuccga gaacgggccu ugacuucaau   1080

gagauggugc ugcugcagau ggaagauaaa gcuuggcugg ugcacaggca augguuccua   1140

gaccugccgu uaccauggcu acccggagcg gacacacaag gaucaaauug gauacagaaa   1200

gagacauugg ucacuuucaa aaaucccccac gcgaagaagc aggaugucgu uguuuuagga   1260

ucucaagaag gagccaugca cacggcacuc acaggggcca cagaaaucca gaugucauca   1320

ggaaacuuac uauucacagg acaucucaaa ugcaggcuga gaauggacaa acuacagcuc   1380

aaaggaaugu cauacucuau guguacagga aaguuuaaaa uugugaagga aauagcagaa   1440

acacaacaug gaacaauagu uaucagagua caauaugaag gagacggcuc uccauguaag   1500
```

aucccuuuug aaauaaugga uuuggaaaaa agacaugucu uaggucgccu gauuacaguu 1560
aauccgaucg uaacagaaaa agauagccca gucaacauag aagcagaacc uccauucgga 1620
gacagcuaca ucauuauagg aguagagccg ggacaauuga aacucaacug guucaagaaa 1680
ggaaguucca ucggccaaau guuugagacg acaaugagag gagcaaagag aauggccauu 1740
uuaggugaca cagccuggga uuuuggaucu cugggaggag uguuuacauc uauaggaaag 1800
gcucuccacc aaguuuucgg agcaaucuau ggggcugccu uuaguggggu uucauggacu 1860
augaaaaucc ucauaggagu caucaucaca uggauaggaa ugaauucacg uagcaccuca 1920
cugucugugu cacuaguauu ggugggaauc auaacacugu acuugggagc uauggugcag 1980
gcu 1983

<210> SEQ ID NO 6
<211> LENGTH: 10735
<212> TYPE: RNA
<213> ORGANISM: Artificial Sequence
<220> FEATURE:
<223> OTHER INFORMATION: VDV1

<400> SEQUENCE: 6
aguuguuagu cuacguggac cgacaagaac aguuucgaau cggaagcuug cuuaacguag 60
uucuaacagu uuuuuauuag agagcagauc ucugaugauc aaccaacgaa aaaagacggg 120
ucgaccgucu uucaauaugc ugaaacgcgc gagaaaccgc gugucaacug uuucacaguu 180
ggcgaagaga uucucaaaag gauugcucuc aggccaagga cccaugaaau uggugauggc 240
uuucauagca uucuuaagau uucuagccau acccccaaca gcaggaauuu uggcuagaug 300
gggcucauuc aagaagaaug gagcgauuaa aguguuacgg gguuucaaga gagaaaucuc 360
aaacaugcua aacauaauga acaggaggaa aagauccgug accaugcucc uuaugcugcu 420
gcccacagcc cuggcguucc aucugacgac acgaggggga gagccgcaua ugauaguuag 480
caagcaggaa agaggaaagu cacuuuuguu caagaccucu gcagguguca acaugugcac 540
ccucauugcg auggauuugg gagaguugug ugaggacacg augaccuaca aaugcccccg 600
gaucacugag gcggaaccag augacguuga cuguuggugc aaugccacgg acacaugggu 660
gaccuaugga acgugcucuc aaacuggcga acaccgacga gacaaacguu ccgucgcauu 720
ggccccacac guggggcuug gccuagaaac aagagccgaa acguggaugu ccucugaagg 780
ugcuuggaaa cagauacaaa aaguagagac uugggcucug agacauccag gauucacggu 840
gauagcccuu uuucuagcac augccauagg aacauccauc acccagaaag ggaucauuuu 900
cauuuugcug augcugguaa caccaucuau ggccaugcga ugcgugggaa uaggcaacag 960
agacuucgug gaaggacugu caggagcaac augggguggau gugguacugg agcauggaag 1020
uugcgucacc accauggcaa aaaacaaacc aacacuggac auugaacucu ugaagacgga 1080
ggucacaaac ccugcaguuc ugcguaaauu gugcauugaa gcuaaaauau caaacaccac 1140
caccgauucg agauguccaa cacaaggaga agccacacug guggaagaac aagacgcgaa 1200
cuuugugugc cgacgaacgu ucguggacag aggcuggggc aauggcugug ggcuauucgg 1260
aaaagguagu cuaauaacgu gugccaaguu uaagugugug acaaaacuag aaggaaagau 1320
agcucaauau gaaaaccuaa aauauucagu gauagucacc guccacacug gagaucagca 1380
ccagguggga aaugagacua cagaacaugg aacaacugca accauaacac cucaagcucc 1440
uacgucggaa auacagcuga ccgacuacgg aacccuuaca uuagauuguu caccuaggac 1500
agggcuagau uuuaacgaga uggugugucu gacaaugaaa aagaaaucau ggcuugucca 1560
caaacagugg uuucuagacu uaccacugcc uuggaccucu ggggcuuuaa caucccaaga 1620
gacuuggaac agacaagauu uacuggucac auuuaagaca gcucaugcaa agaagcagga 1680
aguagucgua cuaggaucac aagaaggagc aaugcacacu gcgcugacug gagcgacaga 1740
aauccaaacg ucaggaacga caacaauuuu cgcaggacac cuaaaaugca gacuaaaaau 1800
ggacaaacua acuuuaaaag ggaugucaua ugugaugugc acaggcucau ucaaguuaga 1860
gaaagaagug gcugagaccc agcauggaac uguucuggug cagguuaaau augaaggaac 1920
agacgcacca ugcaagauuc ccuuuucgac ccaagaugag aaaggagcaa cccagaaugg 1980
gagauuaaua acagccaacc ccauagucac ugacaaagaa aaaccaguca auauugaggc 2040
agaaccaccc uuuggugaga gcuacaucgu gguaggagca ggugaaaaag cuuugaaacu 2100
aagcugguuc aagaaaggaa gcagcauagg gaaaauguuu gaagcaacug cccgaggagc 2160
acgaaggaug gccauucugg gagacaccgc augggacuuc gguucuauag gaggaguguu 2220
cacgucuaug ggaaaacugg uacaccaggu uuuuggaacu gcauauggag uuuuguuuag 2280
cggaguuucu uggaccauga aaauaggaau agggauucug cugacauggc uaggauuaaa 2340
uucaaggaac acgucccuuu cggugaugug caucgcaguu ggcaugguca cacuguaccu 2400
aggagucaug guucaggcag auucgggaug uguaaucaac uggaaaggca gagaacuuaa 2460
auguggaagc ggcauuuuug ucacuaauga aguucacacu uggacagagc aauacaaauu 2520
ccaggcugac ucccccaaga gacuaucagc agccauuggg aaggcauggg aggagggugu 2580
guguggaauc cgaucagcca cucgucucga gaacaucaug uggaaacaaa uaucaaauga 2640
auugaaccac auccuacuug aaaaugacau gaaauuuaca guggucgugg gagacguuag 2700
uggaaucuug gcccaaggaa aaaaaaugau uaggccacaa cccauggaac acaaauacuc 2760
guggaaaagc uggggaaaag cuaaaaucau aggagcggau guacagaaca ccaccuucau 2820
caucgacggc ccaaacaccc cagaaugccc ugacaaucaa agagcaugga auauuuggga 2880
aguagaggac uauggauuug ggauuuucac gacaaacaua ugguugaaau ugcgugacuc 2940
cuacacccaa guaugugacc accggcugau gucagcugcc auuaaggaca gcaaggcagu 3000
ccaugcugac augggguacu ggauagaaag ugaaaagaac gagacaugga aguuggcgag 3060
agccuccuuu auagaaguua agacaugcau cuggccaaaa ucccacacuc uauggagcaa 3120
uggaguucug gaaagugaaa ugauaauucc aaagauauau ggaggaccaa uaucucagca 3180
caacuacaga ccaggauauu ucacacaaac agcagggccg uggcaccuag gcaaguugga 3240
acuagauuuc gauuuuugug aagguaccac aguuguugug gaugaacauu guggaaaucg 3300
aggaccaucu cucagaacca caacagucac aggaaagaua auccaugaau ggugcugcag 3360
aucuuguacg cuacccccc uacguuucaa aggggaagac ggguguuggu acggcaugga 3420
aaucagacca gugaaggaca aggaagagaa ccuggucaag ucaauggucu cugcaggguc 3480
aggagaagug gacagcuuuu cacuaggacu gcuaugcaua ucaauaauga uugaagaagu 3540
gaugagaucc agauggagca aaaaaaugcu gaugacugga acacuggcug uguuccuccu 3600
ucuuauaaug ggacaauuga cauggaguga ucugaucagg uuauguauua ugguuggagc 3660
caacgcuuca gacaagaugg ggaugggaac aacguaccua gcuuuaaugg ccacuuucaa 3720
aaugagacca auguucgccg ucgggcuauu auuucgcaga cuaacaucua gagaaguucu 3780
ucuucuuaca auuggcuuga gccugguggc auccguggag cuaccaaguu cccuagagga 3840
gcugggggau ggacuugcaa uaggcaucau gauguugaaa uuauugacug auuucaguc 3900

-continued acaccagcua ugggcuacuc ugcuauccuu gacauuuauu aaaacaacuu uuucauugca 3960
cuaugcaugg aagacaaugg cuaugguacu gucaauugua ucucucuucc cuuuaugccu 4020
guccacgacc ucucaaaaaa caacauggcu uccggugcug uugggaucuc uuggaugcaa 4080
accacuaccc auguuucuua uaacagaaaa caaaaucugg ggaaggaaga guuggccccu 4140
caaugaagga auuauggcug uuggaauagu uaguauucua cuaaguucac uuuuaaaaaa 4200
ugaugugccg cuagccggcc cauuaauagc uggaggcaug cuaauagcau guuaugucau 4260
auccggaagc ucagcugauu uaucacugga gaaagcggcu gaggucuccu gggaggaaga 4320
agcagaacac ucaggcgccu cacacaacau acuaguagag guucaagaug auggaaccau 4380
gaagauaaaa gaugaagaga gagaugacac gcucaccauu cuccuuaaag caacucugcu 4440
ggcagucuca gggguguacc caaugucaau accagcgacc cuuuuugugu gguauuuuug 4500
gcagaaaaag aaacagagau caggagugcu augggacaca cccagccccc cagaagugga 4560
aagagcaguu cuugaugaug gcaucuauag aauuuugcaa agaggacugu ugggcagguc 4620
ccaaguagga guaggaguuu uccaagaagg cguguuccac acaaugwggc acgucacuag 4680
gggagcuguc cucauguauc aaggaaaaag gcuggaacca agcugggcca gugucaaaaa 4740
agacuugauc ucauauggag gagguuggag guuucaagga uccuggaaca cgggagaaga 4800
aguacaggug auugcuguug aaccgggaaa aaaccccaaa aauguacaaa caacgccggg 4860
uaccuucaag accccugaag gcgaaguugg agccauagcc uuagacuuua aaccuggcac 4920
aucuggaucu cccaucguaa acagagaggg aaaaauagua ggucuuuaug gaaauggagu 4980
ggugacaaca agcggaacuu acguuagugc cauagcucaa gcuaaggcau cacaagaagg 5040
gccucuacca gagauugagg acaaggugu uaggaaaaga aacuuaacaa uaauggaccu 5100
acauccagga ucgggaaaaa caagaagaua ccuuccagcc auaguccgug aggccauaaa 5160
aaggaagcug cgcacgcuaa ucccuagcucc cacaagaguu gucgcuucug aaauggcaga 5220
ggcacucaag ggagugccaa uaagguauca gacaacagca gugaagagug aacacacagg 5280
aaaggagaua guugaccuua ugugccacgc cacuuucacc augcgccucc ugucucccgu 5340
gagaguuccc aauuauaaca ugauuaucau ggaugaagca cacuucaccg auccagccag 5400
cauagcagcc agaggguaca ucucaacccg aguggguaug ggugaagcag cugcgaucuu 5460
uaugacagcc acucccccag gaucggugga ggccuuucca cagagcaaug caauuaucca 5520
agaugaggaa agagacauuc cugagagauc auggaacuca ggcuaugacu ggaucacuga 5580
uuuuccaggu aaaacagucu gguuuguucc aagcaucaaa ucaggaaaug acauugccaa 5640
cuguuuaaga aaaaacggga aacgggugau ccaauugagc agaaaaaccu uugacacuga 5700
guaccagaaa acaaaaaaca acgacuggga cuaugucguc acaacagaca uuuccgaaau 5760
gggagcaaau uuccgggccg acaggguaau agacccaagg cggugucuga aaccgguaau 5820
acuaaaagau gguccagagc gcgucauucu agccggaccg augccaguga cuguggccag 5880
ugccgcccag aggagaggaa gaauuggaag gaaccaaaac aaggaaggug aucaguauau 5940
uuacauggga cagccuuuaa aaaaugauga ggaccacgcu cauuggacag aagcaaagau 6000
gcuccuugac aauauaaaca caccagaagg gauuauccca gcccucuuug agccggagag 6060
agaaaagagu gcagcuauag acggggaaua cagacugcgg ggugaagcaa ggaaaacguu 6120
cguggagcuc augagaagag gggaucuacc agucuggcua uccuacaaag uugccucaga 6180
aggcuuccag uacuccgaca gaagguggug cuucgauggg gaaaggaaca accaggugu 6240
ggaggagaac auggacgugg agaucuggac aaaagaagga gaaagaaaga aacuacgacc 6300
ucgcugguug gacgccagaa cauacucuga cccacuggcu cugcgcgagu uuaaagaguu 6360
ugcagcagga agaagaagcg ucucaggugu ccuaauauua gaaauaggga aacuuccaca 6420
acauuugacg caaagggccc agaaugcuuu ggacaacuug gucauguugc acaauuccga 6480
acaaggagga aaagccuaua gacaugcuau ggaagaacug ccagacacaa uagaaacguu 6540
gaugcuccua gccuugauag cuguguugac ugguggagug acgcuguucu uccuaucagg 6600
aagaggucua ggaaaaacau cuaucggcuu acucugcgug auggccucaa gcgcacuguu 6660
auggauggcc aguguggagc cccauuggau agcggccucc aucauacugg aguucuuucu 6720
gaugguacug cuuauuccag agccagacag acagcgcacu ccacaggaca accagcuagc 6780
auauguggug auaggucugu uauucgugau auugacagug gcagccaaug agaugggauu 6840
auuggaaacc acaaagaaag accuggggau uggccaugua gcugcugaaa accaccacca 6900
ugcuacaaug cuggacguag accuacaucc agcuucagcc uggacccucu augcaguggc 6960
cacaacaauc aucacuccua ugaugagaca cacaauugaa aacacaacgg caaauauuuc 7020
ccugacagcc aucgcaaacc aagcagcuau auugauggga cuugacaagg gauggccaau 7080
aucgaagaug gacauaggag uuccacuucu cgccuugggg ugcuauuccc aagugaaucc 7140
gcugacacug auagcggcag uauugaugcu aguagcucau uacgccauaa uuggaccugg 7200
acugcaagca aaagcuacua gagaagcuca aaaaagaaca gcggcuggaa uaaugaaaaa 7260
uccaacuguc gacgggauug uugcaauaga cuuagauccc gugguuuacg augcaaaauu 7320
ugaaaaacag cuaggccaaa uaauguuguu gauacuuugc acaucacaga uucuuuugau 7380
gcggacuaca ugggccuugu gugaauccau cacauuggcu acuggaccuc ugaccacucu 7440
uugggaggga ucuccaggaa aauucuggaa caccacaaua gcgguaucca uggcaaacau 7500
uuucaggggg aguuaucuag caggagcagg ucuggccuuc ucauuaauga aaucucuagg 7560
aggagguagg agaggcacgg gagcccaagg ggaaacacug ggagaaaaau ggaaaagaca 7620
acuaaaccaa cugagcaagu cagaauucaa uacuuacaag aggaguggga uuauggaggu 7680
ggauagaucc gaagccaaag agggacugaa aagaggagaa acaaccaaac acgcaguauc 7740
gagaggaacg gccaaacuga gguggguucgu ggagaggaac cuugugaaac cagaagggaa 7800
agucauagac cucgguugug gaagaggugg cuggucauau uauugcgcug ggcugaagaa 7860
agucacagaa gugaaaggau acacaaaagg aggaccugga caugaggaac caaucccaau 7920
ggcgaccuau ggauggaacc uaguaaggcu gcacuccgga aaagauguau uuuuuauacc 7980
accugagaaa ugugacaccc uuuuguguga uauuggugag uccucuccga acccaacuau 8040
agaggaagga agaacguuac guguucugaa aaugguggaa ccauggcuca gaggaaacca 8100
auuuugcaua aaaauucuaa aucccuauau gccgagcgug guagaaacuc uggaacaaau 8160
gcaaagaaaa cauggaggaa ugcuagugcg aaacccacuc ucaagaaauu ccacccauga 8220
aauguacugg guuucaugug gaacaggaaa cauuguguca gcaguaaaca ugacaucuag 8280
aauguugcua aaucgguuca caauggcuca caggaagcca acauaugaaa gagacgugga 8340
cuuaggcgcu ggaacaagac auguggcagu agaaccagag guagccaacc uagauaucau 8400
uggccagagg auagagaaua uaaaaaauga acauaaguca acauggcauu augaugagga 8460
caauccauac aaaacauggg ccuaucaugg aucauaugag guuaagccau caggaucggc 8520
cucauccaug gucaauggcg uggugagauu gcucaccaaa ccaugggaug uuauccccau 8580
ggucacacaa auagccauga cugauaccac acccuuugga caacagaggg uguuuaaaga 8640

-continued

```
gaaaguugac acgcgcacac caaaagcaaa acguggcaca gcacaaauua uggaagugac   8700
agccaggugg uuaugggguu uccuuucuag aaacaaaaaa cccagaauuu gcacaagaga   8760
ggaguuuaca agaaaaguua ggucaaacgc agcuauugga gcaguguucg uugaugaaaa   8820
ucaauggaac ucggcaaaag aagcagugga agacgaacgg uucugggaac uuguccacag   8880
agagagggag cuucauaaac aggggaaaug ugccacgugu gucuacaaua ugaugggga    8940
gagagagaaa aaauuaggag aguucggaaa ggcaaaagga agucgugcaa uaugguacau   9000
gugguuggga gcacgcuucc uagaguuuga agcccuuggu uucaugaaug aagaucacug   9060
guucaguaga gagaauucac ucaguggagu ggaaggagaa ggacuccaca aacuuggaua   9120
cauacucaga gacauaucaa ggauuccagg ggggaacaug uaugcagaug acacagccgg   9180
augggacaca agaauaacag aggaugaucu ccagaaugag gcuaaaaauca cugacaucau  9240
ggagcccgaa caugcccugc uggcuacguc aaucuuuaag cugaccuacc aaaauaaggu   9300
gguaagggug cagagaccag caaaaaaugg aaccgugaug gauguuauau ccagacguga   9360
ccagagaggc aguggacagg uuggaacuua uggcuuaaac acuuucacca acauggaggc   9420
ccaacugaua agacaaaugg agucugaggg aaucuuuuua cccagcgaau uggaaacccc   9480
aaaucuagcc ggaagaguuc ucgacugguu ggaaaaaauau ggugucgaaa ggcugaaaag  9540
aauggcaauc agcggagaug acugugugu gaaaccaauu gaugacaggu ucgcaacagc    9600
cuuaacagcu uugaaugaca ugggaaaagu aagaaaagac auaccacaau gggaaccuuc   9660
aaaaggaugg aaugauuggc aacaagugcc uuucuguuca caccacuucc accagcuaau   9720
uaugaaggau gggagggaga uaguggugcc augccgcaac caagaugaac uugugggggag  9780
ggccagagua ucacaaggcg ccggauggag ccugagagaa accgcaugcc uaggcaaguc   9840
auaugcacaa auguggcagc ugauguauuu ccacaggaga gaccugagac uggcggcuaa   9900
cgcuauuugu ucagccguuc caguugauug ggucccaacc agccgcacca ccuggucgau   9960
ccaugcccau caccaaugga ugacaacaga agacauguua ucaguaugga auagggucug  10020
gauagaggaa aacccaugga uggaggauaa gacucaugug uccaguuggg aagaaguucc  10080
auaccuagga aagagggaag aucaguggug uggaucccug auaggcuuaa cagcaagggc  10140
caccugggcc acuaauauac aaguggccau aaaccaagug agaaggcuca uugggaauga  10200
gaauuaucua gauuacauga caucaaugaa gagauucaag aaugagagug aucccgaagg  10260
ggcacucugg uaagucaaca cauucacaaa auaaaggaaa auaaaaaauc aaaugaggca  10320
agaagucagg ccagauuaag ccauaguacg guaagagcua ugcugccugu gagccccguc  10380
caaggacgua aaaugaaguc aggccgaaag ccacgguuug agcaagccgu gcugccugug  10440
gcuccaucgu ggggauguaa aaacccggga ggcugcaacc cauggaagcu guacgcaugg  10500
gguagcagac uagugguuag aggagacccc ucccaagaca caacgcagca gcggggccca  10560
acaccagggg aagcuguacc cuggugguaa ggacuagagg uuagaggaga cccccccgcgu 10620
aacaauaaac agcauauuga cgcugggaga gaccagagau ccugcugucu cuacagcauc  10680
auuccaggca cagaacgcca gaaaauggaa uggugcuguu gaaucaacag guucu        10735
```

<210> SEQ ID NO 7
<211> LENGTH: 10723
<212> TYPE: RNA
<213> ORGANISM: Artificial Sequence
<220> FEATURE:
<223> OTHER INFORMATION: VDV2

<400> SEQUENCE: 7

```
aguuguuagu cuacguggac cgacaaagac agauucuuug agggagcuaa gcucaaugua     60
guucuaacag uuuuuuaauu agagagcaga ucucugauga auaaccaacg gaaaaaggcg    120
aaaaacacgc cuuucaauau gcugaaacgc gagagaaacc gcgugucgac ugugcaacag    180
cugacaaaga gauucucacu uggaaugcug cagggacgag gaccauuaaa acuguucaug    240
gcccuggugg cguuccuucg uuuccuaaca aucccaccaa cagcagggau auugaagaga    300
uggggaacaa uuaaaaaauc aaaagcuauu aauguuuuga gaggguucag gaaagagauu    360
ggaaggaugc ugaacaucuu gaauaggaga cgcagaucug caggcaugau cauuaugcug    420
auuccaacag ugauggcguu ccauuuaacc acacguaacg gagaaccaca caugaucguc    480
agcagacaag agaaagggaa aagucuucug uuuaaaacag agguuggcgu gaacaugugu    540
acccucaugg ccauggaccu uggugaauug ugugaagaca caaucacgua caagaguccc    600
cuucucaggc agaaugagcc agaagacaua gacuguuggu gcaacucuac guccacgugg    660
guaacuuaug ggacguguac caccauggga gaacauagaa gagaaaaaag aucaguggca    720
cucguuccac augugcgaau gggacuggag acacgaacug aaacauggau gucaucagaa    780
ggggccugga aacaugucca gagaauugaa acuuggaucu ugagacaucc aggcuucacc    840
augauggcag caauccuggc auacaccaua ggaacgacac auuuccaaag agcccugauu    900
uucaucuuac ugacagcugu cacuccuuca augacaaugc guugcauagg aaugucaaau    960
agagacuuug uggaaggggu uucaggagga agcuggguug acauagucuu agaacaugga   1020
agcuguguga cgacgauggc aaaaaacaaa ccaacauugg auuuugaacu gauaaaaaca   1080
gaagccaaac agccugccac ccuaaggaag uacuguauag aggcaaagcu aaccaacaca   1140
acaacagaau cucgcugccc aacacaaggg gaacccagcc uaaaugaaga gcaggacaaa   1200
agguucgucu gcaaacacuc caugguagac agaggauggg gaaauggaug uggacuauuu   1260
ggaaagggag gcauugugac cugugcuaug uucagaugca aaaagaacau ggaaggaaaa   1320
guugugcaac cagaaaacuu ggaauacacc auugugauaa caccucacuc aggggaagag   1380
caugcagucg gaaaugacac aggaaaacau ggcaaggaaa ucaaaauaac accacagagu   1440
uccaucacag aagcagaauu gacagguuau ggcacuguca caauggagug cucuccaaga   1500
acgggccucg acuucaauga gaugguguug cugcagaugg aaaauaaagc uuggcuggug   1560
cacaggcaau gguuccuaga ccugccguua ccaugguugc ccggagcgga cacacaagag   1620
ucaaauugga uacagaagga gacauugguc acuuucaaaa auccccaugc gaagaaacag   1680
gauguuguug uuuuaggauc ccaagaaggg gccaugcaca cagcacuuac aggggccaca   1740
gaaauccaaa ugucaucagg aaacuuacuc uucacaggac aucucaagug caggcugaga   1800
auggacaagc uacagcucaa aggaauguca uacucuaugu gcacaggaaa guuuaaaguu   1860
gugaaggaaa uagcagaaac acaacaugga acaauaguua ucagagugca auaugaaggg   1920
gacggcucuc caugcaagau cccuuuugag auaauggauu uggaaaaaag acaugucuua   1980
ggucgccuga uuacagucaa cccaauugug acagaaaaag auagcccagu caacauagaa   2040
gcagaaccuc cauuuggaga cagcuacauc aucauaggag uagagccggg acaacugaag   2100
cucaacuggu uuaagaaagg aaguucuauc ggccaaaugu uugagacaac aaugaggggg   2160
gcgaagagaa uggccauuuu aggugacaca gccugggauu uuggauccuu gggaggagug   2220
uuuacaucua uaggaaaggc ucuccaccaa gucuuuggag caaucuaugg agcugccuuc   2280
agugggguuu cauggacuau gaaaauccuc auaggaguca uuaucacaug gauaggaaug   2340
```

-continued

```
aauucacgca gcaccucacu gucugugaca cuaguauugg ugggaauugu gacacuguau   2400
uugggaguca uggugcaggc cgauaguggu ugcguuguga gcuggaaaaa caaagaacug   2460
aaauguggca gugggauuuu caucacagac aacgugcaca cauggacaga acaauacaaa   2520
uuccaaccag aaucccccuuc aaaacuagcu ucagcuaucc agaaagccca ugaagaggac   2580
auuuguggaa uccgcucagu aacaagacug gagaaucuga uguggaaaca aauaacacca   2640
gaauugaauc acauucuauc agaaaaugag gugaaguuaa cuauuaugac aggagacauc   2700
aaaggaauca ugcaggcagg aaaacgaucu cugcggccuc agcccacuga gcugaaguau   2760
ucauggaaaa cauggggcaa agcaaaaaug cucucuacag agucucauaa ccagaccuuu   2820
cucauugaug gccccgaaac agcagaaugc cccaacacaa auagagcuug gaauucguug   2880
gaaguugaag acuauggcuu uggaguauuc accaccaaua uauggcuaaa auugaaagaa   2940
aaacaggaug uauucugcga cucaaaacuc augucagcgg ccauaaaaga caacagagcc   3000
guccaugccg auaugguua uuggauagaa agugcacuca augacacaug gaagauagag   3060
aaagccucuu ucauugaagu uaaaaacugc cacuggccaa aaucacacac ccucuggagc   3120
aauggagugc uagaaaguga gaugauaauu ccaaagaauc ucgcuggacc agugucucaa   3180
cacaacuaua gaccaggcua ccauacacaa auaacaggac cauggcaucu agguaagcuu   3240
gagauggacu uugauuucug ugauggaaca acagugguag ugacugagga cugcggaaau   3300
agaggacccu cuuugagaac aaccacugcc ucuggaaaac ucauaacaga auggugcugc   3360
cgaucuugca cauuaccacc gcuaagauac agaggugagg augggugcug guacgggaug   3420
gaaaucagac cauugaagga gaaagaagag aauuugguca acuccuuggu cacagcugga   3480
caugggcagg ucgacaacuu uucacuagga gucuugggaa uggcauuguu ccuggaggaa   3540
augcuuagga cccgaguagg aacgaaacau gcaauacuac uaguugcagu uucuuuugug   3600
acauugauca cagggaacau guccuuuaga gaccugggaa gagugauggu uaugguaggc   3660
gccacuauga cggaugacau agguaugggc gugacuuauc uugcccuacu agcagccuuc   3720
aaagucagac caacuuuugc agcuggacua cucuugagaa agcugaccuc caaggaauug   3780
augaugacua cuauaggaau uguacuccuc ucccagagca ccauaccaga gaccauucuu   3840
gaguugacug augcguuagc cuuaggcaug augguccuca aaauggugag aaauauggaa   3900
aaguaucaau uggcagugac uaucauggcu aucuugugcg ucccaaacgc agugauauua   3960
caaaacgcau ggaaagugag uugcacaaua uuggcagugg uguccguuuc cccacuguuc   4020
uuaacauccu cacagcaaaa aacagauugg auaccauuag cauugacgau caaaggucuc   4080
aauccaacag cuauuuuucu aacaacccuc ucaagaacca gcaagaaaag gagcuggcca   4140
uuaaaugagg cuaucauggc agucgggaug gugagcauuu uagccaguuc ucuccuaaaa   4200
aaugauauuc ccaugacagg accauuagug gcuggagggc uccucacugu gugcuacgug   4260
cucacuggac gaucggccga uuuggaacug gagagagcag ccgaugucaa augggaagac   4320
caggcagaga uaucaggaag caguccaauc cugucaauaa caauaucaga agaugguagc   4380
augucgauaa aaaaugaaga ggaagaacaa acacugacca uacucauuag aacaggauug   4440
cuggugaucu caggacuuuu uccuguauca auaccaauca cggcagcagc augguaccug   4500
ugggaaguga agaaacaacg ggccggagua uuguggggaug uuccuucacc cccacccaug   4560
ggaaaggcug aacuggaaga uggagccuau agaauuaagc aaaaagggau ucuuggauau   4620
ucccagaucg gagccggagu uuacaaagaa ggaacauucc auacaaugug gcaugucaca   4680
cguggcgcug uucuaaugca uaaaggaaag aggauugaac caacaugggc ggacgucaag   4740
```

-continued aaagaccuaa uaucauaugg aggaggcugg aaguuagaag gagaauggaa ggaaggagaa 4800
gaaguccagg uauuggcacu ggagccugga aaaaauccaa gagccgucca aacgaaaccu 4860
ggucuuuuca aaaccaacgc cggaacaaua ggugcuguau cucuggacuu uucuccugga 4920
acgucaggau cuccaauuau cgacaaaaaa ggaaaaguug ugggucuuua ugguaauggu 4980
guuguuacaa ggaguggagc auaugugagu gcuauagccc agacugaaaa aagcauugaa 5040
gacaacccag agaucgaaga ucacauuuuc cgaaagagaa gacugaccau cauggaccuc 5100
cacccaggag cgggaaagac gaagagauac cuuccggcca uagucagaga agcuauaaaa 5160 cggggguuuga gaacauuaau cuuggccccc acuagaguug uggcagcuga aauggaggaa 5220
gcccuuagag gacuuccaau aagauaccag accccagcca ucagagcuga gcacaccggg 5280
cgggagauug uggaccuaau gugucaugcc acauuuacca ugaggcugcu aucaccaguu 5340
agagugccaa acuacaaccu gauuaucaug gacgaagccc auuucacaga cccagcaagu 5400
auagcagcua gaggauacau cucaacucga guggagaugg gugaggcagc ugggauuuuu 5460
augacagcca cucccccggg aagcagagac ccauuuccuc agagcaaugc accaaucaua 5520
gaugaagaaa gagaaauccc ugaacgcucg uggaauuccg gacaugaaug ggucacggau 5580
uuuaaaggga agacuguuug guucguucca aguauaaaag caggaaauga uauagcagcu 5640
ugccugagga aaaauggaaa gaaagugaua caacucagua ggaagaccuu ugauucugag 5700
uaugucaaga cuagaaccaa ugauugggac uucgugguua caacugacau uucagaaaug 5760
ggugccaauu ucaaggcuga gaggguuaua gaccccagac gcugcaugaa accagucaua 5820
cuaacagaug gugaagagcg ggugauucug gcaggaccua ugccagugac ccacucuagu 5880
gcagcacaaa gaagagggag aauaggaaga aauccaaaaa augagaauga ccaguacaua 5940 uacaugggggg aaccucugga aaaugaugaa gacugugcac acuggaaaga agcuaaaaug 6000
cuccuagaua acaucaacac gccagaagga aucauuccua gcauguucga accagagcgu 6060
gaaaaggugg augccauuga uggcgaauac cgcuugagag gagaagcaag gaaaaccuuu 6120
guagacuuaa ugagaagagg agaccuacca gucugguugg ccuacagagu ggcagcugaa 6180
ggcaucaacu acgcagacag aaggugguggu uuugauggag ucaagaacaa ccaaauccua 6240
gaagaaaacg uggaaguuga aaucuggaca aaagaagggg aaaggaagaa auugaaaccc 6300
agaugguugg augcuaggau cuauucugac ccacuggcgc uaaaagaauu uaaggaauuu 6360
gcagccggaa gaaagucucu gacccugaac cuaaucacag aaaugggguag gcucccaacc 6420 uucaugacuc agaaggcaag agacgcacug gacaacuuag cagugcugca cacggcugag 6480
gcagguggaa gggcguacaa ccaugcucuc agugaacugc cggagacccu ggagacauug 6540
cuuuuacuga cacuucuggc uacagucacg ggagggaucu uuuuauucuu gaugagcgca 6600
aggggcauag ggaagaugac ccugggaaug ugcugcauaa ucacggcuag cauccuccua 6660
ugguacgcac aaauacagcc acacuggaua gcagcuucaa uaauacugga guuuuuucuc 6720
auaguuuugc uuauuccaga accugaaaaa cagagaacac cccaagacaa ccaacugacc 6780
uacguuguca uagccauccu cacaguggug gccgcaacca uggcaaacga gauggguuuc 6840
cuagaaaaaa cgaagaaaga ucucggauug ggaagcauug caacccagca acccgagagc 6900
aacauccugg acauagaucu acguccugca ucagcaugga cgcuguaugc cguggccaca 6960
acauuuguua caccaauguu gagacauagc auugaaaauu ccucagugaa ugugucccua 7020
acagcuauag ccaaccaagc cacaguguua augggucucg ggaaaggaug gccauuguca 7080

-continued aagauggaca ucggaguucc ccuucucgcc auuggaugcu acucacaagu caaccccaua 7140
acucucacag cagcucuuuu cuuauuggua gcacauuaug ccaucauagg gccaggacuc 7200
caagcaaaag caaccagaga agcucagaaa agagcagcgg cgggcaucau gaaaaaccca 7260
acugucgaug gaauaacagu gauugaccua gauccaauac cuuaugaucc aaaguuugaa 7320
aagcaguugg gacaaguaau gcuccuaguc cucugcguga cucaaguauu gaugaugagg 7380
acuacauggg cucuguguga ggcuuuaacc uuagcuaccg ggcccaucuc cacauugugg 7440
gaaggaaauc cagggagguu uuggaacacu accauugcgg ugucaauggc uaacauuuuu 7500
agagggaguu acuuggccgg agcuggacuu cucuuuucua uuaugaagaa cacaaccaac 7560
acaagaaggg gaacuggcaa cauaggagag acgcuuggag agaaauggaa aagccgauug 7620
aacgcauugg gaaaaaguga auuccagauc uacaagaaaa guggaaucca ggaaguggau 7680
agaaccuuag caaaagaagg cauuaaaaga ggagaaacgg accaucacgc ugugucgcga 7740
ggcucagcaa aacugagaug guucguugag agaaacaugg ucacaccaga agggaaagua 7800
guggaccucg guuguggcag aggaggcugg ucauacuauu guggaggacu aaagaaugua 7860
agagaaguca aaggccuaac aaaaggagga ccaggacacg aagaacccau ccccauguca 7920
acauaugggu ggaaucuagu gcgucuucaa aguggaguug acguuuucuu caucccgcca 7980
gaaaagugug acacauuauu gugugacaua ggggagucau caccaaaucc cacaguggaa 8040
gcaggacgaa cacucagagu ccuuaacuua guagaaaauu gguugaacaa caacacucaa 8100
uuuugcauaa agguucucaa cccauauaug cccucaguca uagaaaaaau ggaagcacua 8160
caaaggaaau auggaggagc cuuagugagg aauccacucu cacgaaacuc cacacaugag 8220
auguacuggg uauccaaugc uuccgggaac auagugucau cagugaacau gauuucaagg 8280
auguugauca acagauuuac aaugagauac aagaaagcca cuuacgagcc ggauguugac 8340
cucggaagcg gaacccguaa caucgggauu gaaagugaga uaccaaaccu agauauaauu 8400
gggaaaagaa uagaaaaaau aaagcaagag caugaaacau cauggcacua ugaccaagac 8460
cacccauaca aaacgugggc auaccauggu agcuaugaaa caaaacagac uggaucagca 8520
ucauccaugg ucaacggagu ggucaggcug cugacaaaac cuugggacgu uguccccaug 8580
gugacacaga uggcaaugac agacacgacu ccauuuggac aacagcgcgu uuuuaaagag 8640
aaaguggaca cgagaaccca agaaccgaaa gaaggcacga agaaacuaau gaaaauaaca 8700
gcagaguggc uuuggaaaga auuagggaag aaaaagacac ccaggaugug caccagagaa 8760
gaauucacaa gaaaggugag aagcaaugca gccuuggggg ccauauucac ugaugagaac 8820
aaguggaagu cggcacguga ggcuguugaa gauaguaggu uuugggagcu gguugacaag 8880
gaaaggaauc uccaucuuga aggaaagugu gaaacaugug uguacaacau gaugggaaaa 8940
agagagaaga agcuagggga auucggcaag gcaaaaggca gcagagccau augguacaug 9000
uggcuuggag cacgcuucuu agaguuugaa gcccuaggau ucuuaaauga agaucacugg 9060
uucuccagag agaacucccu gaguggagug gaaggagaag ggcugcacaa gcuagguuac 9120
auucuaagag acgugagcaa gaaagaggga ggagcaaugu augccgauga caccgcagga 9180
ugggauacaa aaaucacacu agaagaccua aaaaaugaag agaugguaac aaaccacaug 9240
gaaggagaac acaagaaacu agccgaggcc auuuucaaac uaacguacca aaacaaggug 9300
gugcgugugc aaagaccaac accaagaggc acaguaaugg acaucauauc gagaagagac 9360
caaagaggua guggacaagu uggcaccuau ggacucaaua cuuucaccaa uauggaagcc 9420
caacuaauca gacagaugga gggagaagga gucuuuaaaa gcauucagca ccuaacaauc 9480

-continued

```
acagaagaaa ucgcugugca aaacugguua gcaagagugg ggcgcgaaag guuaucaaga   9540
auggccauca guggagauga uuguguugug aaaccuuuag augacagguu cgcaagcgcu   9600
uuaacagcuc uaaaugacau gggaaagauu aggaaagaca uacaacaaug ggaaccuuca   9660
agaggaugga augauuggac acaagugccc uucuguucac accauuucca ugaguuaauc   9720
augaaagacg gucgcguacu cguuguucca uguagaaacc aagaugaacu gauuggcaga   9780
gcccgaaucu cccaaggagc aggguggucu uugcgggaga cggccuguuu ggggaagucu   9840
uacgcccaaa uguggagcuu gauguacuuc cacagacgcg accucaggcu ggcggcaaau   9900
gcuauuugcu cggcaguacc aucacauugg guuccaacaa gucgaacaac cugguccaua   9960
caugcuaaac augaauggau gacaacggaa gacaugcuga cagucuggaa cagggugugg  10020
auucaagaaa acccauggau ggaagacaaa acuccagugg aaacauggga ggaaauccca  10080
uacuugggga aaagagaaga ccaauggugc ggcucauuga uuggguuaac aagcagggcc  10140
accugggcaa agaacaucca agcagcaaua aaucaaguua gaucccuuau aggcaaugaa  10200
gaauacacag auuacaugcc auccaugaaa agauucagaa gagaagagga agaagcagga  10260
guucuguggu agaaagcaaa acuaacauga aacaaggcua gaagucaggu cggauuaagc  10320
cauaguacgg aaaaaacuau gcuaccugug agccccgucc aaggacguua aaagaaguca  10380
ggccaucaua aaugccauag cuugaguaaa cuaugcagcc uguagcucca ccugagaagg  10440
uguaaaaaau ccgggaggcc acaaaccaug gaagcuguac gcauggcgua guggacuagc  10500
gguuagggga gaccccuccc uuacaaaucg cagcaacaau gggggcccaa ggcgagauga  10560
agcuguaguc ucgcuggaag gacuagaggu uagaggagac ccccccgaaa caaaaaacag  10620
cauauugacg cugggaaaga ccagagaucc ugcugucucc ucagcaucau uccaggcaca  10680
gaacgccaga aaauggaaug gugcuguuga aucaacaggu ucu                     10723
```

VACCINE COMPOSITIONS AGAINST DENGUE VIRUS DISEASES

CROSS REFERENCE TO RELATED APPLICATIONS

This application is a United States non-provisional application filed under 35 U.S.C. § 371 based on international application no. PCT/EP2015/070060, filed on Sep. 2, 2015, which claims priority to European application no. EP 14306350.1, filed on Sep. 2, 2014, and European application no. EP 15305851.6, filed on Jun. 4, 2015, all three of which are incorporated by reference in their entirety.

FIELD OF THE INVENTION

The present invention relates to vaccine compositions and uses of such compositions in a method of protecting a human subject against dengue disease.

BACKGROUND

Dengue is the second most important infectious tropical disease after malaria with approximately one-half of the world's population living in areas where there is a risk of epidemic transmission. There are estimated to be 390 million cases of dengue every year and roughly 96 million people have clinically apparent disease. Each year, an estimated 500,000 people, including children, have a severe form of dengue requiring hospitalization, which puts a huge strain on health care systems during outbreaks, World Health Organization (WHO)—Global strategy for dengue prevention control: 2012-2020; available at: reliefweb.int/sites/reliefweb.int/files/resources/9789241504034enq.pdf. Approximately 2.5% of those affected with a severe form of dengue will die (Pan American Health Organisation May 2014—www.paho.org/hq/index.php?option=com_content&view=article&id=9657 <emid=1926.

Dengue disease is caused by four antigenically distinct, but closely related dengue virus serotypes of the flavivirus genus (Gubler et al., 1988, in: Epidemiology of arthropod-borne viral disease. Monath T P M, editor, Boca Raton (Fla.): CRC Press: 223-60; Kautner et al., 1997, J. of Pediatrics, 131: 516-524; Rigau-Perez et al., 1998, Lancet, 352: 971-977; Vaughn et al., 1997, J. Infect. Dis., 176: 322-30). Dengue viruses are positive-sense, single-stranded RNA viruses.

Dengue disease is usually transmitted by injection of the dengue virus during the blood meal of an *Aedes aegypti* mosquito infected by the virus. After an incubation period of 4-10 days, the illness begins abruptly and is followed by three phases: febrile (2 to 7 days), critical (24-48 hours—during which severe complications may occur) and recovery (48-72 hours). During the critical phase, life threatening complications such as haemorrhages, shock and acute organ impairment may occur. A proper management of these unpredictable outcomes can reduce the case fatality rate. Cure of dengue fever is complete after 7 to 10 days, but prolonged asthenia is normal. Reduced leukocyte and platelet numbers are frequently observed.

Severe forms of dengue disease including dengue haemorrhagic fever (DHF) are potentially deadly complication of dengue virus infection. DHF is characterized by a high fever and symptoms of dengue disease, but with extreme lethargy and drowsiness. Increased vascular permeability and abnormal homeostasis can lead to a decrease in blood volume, hypotension, and in severe cases, hypovolemic shock and internal bleeding. Two factors appear to play a major role in the occurrence of DHF—rapid viral replication with a high level of viraemia (the severity of the disease being associated with the level of viraemia; Vaughn et al., 2000, J. Inf. Dis., 181: 2-9) and a major inflammatory response with the release of high levels of inflammatory mediators (Rothman and Ennis, 1999, Virology, 257: 1-6; Alan L. Rothman. 2011, Nature Reviews Immunology, 11: 532-543). The mortality rate for DHF can reach 10% without treatment, but is <1% in most centres with access to treatment. Dengue disease infections are endemic in more than 100 tropical countries and DHF has been documented in 60 of these countries (Gubler, 2002, TRENDS in Microbiology, 10: 100-103).

Dengue shock syndrome (DSS) is a common progression of DHF and is frequently fatal. DSS results from generalized vasculitis leading to plasma leakage into the extravascular space. DSS is characterized by rapid and poor volume pulse, hypotension, cold extremities, and restlessness.

In Asia, DHF and DSS are observed primarily in children, with approximately 90% of those with DHF being less than 15 years of age (Malavige et al., 2004, Postgrad Med. J., 80: 588-601; Meulen et al., 2000, Trop. Med. Int. Health, 5:325-9). In contrast, outbreaks in the Caribbean and Central America have predominantly affected adults (Malavige et al., 2004, Postgrad Med. J., 80: 588-601). Incidence of dengue disease has increased in older age groups in many countries where dengue is endemic (Sabchareon et al, 2012, Lancet, 380, 1559-1567; Messina et al., 2014, Trends Microbiol., 22, 138-146).

The four serotypes of dengue virus possess approximately 60-80% sequence homology. Infection with one dengue serotype provides durable homologous immunity but limited heterologous immunity (Sabin, 1952, Am. J. Trop. Med. Hyg., 1: 30-50). Accordingly, an individual that has been infected with one serotype of dengue may subsequently become infected with a different serotype. It is considered that a second infection arising from a different dengue virus serotype is theoretically a risk factor for the development of DHF, since the majority of patients that exhibit DHF have been previously exposed to at least one of the other four serotypes of dengue virus.

To date, there is no specific treatment for dengue disease. Treatment for dengue disease is symptomatic, with bed rest, control of the fever and pain through antipyretics and analgesics, and adequate drinking. The treatment of DHF requires balancing of liquid losses, replacement of coagulation factors and the infusion of heparin.

Since dengue prevention measures, such as mosquito control and personal protection from bites are limited in efficacy, difficult to enforce and expensive, a safe and efficacious dengue vaccine would be the best mode of prevention. However, there is no licensed vaccine of this type that is currently available. It is therefore desirable to develop a vaccine composition that is useful in a method of protecting a human subject against each of the four serotypes of dengue virus.

SUMMARY OF THE INVENTION

The present invention relates to a vaccine composition for use in a method of protecting a human subject against dengue disease caused by a dengue virus of serotype 2, wherein said composition comprises:

(i) a dengue antigen of each of serotypes 1 to 4, wherein said dengue antigens of serotypes 1 to 4 are each independently selected from the group consisting of:

(a) a live attenuated dengue virus; and (b) a live attenuated chimeric dengue virus;

or (ii) a nucleic acid construct or constructs which are able to express in said human subject a dengue antigen of each of serotypes 1 to 4, wherein said dengue antigens are dengue VLPs.

The present invention further relates to the use of a vaccine composition, as defined herein, for the manufacture of a medicament for protecting a human subject against dengue disease caused by a dengue virus of serotype 2. Preferably said protection is also demonstrated in respect of dengue disease caused by a dengue virus of serotype 1, a dengue virus of serotype 3 and a dengue virus of serotype 4.

The present invention further relates to a method of protecting a human subject against dengue disease caused by a dengue virus of serotype 2, wherein said method comprises administering to said human subject an effective amount of a vaccine composition as defined herein. Preferably said method also protects against dengue disease caused by a dengue virus of serotype 1, a dengue virus of serotype 3 and a dengue virus of serotype 4.

Additionally, the present invention relates to a kit comprising a vaccine composition, as defined herein, and instructions for the use of said composition in a method of protecting a human subject against dengue disease caused by a dengue virus of serotype 2. Preferably said method also protects against dengue disease caused by a dengue virus of serotype 1, a dengue virus of serotype 3 and a dengue virus of serotype 4.

DEFINITIONS

Figure 1:
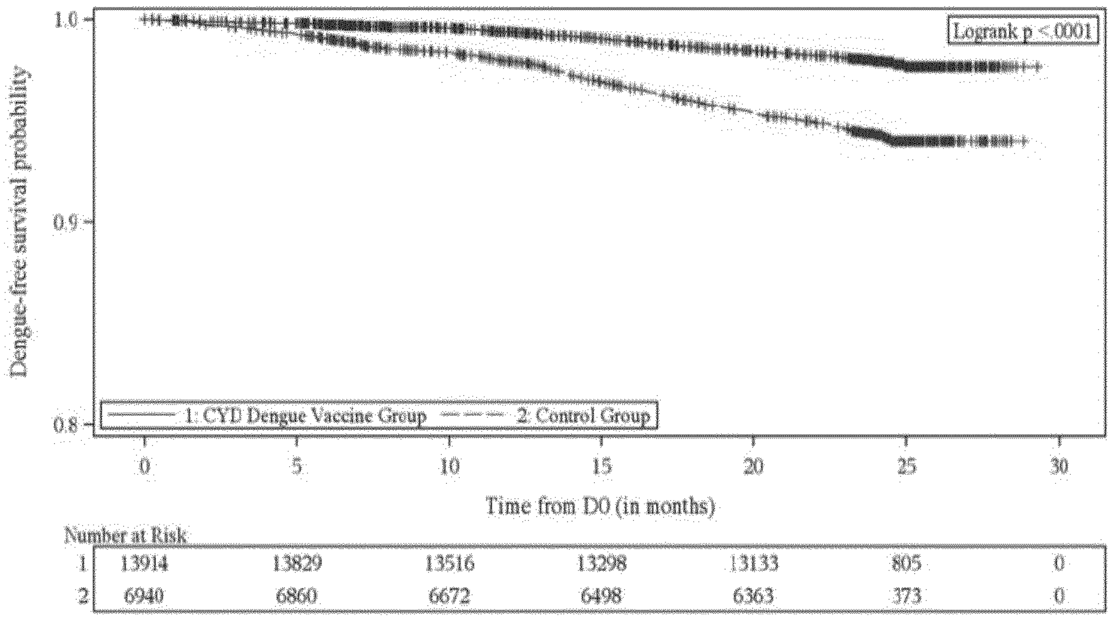
FIG. 1 is a Kaplan-Meier curve for symptomatic virologically-confirmed dengue (VCD) due to any serotype taking place at any time during the trial (described in Example 1) from day 0 in the Intention to Treat (ITT) population. The upper of the two lines represents the vaccine group and the lower of the two lines represents the control group.
Figure 2:
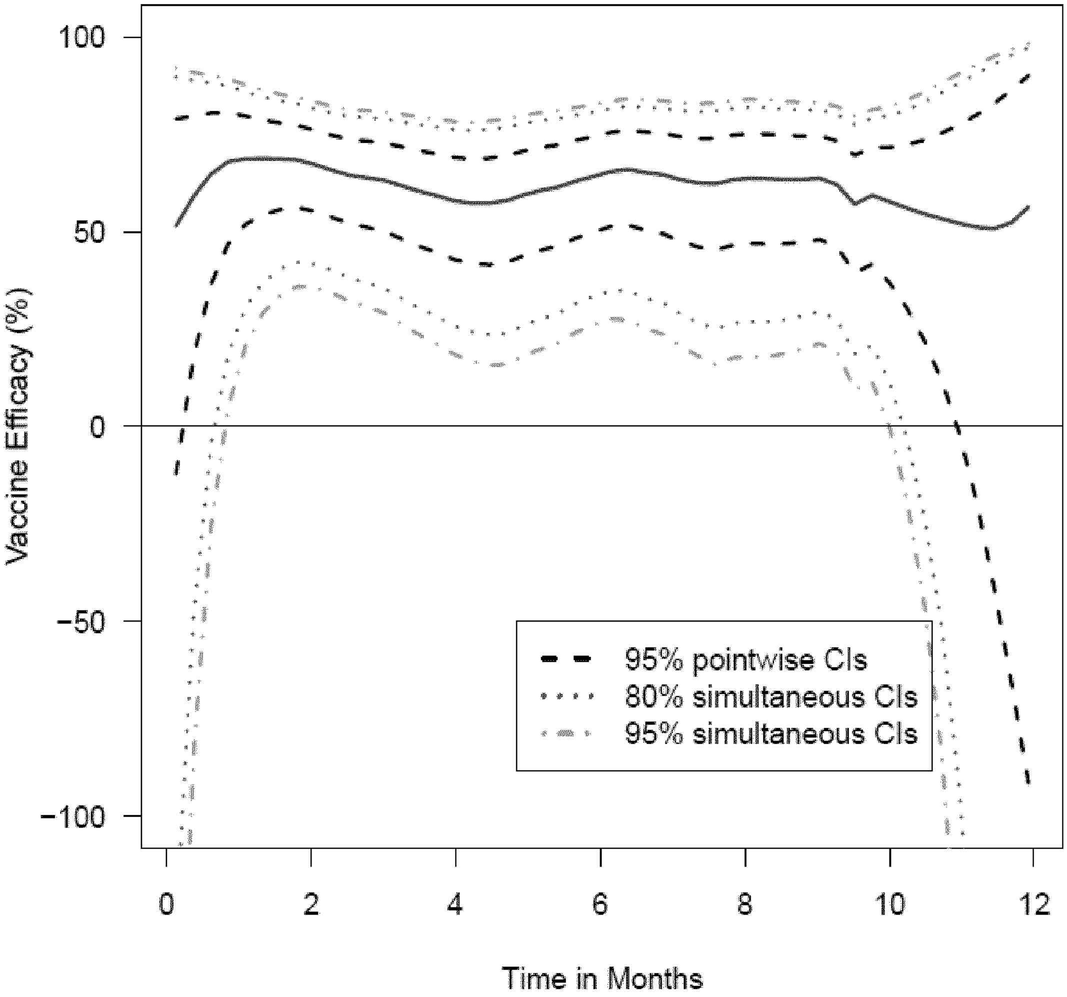
FIG. 2 shows the overall vaccine efficacy (all serotypes) over the 12 month period post dose 3 (solid line).

The term "dengue disease", as used herein, refers to the clinical symptoms, of all grades of severity, exhibited by an individual following infection by a dengue virus. As used herein, the term dengue disease encompasses both the milder manifestations of dengue disease such as dengue fever and the more severe manifestations of dengue fever such as severe dengue as defined herein or dengue haemorrhagic fever (DHF) as defined herein. Since 1975, clinical dengue has been classified according to World Health Organization guidelines (updated in 1997) as (i) dengue fever or (ii) dengue haemorrhagic fever (World Health Organization. Dengue hemorrhagic fever: Diagnosis, treatment, prevention and control $2^{nd}$ Ed. Geneva: WHO, 1997; ISBN 92 4 154500 3). In 2009, the WHO issued new guidelines that classify clinical dengue as (i) dengue with or without warning signs or (ii) severe dengue. Both classifications are shown in FIGS. 1 & 2 of Srikiatkachorn et al., Clin. Infect. Dis. (2011) 53(6): 563. According to the earlier 1997 WHO classification, dengue fever is diagnosed by: (i) the presence of fever with at least two symptoms selected from headache, arthralgia, retro-orbital pain, rash, myalgia, haemorrhagic manifestations, and leucopenia; together with (ii) supportive serology or occurrence at the same location and time as other confirmed dengue cases. Progression to Dengue haemorrhagic fever is confirmed when fever, haemorrhagic manifestations, thrombocytopenia and evidence of plasma leakage are all observed. According to the 2009 WHO classification, diagnosis of dengue requires the presence of: (i) fever and at least two clinical symptoms selected from nausea, vomiting, rash, aches and pains, a positive tourniquet test, or any warning signs selected from abdominal pain and tenderness, persistent vomiting, clinical fluid accumulation, mucosal bleed, lethargy or restlessness, liver enlargement >2 cm or an increase in haematocrit concurrent with a rapid decrease in platelet count; together with (ii) supportive serology or occurrence at the same location and time as other confirmed dengue cases. According to the 2009 WHO classification, severe dengue is defined as a diagnosis of dengue with the observation of any of the following additional events: (i) severe plasma leakage leading to shock or respiratory distress (fluid accumulation); (ii) severe bleeding as evaluated by clinicians; or (iii) severe organ involvement (i.e. liver: AST, ALT≥1000; CNS: impaired consciousness or heart or other organs).

The terms "Dengue haemorrhagic fever" or "DHF", as used herein, are consistent with the 1997 WHO definition and refer to the following symptoms—1) Clinical manifestations: (a) Fever: acute onset, high 38° C.) and continuous lasting 2 to 7 days; (b) Any of the following haemorrhagic manifestations: a positive tourniquet test, petechiae, purpura, ecchymosis, epitaxis, gum bleeding, and hematesis and/or melena; 2) Laboratory findings: (a) Thrombocytopenia (platelet count $\leq 100 \times 10^9$/L); (b) Plasma leakage as shown by hemoconcentration (haematocrit increased by 20% or more) or pleural effusion (seen on chest X-ray) and/or ascites and/or hypoalbuminemia. The first two clinical criteria (i.e. fever and haemorrhagic manifestations), plus thrombocytopenia and signs of plasma leakage are sufficient to establish a clinical diagnosis of DHF. Pleural effusion (seen on chest X-ray) and/or hypoalbuminemia provide supporting evidence of plasma leakage. DHF, as used herein, may be further defined on the basis of its severity. Thus DHF may be defined as being of Grade I, Grade II, Grade III or Grade IV (World Health Organization. Dengue hemorrhagic fever: Diagnosis, treatment, prevention and control $2^{nd}$ Ed. Geneva: WHO, 1997; ISBN 92 4 154500 3). Grade I is defined as fever accompanied by non-specific constitutional symptoms; the only haemorrhagic manifestation is a positive tourniquet test. Grade II is defined as spontaneous bleeding in addition to the manifestations of Grade I patients, usually in the form of skin or other haemorrhages. Grade III is defined as circulatory failure manifested by a rapid, weak pulse and narrowing of pulse pressure (20 mmHg or less) or hypotension, with the presence of cold clammy skin and restlessness. Grade IV is defined as profound shock with undetectable blood pressure and pulse. As would be understood by a person of skill in the art, in the practice of the present invention, e.g. a method of protecting against DHF, said DHF need not be virologically-confirmed.

The term "virologically-confirmed dengue", as used herein, refers to an acute febrile episode (i.e. temperature ≥38° C. on at least two consecutive days) which is confirmed to be induced by a dengue virus, e.g. by reverse transcriptase polymerase chain reaction (RT-PCR) and/or by a dengue non-structural 1 (NS1) protein enzyme-linked immunosorbent assay (ELISA). In the RT-PCR method, RNA is extracted from the serum to discard potential Taq polymerase inhibitors or interfering factors, using a commercial kit. Then a dengue screen RT-PCR reaction is carried out with primers from a gene sequence conserved among dengue viruses. Results are expressed as a concentration of $\log_{10}$ plaque forming unit (PFU)/mL, by comparison with standards containing known concentrations of viral genomic nucleic acid sequences. Serotype identification of post-infectious dengue viremia is determined by testing serum samples with the Simplexa™ Dengue RT-PCR assay (Focus Diagnostics, Inc. CA, USA). Briefly, RNA is extracted from the serum to discard potential polymerase inhibitors or interfering factors, using a commercial kit. Then the Simplexa™ assay is carried out which incorporates serotype-specific primers from dengue sequences. The results are expressed qualitatively and reported for each dengue serotype as detected or not detected. The Simplexa™ assay is used on all dengue screen RT-PCR positive or dengue NS1 Ag ELISA positive samples for serotype identification. The NS1 ELISA is performed using a commercially available kit (Platelia™ Dengue NS1 Ag, Bio-Rad, Marnes-la-Coquette, France). The manufacturer's instructions are followed. The Dengue NS1 Ag test is a one-step sandwich-ELISA based assay that enables detection of NS1 Ag in serum. The test uses murine monoclonal Abs (MAbs) for capture and revelation. Samples and controls are directly and simultaneously incubated with the conjugate within the microplate wells coated with MAb. If NS1 Ag is present in the sample, an immune-complex MAb-NS1-MAb/peroxidase will be formed. The presence of immune-complex is demonstrated by addition of a chromogenic solution that initiates a colour development reaction. After 30 minutes of incubation at room temperature, the enzymatic reaction is stopped by addition of an acid solution. The optical density (OD) reading obtained with a spectrophotometer set at 450/620 nm is proportional to the amount of NS1 Ag present in the sample. The presence of NS1 Ag in an individual sample is determined by comparing the OD reading of the sample to the OD of the cut-off control serum. Sample ratios of $<0.5$, $\geq 0.5$ to $<1.0$, and $\geq 1$ are indicative of negative, equivocal, and positive results, respectively.

The terms "severe dengue" or "severe dengue disease", as used herein refer to severe dengue as defined by the Independent Data Monitoring Committee (IDMC) established to oversee the Phase III clinical trials reported herein. According to the IDMC definition, in a case of dengue fever, the appearance of any one of the following criteria results in a diagnosis of severe dengue: (i) Shock (pulse pressure $\leq 20$ mmHg in a child or adolescent, or hypotension [$\leq 90$ mmHg] with tachycardia, weak pulse and poor perfusion); (ii) Bleeding requiring blood transfusion; (iii) Encephalopathy i.e., unconsciousness or poor conscious state or convulsions not attributable to simple febrile convulsion or focal neurological signs. Poor conscious state or unconsciousness must be supported by Glasgow Coma Scale (GCS) score; (iv) Liver impairment (AST>1000 U/L or prothrombin time [PT] International normalized ratio [INR]>1.5); (v) Impaired kidney function (Serum creatinine $\geq 1.5$ mg/dL) or (vi) Myocarditis, pericarditis or heart failure (clinical heart failure) supported by chest X ray (CXR), echocardiography, electrocardiogram (ECG) or cardiac enzymes where these are available. As would be understood by a person of skill in the art, in the practice of the present invention, e.g. a method of protecting against severe dengue, said severe dengue need not be virologically-confirmed and may simply occur in the same location as other virologically-confirmed cases of dengue disease.

The terms "dengue fever virus", "dengue virus" and "DEN" are used interchangeably. They refer to positive single-strand RNA viruses belonging to the Flavivirus genus of the family of flaviviridae. There are four different serotypes of dengue virus (serotypes 1, 2, 3 and 4), which possess approximately 60-80% sequence homology. The organization of the genome comprises the following elements: a 5' non-coding region (NCR), a region encoding structural proteins (capsid (C), pre-membrane (prM) and envelope (E)) and a region encoding non-structural proteins (NS1-NS2A-NS2B-NS3-NS4A-NS4B-NS5) and a 3' NCR. The dengue viral genome encodes an uninterrupted coding region which is translated into a single polyprotein which undergoes post-translational processing.

The term "live attenuated dengue virus", as used herein, refers to a live dengue virus derived from a virulent wild-type dengue virus by genetic modification resulting in attenuation of virulence and an inability to induce a disease state characterised by the same sets of symptoms associated with the corresponding wild type dengue virus. A live attenuated dengue virus may be prepared from a wild type virus, for example, by recombinant nucleic acid technology, site directed mutagenesis, serial passages on replication competent cells, chemical mutagenesis, electromagnetic radiation or genetic manipulation such as the deletion of a small section of the viral nucleic acid. Examples of live attenuated dengue viruses useful in the practice of the present invention include VDV1 (WO 2006/134433), VDV2 (WO 2006/134443), and the strains described for example in applications WO 02/066621, WO 00/57904, WO 00/57908, WO 00/57909, WO 00/57910, WO 02/0950075 and WO 02/102828. Live attenuated dengue viruses of serotype 1 which may be used as the dengue antigen of serotype 1 in the method of the invention include LAV1 and VDV1. Live attenuated dengue viruses of serotype 2 which may be used as the dengue antigen of serotype 2 in the method of the invention include LAV2 and VDV2. The term "VDV" designates a live attenuated dengue virus capable of replication in Vero cells and capable of inducing a specific humoral response, including the induction of neutralizing antibodies, in a human.

The live attenuated dengue virus of serotype 1 known as 16007/PDK13, also called "LAV1", was derived from the wild-type DEN-1 (dengue virus serotype 1) 16007 strain by submitting the wild type strain to 13 passages through primary dog kidney (PDK) cells. LAV1 has been described in EP1159968 and has been filed with the National Microorganisms Cultures Collection (CNCM, Institut Pasteur, Paris, France) under number 1-2480. "VDV1" is a virus derived from LAV1 by subsequent adaptation to Vero cells; in this regard, the RNA from LAV1 has been extracted and purified before being transfected into Vero cells. The VDV1 strain has subsequently been obtained by plate purification and amplification in Vero cells. The VDV1 strain has 3 additional mutations in comparison with the DEN-1 16007/PDK13 strain. The complete nucleotide sequence of the VDV1 strain, as well as a process for preparing and characterizing the VDV1 strain have been described in international patent publication WO 2006/134433. The complete nucleic acid sequence of the VDV1 strain is as set forth in SEQ ID NO: 6.

The live attenuated dengue virus of serotype 2 known as 16681/PDK53, also called "LAV2", has been obtained from the wild-type DEN-2 (dengue virus serotype 2) 16681 strain by submitting the wild type strain to 53 passes through PDK cells. LAV2 has been described in EP1159968 and has been filed with the National Microorganisms Cultures Collection (CNCM, Institut Pasteur, Paris, France) under number 1-2481. "VDV2" is a strain derived from LAV2 by subsequent adaptation to Vero cells; in this regard, the RNA from LAV2 has been extracted and purified before being transfected in Vero cells. The VDV2 strain has subsequently been obtained by plate purification and amplification in Vero cells. The VDV2 strain has 10 additional mutations in comparison with the 16681/PDK53 strain, including 3 silent mutations and 1 mutation in a non-coding region. The complete nucleotide sequence of the VDV2 strain, as well as a process for preparing and characterizing the VDV2 strain have been described in the international patent publication WO 2006/134443. The complete nucleic acid sequence of the VDV2 strain is as set forth in SEQ ID NO: 7.

In the context of the invention, "dengue chimera" or "chimeric dengue virus" means a recipient flavivirus in which the genetic backbone has been modified by exchanging the sequence of at least the E protein of the recipient flavivirus by the corresponding sequence of a dengue virus. Alternatively, and more preferably, the genetic backbone of the recipient flavivirus is modified by exchanging the nucleic acid sequences encoding both the prM and E proteins of the recipient flavivirus by the corresponding sequences of a dengue virus. Typically, the recipient flavivirus may be attenuated. The recipient flavivirus may be a yellow fever (YF) virus, in which case, the chimera is referred to herein as a "chimeric YF/dengue virus". Preferably, the YF backbone of a chimeric YF/dengue virus according to the present invention is from an attenuated YF virus. The recipient flavivirus may also be a dengue virus and in that case, the chimeric dengue virus is referred to herein as a "chimeric dengue/dengue virus", the dengue virus serotype characteristic of the E or the prM and E proteins being identical or different from the recipient dengue virus serotype characteristic of the genetic backbone. When the recipient flavivirus is a dengue virus, said dengue virus is preferably attenuated. When the serotypes of the recipient and donor dengue viruses are identical, the recipient dengue virus and the donor dengue virus from which the prM and E protein encoding sequences originate are two different virus strains of the same serotype. For use in the present invention, chimeric dengue viruses are typically chimeric YF/dengue viruses.

In one embodiment, the chimeric YF/dengue virus comprises the genomic backbone of the attenuated yellow fever virus strain YF17D (Theiler M. and Smith H. H., 1937, J. Exp. Med., 65. 767-786). Examples of other attenuated YF strains which may be used include YF17D204 (YF-VAX®, Sanofi-Pasteur, Swiftwater, Pa., USA; Stamaril®, Sanofi-Pasteur, Marcy l'Etoile, France; ARILVAX™, Chiron, Speke, Liverpool, UK; FLAVIMUN®, Berna Biotech, Bern, Switzerland; YF17D-204 France (X15067, X15062); YF17D-204,234 US (Rice et al., 1985, Science, 229: 726-733), or the related strains YF17DD (Genbank access number U17066), YF17D-213 (Genbank access number U17067) and the strains YF17DD described by Galler et al. (1998, Vaccines, 16(9/10): 1024-1028). Advantageously, the recipient flavivirus of a live attenuated chimeric YF/dengue virus of the present invention is YF 17D or YF 17D204.

Examples of chimeric dengue viruses useful in the practice of the present invention include the chimeric YF/dengue viruses described in patent application WO 98/37911 and the chimeric dengue/dengue viruses such as those described in patent applications WO 96/40933 and WO 01/60847.

One example of a chimeric YF/dengue virus particularly suitable for use in the practice of the present invention is a Chimerivax® YF/dengue virus, which is also referred to herein as a "CYD" virus. As used herein, a Chimerivax® YF/dengue (or CYD) virus is a live attenuated chimeric YF/dengue virus which comprises the genomic backbone of a suitable attenuated YF virus (e.g. YF17D or YF17D204 (YF-VAX®)) in which the nucleic acid sequences encoding the pre-membrane (prM) and envelope (E) proteins have been replaced by nucleic acid sequences encoding the corresponding structural proteins of a dengue virus. Construction of such Chimerivax® viruses may be achieved in accordance with, or in substantial accordance with, the teaching of Chambers, et al. (1999, J. Virology 73(4): 3095-3101). The particular Chimerivax® (CYD) viruses described in the examples have been generated by using prM and E sequences from strains DEN 1 PUO 359 (TVP1 140), DEN2 PUO 218, DEN3 PaH881/88 and DEN 4 1228 (TVP 980). For convenience, the particular Chimerivax® (CYD) viruses described in the examples are referred to herein as "CYD1", "CYD2", "CYD3" and "CYD4". The preparation of these particular strains has been described in detail in international patent applications WO 98/37911, WO 03/101397, WO 07/021672, WO 08/007021, WO 08/047023 and WO 08/065315, to which reference may be made for a precise description of the processes for their preparation. The SEQ ID NOs corresponding to the nucleotide sequences of the prM-E regions of CYD1, CYD2, CYD3 and CYD4 are set out in Table 16. Alternatively, other dengue fever virus strains may be used as a source of nucleic acids to facilitate construction of chimeric viruses useful in the practice of the present invention, as described elsewhere herein, for example in the construction of other Chimerivax® YF/Dengue viruses. An alternative embodiment of chimeric dengue virus usable in the method of protection of the invention is a recipient flavivirus in which the genetic backbone has been modified by exchanging (i) the sequence encoding the E protein of the recipient flavivirus by the corresponding sequence of a dengue virus and (ii) the sequence encoding the prM protein of the recipient flavivirus by the corresponding sequence of a non-dengue flavivirus, e.g. a JEV virus. Examples of such chimeric dengue viruses are described in WO 2011/138586.

The term "dengue virus-like particle" or "dengue VLP", as used herein, refers to a virus particle that does not contain replicative genetic material but presents at its surface a dengue E protein in a repetitive ordered array similar to the native virion structure. Typically, dengue VLPs also contain dengue prM and/or M proteins. VLPs may be produced in vitro (Zhang et al, J. Virol. (2011) 30 (8):333). VLPs may also be produced in vivo. To that end, a nucleic acid construct or constructs (e.g. DNA or RNA) encoding prM/M and E dengue proteins may be introduced into a cell of a subject, e.g. a human subject, via methods known in the art, e.g. via use of at least one viral vector. The VLP particles are then formed in vivo. Non-limiting examples of viral vectors that may be used in the method of the present invention include the poxviruses (e.g. the attenuated pox Ankara virus) and the measles virus. For use in the present invention, a particular category of viral vector expressing VLPs in vivo includes replication-deficient pseudoinfectious (PIV) viruses, e.g. according to the Replivax™ technology. (Rumyantsev A A, et al. Vaccine. 2011 Jul. 18; 29(32):5184-94).

The ability of a vaccine composition of the present invention to provoke an immune response in a subject (i.e. induce the production of neutralizing antibodies) can be assessed, for example, by measuring the neutralizing antibody titre raised against the dengue virus serotype(s) comprised within the composition. The neutralizing antibody titre may be measured by the Plaque Reduction Neutralization Test ($PRNT_{50}$) test (Timiryasova, T. M. et al., Am. J.

Trop. Med. Hyg. (2013), vol. 88(5), 962-970). Briefly, neutralizing antibody titre is measured in sera collected from subjects to be tested for their level of dengue neutralising antibodies. If the subject is a vaccinated subject, a sample is collected from said subject at least 28 days following administration of a vaccine composition of the present invention. Serial, two-fold dilutions of the sera (previously heat-inactivated) are mixed with a constant challenge-dose of each dengue virus of serotype 1, 2, 3 or 4 as appropriate (expressed as PFU/mL). The parental dengue virus strains of the CYD dengue vaccine constructs are used as the challenge strains. The mixtures are then inoculated into wells of a microplate with confluent Vero cell monolayers. After adsorption, cell monolayers are incubated for a few days. The presence of dengue virus infected cells is indicated by the formation of infected foci (i.e. plaques) and a reduction in virus infectivity due to the presence of neutralising antibodies in the serum samples (i.e. a reduction in the number of plaques) can thus be detected. The reported value (end point neutralization titre) represents the highest dilution of serum at which ≥50% of dengue challenge virus (in plaque counts) is neutralized when compared to the mean viral plaque count in the negative control wells (which represents the 100% virus load). The end point neutralization titres are presented as continuous values. The lower limit of quantification (LLOQ) of the assay is 10 (1/dil). It has been commonly considered that seroconversion occurs when the titre is superior or equal to 10 (1/dil). As PRNT tests may slightly vary from a laboratory to another the LLOQ may also slightly vary. Accordingly, in a general manner, it is considered that seroconversion occurs when the titre is superior or equal to the LLOQ of the test. Neutralising antibody titres were considered in the following references, but the authors did not establish a correlate of protection (Guirakhoo et al, J. Virol. (2004) 78 (9): 4761; Libraty et al, PLoS Medicine (2009) 6 (10); Gunther et al, Vaccine (2011) 29: 3895) and Endy et al, J. Infect. Dis. (2004), 189(6): 990-1000).

The term "$CCID_{50}$" refers to the quantity of virus (e.g. vaccinal virus) infecting 50% of the cell culture. The $CCID_{50}$ assay is a limit dilution assay with statistical titer calculation (Morrison D et al, *J Infect Dis*. 2010; 201(3): 370-7)).

As used herein, a "dengue naïve" subject refers to a subject who has not been infected by a dengue virus nor previously immunized with a dengue vaccine, i.e. a serum sample taken from said subject will produce a negative result in a dengue ELISA or PRNT50 assay.

As used herein, a "dengue immune" subject refers to a subject who has been infected by a dengue virus or immunized by a dengue vaccine before administration of the vaccine composition of the present invention, i.e. a serum sample taken from said subject will produce a positive result in a dengue ELISA or PRNT50 assay.

In accordance with the present invention, a "method of protecting", as used herein, results in a reduction in the severity or in the likelihood of developing dengue disease in a human subject exposed to a dengue virus. Advantageously, said reduction is statistically significant. A method of protecting, according to the present invention, may result in any one or more of the following:

(i) a statistically significant reduction in the incidence or likelihood of, e.g. the prevention of dengue disease caused by a dengue virus of serotype 2;

(ii) a statistically significant reduction in the incidence or likelihood of, e.g. the prevention of, dengue disease caused by a dengue virus of serotype 1, dengue disease caused by a dengue virus of serotype 2, dengue disease caused by a dengue virus of serotype 3 and dengue disease caused by a dengue virus of serotype 4;

(iii) prevention of dengue disease, regardless of severity, caused by serotypes 1, 2, 3 and 4;

(iv) a statistically significant reduction in the incidence or likelihood of, e.g. the prevention of, severe dengue disease caused by a dengue virus of serotype 2;

(v) a statistically significant reduction in the incidence or likelihood of, e.g. the prevention of, severe dengue disease caused by a dengue virus of serotype 1, severe dengue disease caused by a dengue virus of serotype 2, severe dengue disease caused by a dengue virus of serotype 3 and severe dengue disease caused by a dengue virus of serotype 4;

(vi) a reduction in the incidence or likelihood of, e.g. the prevention of, DHF caused by a dengue virus of serotype 2; preferably said reduction is statistically significant;

(vii) a reduction in the incidence or likelihood of, e.g. the prevention of, DHF caused by a dengue virus of serotype 1, DHF caused by a dengue virus of serotype 2, DHF caused by a dengue virus of serotype 3 and DHF caused by a dengue virus of serotype 4; preferably said reduction is statistically significant;

(viii) a statistically significant reduction in the incidence or likelihood of, e.g. the prevention of, hospitalization due to dengue disease caused by a dengue virus of serotype 2;

(ix) a statistically significant reduction in the incidence or likelihood of, e.g. the prevention of, hospitalization due to: dengue disease caused by a dengue virus of serotype 1; dengue disease caused by a dengue virus of serotype 2; dengue disease caused by a dengue virus of serotype 3 and dengue disease caused by a dengue virus of serotype 4;

(x) a statistically significant reduction in the incidence or likelihood, e.g. the prevention of, repeated symptomatic virologically-confirmed dengue cases due to any serotype, defined as ≥2 episodes of dengue due to different serotypes occurring more than 14 days apart.

(xi) any one of (i) to (x) in human subjects who are at least 5 years of age;

(xii) any one of (i) to (x) in human subjects who are at least 7 years of age;

(xiii) any one of (i) to (x) in human subjects who are at least 9 years of age;

(xiv) any one of (i) to (x) in human subjects who are at least 12 years of age;

(xv) any one of (i) to (x) in human subjects who are between 9 and 16 years of age;

(xvi) any one of (i) to (x) in human subjects who are between 12 and 16 years of age;

(xvii) prevention of dengue disease caused by dengue virus serotypes 1, 2, 3 and 4 in individuals 9 through 60 years of age living in endemic areas;

(xviii) prevention of dengue disease caused by dengue virus serotypes 1, 2, 3 and 4 in individuals 12 through 60 years of age living in endemic areas;

(xix) any one of (i) to (xviii), wherein said dengue virus of serotype 2 has an American, Asian/American or Cosmopolitan genotype.

Overview of the Present Invention

The present invention relates to a vaccine composition for use in a method of protecting a human subject against dengue disease caused by a dengue virus of serotype 2, wherein said composition comprises:

(i) a dengue antigen of each of serotypes 1 to 4, wherein said dengue antigens of serotypes 1 to 4 are each independently selected from the group consisting of:
(a) a live attenuated dengue virus; and
(b) a live attenuated chimeric dengue virus;

or (ii) a nucleic acid construct or constructs which are able to express in said human subject a dengue antigen of each of serotypes 1 to 4, wherein said dengue antigens are dengue VLPs.

Preferably, said dengue disease caused by a dengue virus of serotype 2 is severe dengue disease. Preferably, said method results in a reduction in the incidence or likelihood of hospitalisation due to dengue disease caused by a dengue virus of serotype 2. Preferably, said dengue disease caused by a dengue virus of serotype 2 is DHF.

Preferably, said method also protects said human subject against dengue disease caused by a dengue virus of serotype 1, dengue disease caused by a dengue virus of serotype 3 and dengue disease caused by a dengue virus of serotype 4. Preferably, said method results in a reduction in the incidence or likelihood of hospitalisation due to: dengue disease caused by a dengue virus of serotype 1; dengue disease caused by a dengue virus of serotype 2; dengue disease caused by a dengue virus of serotype 3 and dengue disease caused by a dengue virus of serotype 4. Preferably, when a vaccine composition of the present invention is used in a method as described herein, said method results in a protection of said human subject against dengue fever caused by a dengue virus of serotype 1, dengue fever caused by a dengue virus of serotype 2, dengue fever caused by a dengue virus of serotype 3 and dengue fever caused by a dengue virus of serotype 4. Preferably, when a vaccine composition of the present invention is used in a method as described herein, said method results in protection of said human subject against severe dengue disease caused by a dengue virus of serotype 1, severe dengue disease caused by a dengue virus of serotype 2, severe dengue disease caused by a dengue virus of serotype 3 and severe dengue disease caused by a dengue virus of serotype 4. Preferably, when a vaccine composition of the present invention is used in a method as described herein, said method results in protection of said human subject against DHF caused by a dengue virus of serotype 1, DHF caused by a dengue virus of serotype 2, DHF caused by a dengue virus of serotype 3 and DHF caused by a dengue virus of serotype 4.

Preferably a vaccine composition of the present invention is administered to a human subject who is dengue immune. Preferably a vaccine composition of the present invention is administered to a human subject who is at least 2 years old. Preferably said human subject is at least 5 years old. Preferably said human subject is at least 7 years old. Preferably said human subject is at least 9 years old. Preferably said human subject is at least 12 years old. Preferably said human subject is aged between 2 and 60 years old. Preferably said human subject is aged between 6 and 60 years old. Preferably said human subject is aged between 7 and 60 years old. Preferably said human subject is aged between 9 and 60 years old. Preferably said human subject is aged between 12 and 60 years old. Preferably said human subject is aged between 2 and 16 years old. Preferably said human subject is aged between 5 and 16 years old. Preferably said human subject is aged between 9 and 16 years old.

A human subject according to the present invention is preferably not pregnant, lactating or of childbearing potential, does not have self-reported or suspected congenital or acquired immunodeficiency, has not been in receipt of immunosuppressive therapy within the 6 months prior to vaccination or systemic corticosteroids therapy for more than 2 weeks within the 3 months prior to vaccination, is not HIV seropositive and does not have systemic hypersensitivity to any of the vaccine components as defined herein.

Preferably a vaccine composition according to the present invention comprises a dengue antigen of each of serotypes 1 to 4 which are each independently selected from the group consisting of: (a) a live attenuated dengue virus and (b) a live attenuated chimeric virus.

Preferably a vaccine composition according to the present invention comprises a dengue antigen of each of serotypes 1 to 4, wherein said dengue antigens of serotypes 1, 3 and 4 are each a live attenuated chimeric dengue virus and said dengue antigen of serotype 2 is selected from the group consisting of a live attenuated dengue virus and a live attenuated chimeric dengue virus. For example, a vaccine composition of the present invention may comprise a dengue antigen of each of serotypes 1 to 4, wherein said dengue antigens of serotypes 1, 3 and 4 are each a live attenuated chimeric dengue/dengue virus and said dengue antigen of serotype 2 is a live attenuated dengue virus. For example, a vaccine composition according to the present invention may be the tetravalent mixture of dengue antigens of each of serotypes 1 to 4 (referred to as DENVax) which is disclosed in Huang et al., PLoS Negl Trop Dis 7(5): e2243 (2013). Alternatively, a vaccine composition of the present invention may comprise a dengue antigen of each of serotypes 1 to 4, wherein said dengue antigens of serotypes 1, 3 and 4 are each a live attenuated chimeric YF/dengue virus and said dengue antigen of serotype 2 is a live attenuated dengue virus.

Preferably a vaccine composition according to the present invention comprises a dengue antigen of each of serotypes 1 to 4, wherein said dengue antigens of serotypes 1, 3 and 4 are each independently selected from the group consisting of: (a) a live attenuated dengue virus and (b) a live attenuated chimeric dengue virus and said dengue antigen of serotype 2 is a live attenuated chimeric dengue virus. For example, a vaccine composition of the present invention may comprise a dengue antigen of each of serotypes 1 to 4, wherein said dengue antigens of serotypes 1, 3 and 4 are each a live attenuated dengue virus and said dengue antigen of serotype 2 is a live attenuated chimeric dengue/dengue virus. For example, a vaccine composition according to the present invention may be any of the tetravalent mixtures of dengue antigens of each of serotypes 1 to 4 (referred to as TV001, TV002, TV003 and TV004') which are disclosed in Durbin et al., Journal of Infectious Diseases (2013), 207, 957-965. Preferably, a vaccine composition according to this embodiment of the invention is TV003.

Preferably a vaccine composition according to the present invention comprises a dengue antigen of each of serotypes 1 to 4, wherein each of said dengue antigens is a live attenuated chimeric dengue virus, preferably a chimeric YF/dengue virus, more preferably a chimeric YF/dengue virus which comprises an attenuated YF genomic backbone whose prM-E sequence has been substituted with the prM-E sequence of dengue virus.

Preferably, a live attenuated chimeric dengue virus of the present invention comprises one or more proteins from a dengue virus and one or more proteins from a different flavivirus. Preferably, the different flavivirus is an yellow fever virus (i.e. a chimeric YF/dengue virus). Preferably a live attenuated chimeric dengue virus according to the present invention comprises an attenuated yellow fever virus genome whose prM-E sequence has been substituted with the prM-E sequence of a dengue virus. Alternatively, a live attenuated chimeric dengue virus of the present invention comprises one or more proteins from a first dengue virus and one or more proteins from a second dengue virus (i.e. a chimeric dengue/dengue virus). Preferably said first dengue virus and said second dengue virus are of different serotypes. Where said first dengue virus and said second dengue virus are of the same serotype, said first and second dengue viruses are different strains.

A preferred example of a dengue antigen of serotype 1 for use in the present invention is a live attenuated chimeric YF/dengue virus which comprises a nucleotide sequence having at least 90%, at least 95%, at least 98% or 100% sequence identity to SEQ ID NO: 1. Another preferred example of a dengue antigen of serotype 1 for use in the present invention is a live attenuated dengue virus which comprises a nucleotide sequence having at least 90%, at least 95%, at least 98% or 100% sequence identity to SEQ ID NO: 6. Preferably a nucleotide sequence that has less than 100% identity to SEQ ID NO: 6 does not comprise mutations at the positions within said nucleic acid sequence which correspond to positions 1323, 1541, 1543, 1545, 1567, 1608, 2363, 2695, 2782, 5063, 5962, 6048, 6806, 7330, 7947 and 9445 of SEQ ID NO: 6.

A preferred example of a dengue antigen of serotype 2 for use in the present invention is a live attenuated chimeric YF/dengue virus which comprises a nucleotide sequence having at least 90%, at least 95%, at least 98% or 100% sequence identity to SEQ ID NO: 2. Another preferred example of a dengue antigen of serotype 2 for use in the present invention is a live attenuated chimeric YF/dengue virus which comprises a nucleotide sequence having at least 90%, at least 95%, at least 98% or 100% sequence identity to SEQ ID NO: 5. Another preferred example of a dengue antigen of serotype 2 for use in the present invention is a live attenuated dengue virus which comprises a nucleotide sequence having at least 90%, at least 95%, at least 98% or 100% sequence identity to SEQ ID NO: 7. Preferably a nucleotide sequence that has less than 100% identity to SEQ ID NO: 7 does not comprise mutations at the positions within said nucleic acid sequence which correspond to positions 736, 1619, 4723, 5062, 9191, 10063, 10507, 57, 524, 2055, 2579, 4018, 5547, 6599 and 8571 of SEQ ID NO: 7.

A preferred example of a dengue antigen of serotype 3 for use in the present invention is a live attenuated chimeric YF/dengue virus which comprises a nucleotide sequence having at least 90%, at least 95%, at least 98% or 100% sequence identity to SEQ ID NO: 3.

A preferred example of a dengue antigen of serotype 4 for use in the present invention is a live attenuated chimeric YF/dengue virus which comprises a nucleotide sequence having at least 90%, at least 95%, at least 98% or 100% sequence identity to SEQ ID NO: 4.

In order to form a vaccine composition (in a tetravalent dosage form) according to the present invention (i.e. one containing a dengue antigen of each of serotypes 1 to 4), the preferred examples of dengue antigens of serotypes 1, 2, 3 and 4 disclosed in the preceding four paragraphs may be combined in any combination possible. Alternatively, a vaccine composition according to the present invention may be administered to a subject as two bivalent dosage forms, wherein the preferred examples of dengue antigens of serotypes 1, 2, 3 and 4 disclosed in the preceding four paragraphs may be combined in any pair of bivalent combinations that are possible. Thus, in particularly preferred combinations of dengue antigens of serotypes 1, 2, 3 and 4, the dengue antigens of serotypes 3 and 4 are respectively a live attenuated chimeric YF/dengue virus which comprises a nucleotide sequence having at least 90%, at least 95%, at least 98% or 100% sequence identity to SEQ ID NO: 3 and a live attenuated chimeric YF/dengue virus which comprises a nucleotide sequence having at least 90%, at least 95%, at least 98% or 100% sequence identity to SEQ ID NO: 4. In such particularly preferred combinations, the dengue antigens of serotypes 1 and 2 may respectively be:

(i) a live attenuated chimeric YF/dengue virus which comprises a nucleotide sequence having at least 90%, at least 95%, at least 98% or 100% sequence identity to SEQ ID NO: 1 and a live attenuated chimeric YF/dengue virus which comprises a nucleotide sequence having at least 90%, at least 95%, at least 98% or 100% sequence identity to SEQ ID NO: 2; or (ii) a live attenuated chimeric YF/dengue virus which comprises a nucleotide sequence having at least 90%, at least 95%, at least 98% or 100% sequence identity to SEQ ID NO: 1 and a live attenuated chimeric YF/dengue virus which comprises a nucleotide sequence having at least 90%, at least 95%, at least 98% or 100% sequence identity to SEQ ID NO: 5; or (iii) a live attenuated chimeric YF/dengue virus which comprises a nucleotide sequence having at least 90%, at least 95%, at least 98% or 100% sequence identity to SEQ ID NO: 1 and a live attenuated dengue virus which comprises a nucleotide sequence having at least 90%, at least 95%, at least 98% or 100% sequence identity to SEQ ID NO: 7 (preferably a nucleotide sequence that has less than 100% identity to SEQ ID NO: 7 does not comprise mutations at the positions within said nucleic acid sequence which correspond to positions 736, 1619, 4723, 5062, 9191, 10063, 10507, 57, 524, 2055, 2579, 4018, 5547, 6599 and 8571 of SEQ ID NO: 7); or (iv) a live attenuated dengue virus which comprises a nucleotide sequence having at least 90%, at least 95%, at least 98% or 100% sequence identity to SEQ ID NO: 6 (preferably a nucleotide sequence that has less than 100% identity to SEQ ID NO: 6 does not comprise mutations at the positions within said nucleic acid sequence which correspond to positions 1323, 1541, 1543, 1545, 1567, 1608, 2363, 2695, 2782, 5063, 5962, 6048, 6806, 7330, 7947 and 9445 of SEQ ID NO: 6 and a live attenuated dengue virus which comprises a nucleotide sequence having at least 90%, at least 95%, at least 98% or 100% sequence identity to SEQ ID NO: 7 (preferably a nucleotide sequence that has less than 100% identity to SEQ ID NO: 7 does not comprise mutations at the positions within said nucleic acid sequence which correspond to positions 736, 1619, 4723, 5062, 9191, 10063, 10507, 57, 524, 2055, 2579, 4018, 5547, 6599 and 8571 of SEQ ID NO: 7).

Preferably, a vaccine composition of the present invention results in a certain level of vaccine efficacy. For example, a vaccine composition of the present invention has a vaccine efficacy in respect of dengue disease caused by serotype 2 of at least 30%, more preferably at least 40%. For example, a vaccine composition of the present invention has an overall vaccine efficacy in respect of dengue disease (that is caused by any serotype) of at least 60%. For example, a vaccine composition of the present invention has a vaccine efficacy in respect of dengue disease caused by serotype 2 of at least 30%, more preferably at least 40% and an overall vaccine efficacy in respect of dengue disease (that is caused by any serotype) of at least 60%.

Preferably a vaccine composition of the present invention is administered to a human subject who is yellow fever immune. As used herein, a yellow fever immune subject refers to a subject who has been infected by a YF virus or immunized by a YF vaccine before administration of the vaccine composition of the present invention, i.e. a serum sample taken from said subject will produce a positive result in a YF ELISA or YF PRNT50 assay. Briefly, a YF PRNT50 assay is carried out as follows. Serial two-fold dilutions of serum to be tested (previously heat-inactivated) are mixed with a constant concentration of the YF vaccinal strain 17D (expressed as PFU/mL). The mixtures are inoculated in duplicate into wells of a plate of confluent Vero cells. After adsorption, cell monolayers are overlaid and incubated for a few days. The reported value (end point neutralization titer) represents the highest dilution of serum at which 50% of YF challenge virus (in plaque counts) is neutralized when compared to the negative control wells, which represents the 100% virus load. The LLOQ for the YF PRNT50 assay is 10 (1/dil). Alternatively and advantageously, a more stringent assay may be used to define a human subject who is yellow fever immune. For example, a YF immune subject may be defined as a subject whose serum sample produces a positive result in a PRNT80 or PRNT90 assay. The reported value (end point neutralization titer) represents the highest dilution of serum at which ≥80% or ≥90% of YF challenge virus (in plaque counts) is neutralized when compared to the negative control wells. Preferably a vaccine composition of the present invention is administered to a human subject who is yellow fever and dengue immune. Preferably a vaccine composition of the present invention is administered to a human subject who is multitypic dengue immune. As used herein, a multitypic dengue immune subject refers to a subject who has been infected by more than one serotype of dengue virus (either by natural infection or by vaccination). A multitypic dengue immune subject is defined as a subject who will produce a positive result (antibody titre >10) to at least two serotypes in a dengue PRNT50 assay and a less than six fold difference between the positive serotypes. A monotypic dengue immune subject is defined as a subject who will produce a positive result (antibody titre >10) to only one serotype in a dengue PRNT50 assay or a subject who has at least a six-fold higher response to a single serotype in a dengue PRNT50 assay compared to the response to the remaining three serotypes. Preferably a vaccine composition of the present invention is administered to a subject who is yellow fever immune and monotypic dengue immune. Preferably a vaccine composition of the present invention is administered to a human subject who is yellow fever immune and multitypic dengue immune.

A vaccine composition according to the present invention may be administered in multiple doses. For example, a vaccine composition according to the present invention may be administered in one, two or three doses. When a vaccine composition according to the present invention is administered in three doses, the first dose and the third dose are preferably administered approximately twelve months apart. For instance, a vaccine composition of the present invention may be administered in a first dose, a second dose and a third dose, wherein said second dose is to be administered about six months after said first dose and wherein said third dose is to be administered about twelve months after said first dose. Alternatively, the three doses may be administered at zero months, at about three to four months (e.g. at about three-and-a-half months) and at about twelve months (i.e. a regimen wherein the second dose of the composition is administered at about three-and-a-half months after the first dose, and wherein the third dose of the composition is administered at about twelve months after the first dose).

A vaccine composition according to the present invention may be administered in two doses. Preferably, the first dose and the second dose are administered approximately about three, six, eight or nine months apart. Preferably, the second dose is administered about six months after the first dose. Alternatively, two doses of a vaccine composition according to the present invention may be administered to a subject simultaneously or almost simultaneously (e.g. within 24 hours of each other). Preferably, when a vaccine composition according to the present invention is administered in two doses, the human subject to which the vaccine composition is administered is dengue immune. If said subject is dengue immune due to prior vaccination, said prior vaccination was preferably administered at least 3 months, more preferably at least 6 months prior to the first of the two doses of a vaccine composition according to the present invention.

A vaccine composition according to the present invention may be administered in a single dose. Preferably, when a vaccine composition according to the present invention is administered in a single dose, the human subject to which the vaccine composition is administered is dengue immune. If said subject is dengue immune due to prior vaccination, said prior vaccination was preferably administered at least 3 months, more preferably at least 6 months prior to the single dose of a vaccine composition according to the present invention.

Optionally, booster administrations of a vaccine composition according to the present invention may be used, for example between six months and ten years, for example six months, one year, three years, five years or ten years after initial immunization (i.e. after administration of the last dose scheduled in the initial immunization regimen).

A human subject according to the present invention (to which a vaccine composition of the present invention is administered) is preferably resident in or travelling to a dengue endemic area. More preferably, said human subject is resident in a dengue endemic area. A human subject according to the present invention may also be resident in an area that is experiencing a dengue epidemic. The term resident is given its conventional meaning herein and refers to a person who is normally domiciled in the area in question. Dengue endemic areas are well-known to a person of skill in the art and include, according to the present invention, most of the tropics and sub-tropics, for instance any country identified as an endemic country by the WHO. A dengue endemic area may be defined herein as an area in which the population is at least 50% dengue immune or at least 60% dengue immune. More preferably, a dengue endemic area may be defined as an area in which the population is at least 70% dengue immune, at least 80% dengue immune or at least 90% dengue immune. Accordingly, a human subject according to the present invention is preferably resident in a dengue endemic area, wherein the population of said area is at least 50%, at least 60%, at least 70%, at least 80% or at least 90% dengue immune. For instance, a dengue endemic area according to the present invention may comprise those American countries or parts thereof which fall within the tropics and sub-tropics. A dengue endemic area according to the present invention may thus comprise any one or more of the following countries or parts thereof: Brazil, Venezuela, Colombia, Ecuador, Peru, Bolivia, Paraguay, Panama, Costa Rica, Nicaragua, Honduras, El Salvador, Guatemala, Belize, Mexico, the USA and the islands of the Caribbean. In a particular embodiment, a dengue endemic area of the present invention may consist of the following: Brazil, Colombia, Honduras, Mexico and Puerto Rico. In another particular embodiment, a dengue endemic area of the present invention may consist of the following: Brazil, Colombia and Honduras. A dengue endemic area according to the present invention may also include south Asian and Oceania countries within the tropics and sub-tropics. A dengue endemic area according to the present invention may thus consist of any one or more of the following: India, Myanmar (Burma), Thailand, Laos, Viet Nam, Cambodia, Indonesia, Malaysia, Singapore, the Philippines, Taiwan, Papua New Guinea and Australia.

A human subject according to the present invention (to which a vaccine composition of the present invention is administered) is advantageously resident in a dengue endemic area in which the dominant circulating strains of dengue are of serotypes 1, 3 and 4. For example, at least 50%, at least 60%, at least 70%, at least 80% or at least 90% of the cases of dengue disease in said dengue endemic area are caused by a dengue virus of serotypes 1, 3 or 4. A human subject according to the present invention (to which a vaccine composition of the present invention is administered) is advantageously resident in a dengue endemic area in which the dominant circulating strains of dengue are of serotypes 3 and 4. For example, at least 50%, at least 60%, at least 70%, at least 80% or at least 90% of the cases of dengue disease in said dengue endemic area are infections by a dengue virus of serotype 3 or 4.

A human subject according to the present invention (to which a vaccine composition of the present invention is administered) is advantageously resident in a dengue endemic area in which the circulating dengue strain of serotype 2 has a genotype which is characterised by the presence of Thr and Gly at positions E-226 and E-228. Advantageously, the circulating dengue strain of serotype 2 has a genotype which is characterised by the presence of at least five of or all six of the following residues Arg, Asn, Asp, Thr, Gly and His at positions prM-16, E-83, E-203, E-226, E-228 and E-346 respectively, wherein the residues at positions E-226 and E-228 must be Thr and Gly respectively. In this context, prM-16 designates position 16 of the prM protein and E-83 designates position 83 of the E protein etc. A human subject according to the present invention (to which a vaccine composition of the present invention is administered) is preferably resident in a dengue endemic area in which the circulating serotype 2 dengue virus has a genotype as defined in this paragraph, i.e. at least 50%, at least 60%, at least 70%, at least 80%, at least 90%, at least 95% or 100% of the cases of dengue disease of serotype 2 in said dengue endemic area are caused by dengue virus of serotype 2 having said genotype. Dengue disease caused by a dengue virus of serotype 2, as referred to herein, is preferably dengue disease caused by a dengue virus of serotype 2 having a genotype as defined in this paragraph.

A human subject according to the present invention (to which a vaccine composition of the present invention is administered) is advantageously resident in a dengue endemic area in which the circulating dengue strain of serotype 2 does not have an Asian-1 genotype. Dengue viruses of serotype 2 can be sub-divided into several genotypes, which are referred to as: American, Asian/American, Asian-1, Asian-2, Cosmopolitan and Sylvatic (Twiddy S S et al. (2002) Phylogenetic relationships and differential selection pressures among genotypes of dengue-2 virus. Virology; 298(1): 63-72). Thus, a human subject according to the present invention (to which a vaccine composition of the present invention is administered) is advantageously resident in a dengue endemic area in which the circulating dengue strain of serotype 2 has an American, Asian/American, Asian-2, Cosmopolitan or Sylvatic genotype. More preferably, a human subject according to the present invention (to which a vaccine composition of the present invention is administered) is advantageously resident in a dengue endemic area in which the circulating dengue strain of serotype 2 has an American, Asian/American, or Cosmopolitan genotype. A human subject according to the present invention (to which a vaccine composition of the present invention is administered) is preferably resident in a dengue endemic area in which the circulating serotype 2 dengue virus has a genotype as defined in this paragraph, i.e. at least 50%, at least 60%, at least 70%, at least 80%, at least 90%, at least 95% or 100% of the cases of dengue disease of serotype 2 in said dengue endemic area are caused by dengue virus of serotype 2 having an American, Asian/American, Asian-2, Cosmopolitan or Sylvatic genotype, preferably an American, Asian/American or Cosmopolitan genotype. Dengue disease caused by a dengue virus of serotype 2, as referred to herein, is preferably dengue disease caused by a dengue virus of serotype 2 having an American, Asian/American, Asian-2, Cosmopolitan or Sylvatic genotype. More preferably, dengue disease caused by a dengue virus of serotype 2, as referred to herein, is preferably dengue disease caused by a dengue virus of serotype 2 having an American, Asian/American, or Cosmopolitan genotype. The genotype of a particular dengue-2 virus strain is determined by sequence alignment and phylogenetic tree analysis. Briefly, reference sequences (which are selected nucleotide sequences encoding the E proteins of a representative strain of each genotype as described in Twiddy et al.) are aligned with the nucleotide sequences encoding the E proteins of the serotype-2 strains to be genotyped. Then a phylogenetic tree is calculated and a genotype is assigned to each unknown serotype-2 strain according to their respective clustering with the reference-genotype sequences. Phylogenetic trees are calculated according to the maximum likelihood method using FastTree 2 software (Price M N et al., FastTree 2—approximately maximum-likelihood trees for large alignments, PLoS One. 2010; 5(3): e9490) and the Whelan and Goldman model of amino acid evolution (Whelan S, Goldman N. A general empirical model of protein evolution derived from multiple protein families using a maximum-likelihood approach. Mol. Biol. Evol. 2001; 18(5): 691-699).

The dengue disease according to the present invention may be virologically-confirmed dengue disease.

Preferably, a composition according to the present invention, i.e. a composition for use in a method according to the present invention, reduces the incidence or likelihood of dengue disease.

Preferably, a composition according to the present invention, i.e. a composition for use in a method according to the present invention, results in the prevention of (i.e. is for use in the prevention of) dengue disease caused by dengue virus serotypes 1, 2, 3 and 4 in individuals 9 through 60 years of age living in endemic areas. In this context, an individual is understood to be a human subject.

Preferably, a composition according to the present invention, i.e. a composition for use in a method according to the present invention, results in the prevention of (i.e. is for use in the prevention of) dengue disease caused by dengue virus serotypes 1, 2, 3 and 4 in individuals 12 through 60 years of age living in endemic areas. In this context, an individual is understood to be a human subject.

The exact quantity of a live attenuated dengue virus or a live attenuated chimeric dengue virus of the present invention to be administered may vary according to the age and the weight of the subject being vaccinated, the frequency of administration as well as the other ingredients in the composition. Generally, the quantity of a live attenuated dengue virus (e.g. VDV1 or VDV2) comprised in a dose of a vaccine composition of the present invention lies within a range of from about $10^3$ to about $10^6$ $CCID_{50}$, for example within a range of from about $5\times10^3$ to about $5\times10^5$, for example about $10^4$ $CCID_{50}$. The quantity of a chimeric dengue virus (such as a chimeric YF/dengue virus or a Chimerivax® (CYD) virus) comprised in a vaccine composition of the present invention lies within a range of about $10^5$ $CCID_{50}$ to about $10^6$ $CCID_{50}$. The quantity of a live attenuated dengue virus or live attenuated chimeric dengue virus of each of serotypes 1 to 4 comprised in a tetravalent dosage form or bivalent dosage forms according to the present invention is preferably equal. Advantageously, a vaccine composition according to the present invention comprises an effective amount of a dengue antigen as defined herein.

A vaccine composition of the present invention may be administered to a human subject as a single tetravalent dosage form, i.e. a single dosage form comprising all four serotypes of dengue antigen as defined herein. Alternatively, a vaccine composition of the present invention may be administered to a human subject as two bivalent dosage forms, i.e. one bivalent dosage form containing two serotypes of dengue antigen and a second bivalent dosage form containing the remaining two serotypes of dengue antigen. Preferably, said bivalent dosage forms are simultaneously administered to said human subject at anatomically separate sites. The term "simultaneously", as defined herein, means within 24 hours, preferably within 3 hours, preferably within 10 minutes. The term "anatomically separate sites", as defined herein, means sites on the body that are drained by different lymph nodes, e.g. the deltoid regions of each arm. Preferably, a vaccine composition according to the present invention is administered to a subject as a single tetravalent dosage form.

A vaccine composition according to the present invention may further comprise a pharmaceutically acceptable carrier or excipient. A pharmaceutically acceptable carrier or excipient according to the present invention means any solvent or dispersing medium etc., commonly used in the formulation of pharmaceuticals and vaccines to enhance stability, sterility and deliverability of the active agent and which does not produce any secondary reaction, for example an allergic reaction, in humans. The excipient is selected on the basis of the pharmaceutical form chosen, the method and the route of administration. Appropriate excipients, and requirements in relation to pharmaceutical formulation, are described in "Remington's Pharmaceutical Sciences" (19th Edition, A. R. Gennaro, Ed., Mack Publishing Co., Easton, Pa. (1995)). Particular examples of pharmaceutically acceptable excipients include water, phosphate-buffered saline (PBS) solutions and a 0.3% glycine solution. A vaccine composition according to the present invention may advantageously comprise 0.4% saline.

A vaccine composition for use in a method of the present invention may optionally contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, human serum albumin, essential amino acids, nonessential amino acids, L-arginine hydrochlorate, saccharose, D-trehalose dehydrate, sorbitol, tris (hydroxymethyl) aminomethane and/or urea. In addition, the vaccine composition may optionally comprise pharmaceutically acceptable additives including, for example, diluents, binders, stabilizers, and preservatives. Preferred stabilizers are described in WO 2010/003670.

As appreciated by skilled artisans, a vaccine composition of the present invention is suitably formulated to be compatible with the intended route of administration. Examples of suitable routes of administration include for instance intramuscular, transcutaneous, subcutaneous, intranasal, oral or intradermal. Advantageously, the route of administration is subcutaneous.

The vaccine compositions of the present invention may be administered using conventional hypodermic syringes or safety syringes such as those commercially available from Becton Dickinson Corporation (Franklin Lakes, N.J., USA) or jet injectors. For intradermal administration, conventional hypodermic syringes may be employed using the Mantoux technique or specialized intradermal delivery devices such as the BD Soluvia™ microinjection system (Becton Dickinson Corporation, Franklin Lakes, N.J., USA), may be used.

The volume of a vaccine composition of the present invention administered will depend on the method of administration. In the case of subcutaneous injections, the volume is generally between 0.1 and 1.0 ml, preferably approximately 0.5 ml.

According to one embodiment, the invention also provides a kit comprising a vaccine composition of the invention and instructions for the use of said vaccine composition in a method of protecting a human subject against dengue disease. The kit may comprise said vaccine composition in the form of a single tetravalent dosage form or said kit may comprise said vaccine composition in the form of two bivalent dosage forms. The kit can comprise at least one dose (typically in a syringe) of any vaccine composition contemplated herein. According to one embodiment the kit may comprises a multi-dose formulation of any vaccine composition as described herein. The kit further comprises a leaflet mentioning the use of the said vaccine composition for the prevention of dengue disease or the use of the said vaccine for the prophylaxis of dengue disease. The leaflet may further mention the vaccination regimen and the human subject population to be vaccinated.

The efficacy of a vaccine composition of the present invention in reducing the likelihood or severity of dengue disease may be measured in a number of ways. For instance the efficacy of a vaccine composition of the present invention in reducing the likelihood or severity of dengue disease may be calculated by measuring after the administration of at least one dose of said vaccine composition (e.g. after administration of one, two or three doses of said vaccine composition):

(i) the number of cases of dengue disease caused by dengue virus of any serotype;
(ii) the number of severe dengue cases caused by dengue virus of any serotype;
(iii) the number of DHF cases caused by dengue virus of any serotype; and/or
(iv) the number of hospitalized cases of dengue disease caused by dengue virus of any serotype;

in a group of subjects that has received said vaccine composition and comparing those measurements with the equivalent measurements from a control group of subjects that has not received said vaccine composition, wherein the subjects in both said groups are resident in a dengue endemic region. A statistically conclusive reduction in any one or more of (i) to (iv) in the vaccinated group of subjects when compared with the unvaccinated control group of subjects is indicative of the efficacy of a vaccine composition according to the present invention.

The efficacy of a vaccine composition according to the present invention in reducing the severity or likelihood of dengue disease may also be calculated by measuring after the administration of at least one dose of said vaccine composition (e.g. after administration of one, two or three doses of said vaccine composition):

(i) the mean duration and/or intensity of fever;

(iii) the mean value for plasma leakage as defined by a change in haematocrit;

(iii) the mean value for thrombocytopenia (platelet count); and/or (iv) the mean value of the level of liver enzymes including alanine aminotransferase (ALT) and aspartate aminotransferase (AST);

in a group of subjects that has received said vaccine composition and who have developed virologically-confirmed dengue disease and comparing those measurements with the equivalent measurements from a control group of subjects that has not received said vaccine composition and who have developed virologically-confirmed dengue disease. A statistically significant reduction in any one or more of (i) to (iv) in the vaccinated group of subjects who have developed virologically-confirmed dengue disease when compared with the control group of subjects who have developed virologically-confirmed dengue disease is indicative of the efficacy of a vaccine composition according to the present invention in reducing the severity or likelihood of dengue disease.

Typically the efficacy of the method of protection of the invention against a dengue disease, as measured e.g. by the method described in example 1 (Vaccine Efficacy (VE)= $100*(1-ID_{CYD}/ID_{Control})$, where ID is the incidence density (i.e., the number of human subjects with virologically-confirmed dengue divided by the number of person-years at risk) in each group), is at least 50%, preferably at least 60%. The efficacy of the method of protection being advantageously at least 70% against dengue disease caused by serotype 3 or 4.

Alignments of the nucleic sequences disclosed herein with other nucleic acid sequences may be achieved by any of the suitable sequence alignment methods well known to a person skilled in the art. For example, sequence alignments may be carried out by hand. More conveniently, an alignment may be carried out using a specialised computer program. For example, optimal sequence alignment can be achieved and percent identity can be determined by global sequence alignment algorithms such as the Multiple Sequence Alignment (MSA) algorithms Clustal W and Clustal Omega algorithms, or the Multiple Sequence Comparison by Log-Expectation (MUSCLE) algorithm (Edgar R C, Nucl. Acids Res. (2004): 32 (5): 1792). These algorithms are available on the European Bioinformatics Institute (EBI) web site at www.ebi.ac.uk/services. Where such algorithms have user-defined parameters, the default parameters should be used.

It is understood that the various features and preferred embodiments of the present invention as disclosed herein may be combined together.

Throughout this application, various references are cited. The disclosures of these references are hereby incorporated by reference into the present disclosure.

The present invention will be further illustrated by the following examples. It should be understood however that the invention is defined by the claims, and that these examples are given only by way of illustration of the invention and do not constitute in any way a limitation thereof.

EXAMPLES

Example 1

Study of a Tetravalent CYD Vaccine in Healthy Children and Adolescents Aged 9 to 16 Years in Latin America Methods Study Design and Participants A randomized, observer-blind, placebo-controlled, multicentre Phase III efficacy trial of a tetravalent CYD vaccine (comprising the strains CYD1, CYD2, CYD3 and CYD4) against virologically-confirmed dengue disease was conducted. The trial was carried out at sites in the following dengue-endemic countries: Brazil, Colombia, Honduras, Mexico, and Puerto Rico.

20,875 subjects aged 9 to 16 years who were in good health based on medical history and physical examination were enrolled into the trial. Subjects with chronic illness that might interfere with trial conduct or completion, congenital or acquired immunodeficiency, and those receiving immunosuppressive therapy or other prohibited treatments or vaccines that might interfere with trial conduct or completion were excluded.

Participants were randomly assigned 2:1 to receive three doses of the CYD vaccine or a control product at months 0, 6 and 12. Therefore, 13,917 subjects received the CYD vaccine and 6,958 received a NaCl placebo. A subset of subjects from each country was also evaluated for immunogenicity to enable the generation of country-specific data on immunogenicity, and baseline dengue antibody levels. The immunogenicity subset included a total of 1944 subjects (1,301 in the CYD vaccine group and 643 in the control group).

Products

Each of the chimeric viruses were produced and cultured on Vero cells as described in WO 03/101397, Guy et al, Hum. Vaccines (2010) 6 (9): 696; Guy et al, Vaccine (2010) 28: 632; Guirakhoo et al, J. Virol. (2000) 74: 5477; Guirakhoo et al, J. Virol. (2001) 75 (16): 7290; Guirakhoo et al, Virol. (Jun. 20, 2002) 298: 146; and Guirakhoo et al, J. Virol. (2004) 78 (9): 4761.

The vaccine was presented as a lyophilized powder (previously stored at temperature of between 2° C. and 8° C.), which was reconstituted with 0.5 mL of solvent (0.4% NaCl) for injection. As reconstituted, each 0.5 mL dose of vaccine contained 5±1 $\log_{10}$ $CCID_{50}$ of each live, attenuated, chimeric dengue serotype 1, 2, 3, 4 virus and excipients (essential amino acids, non-essential amino acids, L-arginine chlorhydrate, saccharose, D-trehalose dehydrate, sorbitol, tris (hydroxymethyl) aminoethane and urea). The control product was 0.9% NaCl saline placebo. All products were injected subcutaneously into the deltoid region of the upper arm.

Assessments

Surveillance in the active phase of the study (DO to 13 months after dose 3, i.e. a 25 month period) was designed to maximize the detection of symptomatic, virologically-confirmed dengue in order to provide an assessment of the CYD vaccine's efficacy in preventing symptomatic dengue, regardless of severity. Twelve months of surveillance post-dose 3 was expected to result in the detection of a sufficient number of virologically-confirmed dengue cases to allow for an assessment of efficacy. The continuation of the active phase for 13 months post-dose 3 was based on this 12 month period beginning 28 days after dose 3. Following the active phase, the study comprised a four year long-term follow-up (LTFU) phase designed to develop understanding of the safety of the dengue vaccine in the longer term.

All subjects attended at least 5 scheduled visits. Subjects from the immunogenicity subset attended 7 additional visits. All subjects were regularly contacted (e.g., phone calls, SMS, home visits, and school based surveillance) with an initial minimum frequency of one contact every week.

Two blood samples were taken to confirm the dengue case in the event of acute febrile illness (i.e., temperature ≥38° C. on at least 2 consecutive days). Two consecutive febrile episodes were considered as separate episodes if the interval between these 2 episodes was >14 days. An acute febrile episode was considered to have ended once the temperature was <38° C.

The first blood sample was taken during the acute phase of the disease, as soon as possible and within 5 days of the onset of fever. Testing included dengue IgM/IgG ELISA (kit "EL1500M" from Focus Diagnostics, California, US), dengue NS1 ELISA Ag (kit: "Platelia™ Dengue NS1 Ag" from Bio-Rad, Marnes-la-Coquette, France), dengue screen (DS) RT-PCR, dengue serotype-specific RT-PCR (Simplexa™ Dengue RT-PCR from Focus Diagnostics, California, US), hematocrit, platelet count, aspartate aminotransferase (AST) and alanine transaminase (ALT). The dengue screen (DS) RT-PCR is a quantitative reverse transcription PCR carried out with primers from a gene sequence conserved among dengue viruses. Due to a virus standard included in each run, results can be expressed as a concentration of $log^{10}$ plaque forming unit (PFU)/mL. The dengue serotype-specific RT-PCR was used on all DS RT-PCR positive or Dengue NS1 Ag ELISA positive samples for serotype identification.

The second blood sample was taken during the convalescent phase (i.e. between 7 and 14 days after the acute sample). Testing included dengue IgM/IgG ELISA, haematocrit, platelet count, AST and ALT.

If a sample was positive for the DS RT-PCR (i.e., ≥lower limit of quantification [LLOQ]) and/or the NS1 assay was positive and/or the Simplexa dengue RT-PCR assay was positive, this was classified as a virologically-confirmed dengue infection.

Information on all serious adverse events (SAE) was collected and assessed throughout the surveillance period.

Dengue neutralizing antibody levels were measured by plaque reduction neutralization test (PRNT) using the parental dengue virus strains of the CYD vaccine constructs. The assay's quantitation limit is 10 (1/dil). The PRNT assay data was used for the immunogenicity endpoint.

Statistical Analysis

The primary objective was to assess the efficacy of CYD Dengue Vaccine after 3 vaccinations at 0, 6 and 12 months in preventing symptomatic virologically-confirmed dengue cases, regardless of the severity, due to any of the four serotypes in children and adolescents aged 9 to 16 years at the time of inclusion. The Per Protocol (PP) population included all participants who received 3 doses according to the protocol. The confirmed dengue cases in the PP population were cases that took place more than 28 days after the third dose (i.e., at month 13) until month 25.

The efficacy analyses included the assessment of vaccine efficacy against virologically confirmed dengue that took place at any time from DO to month 25 (i.e. the entire active phase) in the intention-to-treat (ITT) population. The ITT population included all participants who received at least 1 dose.

The statistical methodology was based on the use of the two-sided 95% confidence interval (CI) of the VE. The CI was calculated using the exact method described by Breslow & Day (Breslow N E, Day N E. Statistical methods in cancer research. Volume II: The design and analysis of cohort studies. Oxford (UK): Oxford University Press; 1987). The efficacy of the CYD vaccine was considered as significant if the lower bound of the 95% CI was greater than 25%. Vaccine efficacy was assessed taking into account the number of cases (i.e. participants with one or more episodes of virologically-confirmed dengue) and the cumulative person-time at risk to calculate the incidence density in each group (Tran N H, Luong C Q, Vu T Q H, et al. Safety and immunogenicity of recombinant, live attenuated tetravalent dengue vaccine (CYD-TDV) in healthy Vietnamese adults and children. J Vaccines Vaccin 2012; 3: 1-7).

As a secondary objective, VE was evaluated on virologically-confirmed cases, according to each dengue serotype.

Similar calculations were performed to assess VE estimates according to severity (WHO criteria and clinical criteria) for virologically-confirmed dengue cases. Virologically-confirmed hospitalized dengue cases due to each or any serotype occurring during the active phase were also investigated. The serological profile of suspected dengue cases is based on IgG and IgM ELISA results.

Analyses for safety and immunogenicity endpoints are descriptive using 95% confidence intervals (CI). Immunogenicity was assessed using geometric mean of titre (GMT) for each serotype (parental strains) before the first injection and 28 days after the second and the third injections, and 1 year after the third injection.

Results

Of the 20,875 subjects enrolled, 95.5% completed the full immunisation schedule. There was a 4.5% drop out rate during the 2 years of active dengue surveillance and 9.7% of subjects were excluded from the PP population. Vaccine and control groups were comparable for age and gender and nearly 80% of those sampled at baseline were positive for antibodies against dengue.

Efficacy

During the study, 397 dengue cases (397 episodes) of virologically-confirmed dengue were identified in the PP population (completed 3 doses). All these episodes occurred more than 28 days after the third dose and before the end of the active phase and are included in the primary analysis. 176 cases occurred during 11793 person-years at risk in the vaccine group, while 221 cases occurred during 5809 person-years at risk in the control group. The corresponding vaccine efficacy was 60.8% (95% CI: 52.0-68.0).

The overall vaccine efficacy in the ITT group (received at least 1 dose) during the active phase was 64.7% (95% CI: 58.7-69.8). In the ITT group, 277 cases occurred during 26883 person-years at risk in the vaccine group, while 385 cases occurred during 13204 person-years at risk in the control group. Hence, the vaccine efficacy was consistent in the ITT and PP populations.

Post-hoc analyses revealed differing efficacy by serotype. Efficacy against each of the four serotypes after at least one dose (ITT population) was in the range 50.2%-80.9%. Efficacy against each of the four serotypes after three doses (PP population) was in the range 42.3%-77.7%. Hence, the trial has demonstrated statistically significant efficacy against any serotype (VE=60.8%) as well as conclusive efficacy against each serotype individually, including serotype 2.

These findings are set out in detail for the PP and ITT groups in Tables 1 and 2 below.

TABLE 1

Vaccine efficacy against symptomatic virologically-confirmed dengue post-dose 3 due to each serotype (PP population).

| | CYD Dengue Vaccine Group (N = 13288) | | | | Control Group (N = 6643) | | | | Vaccine Efficacy | |
|---|---|---|---|---|---|---|---|---|---|---|
| | Cases | Person-years at risk | Density incidence (95% CI) | n Episodes | Cases | Person-years at risk | Density incidence (95% CI) | n Episodes | % | (95% CI) |
| Serotype 1 | 66 | 12478 | 0.5 (0.4; 0.7) | 66 | 66 | 6196 | 1.1 (0.8; 1.4) | 66 | 50.3 | (29.1; 65.2) |
| Serotype 2 | 58 | 12495 | 0.5 (0.4; 0.6) | 58 | 50 | 6219 | 0.8 (0.6; 1.1) | 50 | 42.3 | (14.0; 61.1) |
| Serotype 3 | 43 | 12514 | 0.3 (0.2; 0.5) | 43 | 82 | 6213 | 1.3 (1.1; 1.6) | 82 | 74.0 | (61.9; 82.4) |
| Serotype 4 | 18 | 12522 | 0.1 (0.1; 0.2) | 18 | 40 | 6206 | 0.6 (0.5; 0.9) | 40 | 77.7 | (60.2; 88.0) |
| Unserotyped | 6 | 12540 | <0.1 (0.0; 0.1) | 6 | 3 | 6268 | <0.1 (0.0; 0.1) | 3 | 0.0 | (−517.8; 78.6) |

Cases: number of subjects with at least one symptomatic virologically-confirmed dengue episode from 28 days post-injection 3 to the end of the active phase.
Density incidence: data are cases per 100 person-years at risk.
n Episodes: number of symptomatic virologically-confirmed dengue episodes in the considered period.
Dengue virus serotypes are determined by Simplexa RT-PCR.
Subjects with a virologically-confirmed dengue of the studied serotype between V01 and 28 days after injection 3 are excluded from the corresponding serotype-specific analysis.

TABLE 2

Vaccine efficacy against symptomatic virologically-confirmed dengue during the active phase due to each serotype (ITT population).

| | CYD Dengue Vaccine Group (n = 13914) | | | | Control Group (n = 6940) | | | | Vaccine Efficacy | |
|---|---|---|---|---|---|---|---|---|---|---|
| | Cases | Person-years at risk | Density incidence (95% CI) | n Episodes | Cases | Person-years at risk | Density incidence (95% CI) | n Episodes | % | (95% CI) |
| Serotype 1 | 99 | 27016 | 0.4 (0.3; 0.4) | 99 | 109 | 13434 | 0.8 (0.7; 1.0) | 109 | 54.8 | (40.2; 65.9) |
| Serotype 2 | 84 | 27035 | 0.3 (0.2; 0.4) | 84 | 84 | 13461 | 0.6 (0.5; 0.8) | 84 | 50.2 | (31.8; 63.6) |
| Serotype 3 | 55 | 27060 | 0.2 (0.2; 0.3) | 55 | 106 | 13459 | 0.8 (0.6; 1.0) | 106 | 74.2 | (63.9; 81.7) |
| Serotype 4 | 32 | 27063 | 0.1 (0.1; 0.2) | 32 | 83 | 13442 | 0.6 (0.5; 0.8) | 83 | 80.9 | (70.9; 87.7) |
| Unserotyped | 15 | 27079 | <0.1 (0.0; 0.1) | 16 | 14 | 13514 | 0.1 (0.1; 0.2) | 14 | 46.5 | (−19.6; 75.9) |

Cases: number of subjects with at least one symptomatic virologically-confirmed dengue episode from D 0 to the end of the active phase.
Density incidence: data are cases per 100 person-years at risk.
n Episodes: number of symptomatic virologically-confirmed dengue episodes in the considered period.
Dengue virus serotypes are determined by Simplexa RT-PCR Vaccine Efficacy in Respect of Severe Dengue and Reduction in Hospitalisation Due to Dengue During the Active Phase In those subjects within the ITT population that acquired virologically-confirmed dengue, a 95.5% vaccine efficacy against severe dengue cases due to any serotype was observed in the vaccinated group when compared with the control group. The Investigator considered the following potential criteria for severity in all virologically-confirmed dengue cases in order to determine whether a case was considered severe: 1) Shock (pulse pressure ≤20 mmHg in a child or adolescent, or hypotension [≤90 mmHg] with tachycardia, weak pulse and poor perfusion); 2) Bleeding requiring blood transfusion; 3) Encephalopathy, i.e. unconsciousness or poor conscious state or convulsions not attributable to simple febrile convulsion or focal neurological signs. Poor conscious state or unconsciousness must be supported by a Glasgow Coma Scale (GCS) score; 4) Liver impairment (AST>1000 U/L or prothrombin time [PT] International normalized ratio [INR]>1.5); 5) Impaired kidney function (serum creatine ≥1.5 mg/dL); 6) Myocarditis, pericarditis or clinical heart failure supported by chest X-ray (CXR), echocardiography, electrocardiogram (ECG) or cardiac enzymes where these are available. The appearance of at least one of the six criteria was sufficient to result in a diagnosis of severe dengue. In addition, every effort was made to identify and document any existing chronic co-morbidity, such as uncontrolled epilepsy, chronic liver disease, existing cardiac disease or acute co-morbidity, such as acute hepatitis. All dengue cases were reviewed by an Independent Data Monitoring Committee (IDMC) in order to ensure consistence application of the term severe in the context of dengue disease.

The vaccine efficacy results against severe dengue (IDMC definition) in respect of any serotype and in respect of each serotype individually (which show efficacy particularly in respect of severe dengue caused by serotype 2) are provided in Table 3 below:

TABLE 3

Vaccine Efficacy against virologically-confirmed severe dengue (active phase, ITT population)

| | Vaccine Group Cases | Control Group Cases | VE (95% CI) |
|---|---|---|---|
| Serotype 1 | 1 | 3 | 83.4% (−106.4; 99.7) |
| Serotype 2 | 0 | 4 | 100% (24.6; 100.0) |
| Serotype 3 | 0 | 3 | 100% (−20.4; 100.0) |
| Serotype 4 | 0 | 1 | 100% (−1837.1; 100.0) |
| All Dengue Cases | 1 | 11 | 95.5% (68.8; 99.9) |

In those subjects within the ITT population that acquired virologically-confirmed dengue, a statistically significant reduction in the incidence of hospitalisation due to any serotype was observed in the vaccinated group when compared with the control group. This conclusive reduction was also observed against each serotype individually, including serotype 2. The relative risk (RR) in respect of all dengue cases after at least one dose was 0.197 (see Table 4).

TABLE 4

Hospitalised Dengue cases by serotype during the active phase (ITT)

| | Vaccine Group Cases | Control Group Cases | Relative Risk (95% CI) |
|---|---|---|---|
| Serotype 1 | 7 | 13 | 0.269 (0.09; 0.72) |
| Serotype 2 | 6 | 15 | 0.200 (0.06; 0.54) |
| Serotype 3 | 3 | 9 | 0.166 (0.03; 0.67) |
| Serotype 4 | 1 | 6 | 0.083 (0.00; 0.69) |
| All Dengue Cases | 17 | 43 | 0.197 (0.11; 0.35) |

Efficacy Estimates by Age Group During the Active Phase

The vaccine efficacy for the 9-11 year age group in the ITT population during the active phase was 61.7% (95% CI: 52.3-69.3). 150 cases and 151 episodes occurred during 12172 person-years at risk in the vaccine group, while 192 cases and 195 episodes occurred during 5967 person-years at risk in the control group.

The vaccine efficacy for the 12-16 year age group in the ITT population during the active phase was 67.6% (95% CI: 59.3-74.3). 127 cases and 129 episodes occurred during 14711 person-years at risk in the vaccine group, while 193 cases and episodes occurred during 7237 person-years at risk in the control group. Vaccine efficacy per country is shown in the following table.

TABLE 5

Vaccine Efficacy by Country (ITT population, active phase)

| Country | VE (95% CI) | % Seropositive (≥10 1/dil) | Serotype distribution of VCD episodes (% 1, 2, 3, 4)* |
|---|---|---|---|
| Brazil | 77.5% (66.5; 85.1) | 74% | 15.1, 2.5, 0, 81.5 |
| Colombia | 67.5% (58.3; 74.7) | 92% | 36.7, 20.4, 37.5, 4.7 |
| Honduras | 71.1% (57.0; 80.7) | 86% | 9.6, 27.8, 50.4, 0 |
| Mexico | 31.3% (1.3; 51.9) | 53% | 41.4, 55.6, 0, 3 |
| Puerto Rico | 57.6% (−2.5; 82.8) | 56% | 91.7, 8.3, 0, 4.2 |

*Where figures do not add up to 100, this reflects the presence of unserotyped cases.

Immunogenicity

Geometric mean titres (GMT) of neutralising antibodies against dengue serotypes 1-4 in the immunogenicity subset pre dose 1 are, respectively, 128 (95% CI: 112-145), 138 (123-156), 121 (108-136), and 43.6 (39.6-48) in the vaccine group. In the control group these values are respectively 119 (98.7-142), 115 (97.2-136), 114 (95.9-136), and 39 (33.9-44.7).

Geometric mean titres (GMT) of neutralising antibodies against dengue serotypes 1-4 in the immunogenicity subset on Day 28 after the third injection are, respectively, 395 (95% CI: 353-441), 574 (528-624), 508 (465-555), and 241 (226-258) in the vaccine group. In the control group these values are 121 (101-145), 129 (109; 152), 124 (105; 147), and 44.3 (38.6; 50.8).

Safety

Out of all the subjects in the active phase (13195 in the vaccine group and 6939 in the control group), 4.1% (95% CI: 3.7; 4.4) severe adverse events (SAEs) were reported in the vaccine group and 4.4% (4.0; 4.9) SAEs reported in the control group. There were no vaccine-related SAEs or related deaths and no increase in severe Dengue. There were no safety concerns from the SAE review of the active phase.

TABLE 6

Incidence of Virologically-Confirmed Dengue Cases due to any Serotype by Dengue Status during the active phase

| | CYD Dengue Vaccine Group | | | | Control Group | | | | | |
|---|---|---|---|---|---|---|---|---|---|---|
| | Cases | Person-years at risk | Density incidence (95% CI) | Episodes | Cases | Person-years at risk | Density incidence (95% CI) | Episodes | RR** | 95% CI |
| Positive* (Dengue immune) | 8 | 2116 | 0.4 (0.2; 0.7) | 8 | 23 | 994 | 2.3 (1.5; 3.5) | 23 | 0.163 | (0.06; 0.38) |
| Negative (Dengue naïve) | 9 | 500 | 1.8 (0.8; 3.4) | 9 | 9 | 284 | 3.2 (1.5; 5.9) | 9 | 0.568 | (0.20; 1.62) |
| All | 17 | 2620 | 0.6 (0.4; 1.0) | 17 | 32 | 1284 | 2.5 (1.7; 3.5) | 32 | 0.260 | (0.14; 0.48) |

*Positive ≥10 1/dil for at least one serotype

**Relative Risk

Discussion

The main finding from this study was that a safe, efficacious vaccine against all four serotypes of dengue virus is possible. The study showed a statistically significant vaccine efficacy against any serotype as well as showing conclusive efficacy against each serotype in both the ITT and PP populations (active phase). Furthermore, the vaccine efficacy was consistent in the ITT and PP populations.

This study has therefore demonstrated, for the first time, conclusive vaccine efficacy against serotype 2, particularly against severe dengue caused specifically by serotype 2. These results must be viewed in light of previous clinical trials which were inconclusive in respect of the efficacy of the CYD vaccine against serotype 2.

It was also demonstrated that, in those subjects that acquired virologically-confirmed dengue, a statistically significant reduction in hospitalization due to dengue was observed in the vaccinated group when compared with the control group. This reduction was seen in respect of any serotype and also in respect of each serotype individually, including serotype 2 (see Table 4).

The study also showed that a trend was observed towards higher vaccine efficacy in those patients that are dengue seropositive (i.e. dengue immune) to at least one serotype at baseline (see Table 6) and that vaccine efficacy differs by country (see Table 5). The variation according to country may be due in particular to the underlying dengue seropositivity status of the population in each country and/or the serotype of the strain(s) circulating in each country.

As can be seen from FIG. 2, no evidence of waning of vaccine efficacy was seen over a 12 month period post dose 3. Overall vaccine efficacy (against any serotype) is shown as the solid line.

The vaccine's safety profile was good, and no vaccine-related SAEs and no safety signals were identified during the review of AEs and SAEs. No enhanced disease in breakthrough infections over 2 years was observed.

In conclusion, the present study represents a major milestone in dengue vaccine development.

Example 2

Study of a Tetravalent CYD Vaccine in Healthy Children Aged 2 to 14 Years in Asia Methods A multicentre, randomised, observer-masked, placebo-controlled, Phase III trial was carried out in five countries in the Asia-Pacific region in 10,275 children aged 2-14 years old. The study design was very similar to the Latin American trial described in Example 1 in that the vaccine administered (CYD1-4), the dose and dosage schedule and the efficacy and immunogenicity analysis were all the same. Full details of the trial are provided in Capeding et al. (www.thelancet-.com; published online at dx.doi.Org/10.1016/S0140-6736(14)61060-6).

Subjects in the immunogenicity subset of the trial who were dengue immune at baseline were further analysed to determine whether they were monotypic or multitypic dengue immune (Monotypic: Ab>=10 to 1 DENV or one serotype with at least a 6 fold higher response compared to the 3 others; Multitypic: At least 2 serotypes >=10, and less than 6 fold difference between the positive serotypes).

Results

In an exploratory, post-hoc analysis, the effect of dengue baseline status (dengue naïve, monotypic dengue immune or multitypic dengue immune) on vaccine efficacy (in the immunogenicity subset) was investigated by determining the Relative Risk (RR) of virologically confirmed dengue in each sub-group. The results are shown in the table below.

TABLE 7

Distribution of dengue Cases by baseline status in the subset

| | CYD | Control | RR** | 95% CI |
|---|---|---|---|---|
| Naïve | 23 | 18 | 0.646 | (0.334, 1.270) |
| Monotypic | 13 | 19 | 0.358 | (0.162, 0.764) |
| Multitypic | 5 | 14 | 0.155 | (0.044, 0.456) |

**Relative Risk

Discussion

The data in Table 7 show that a trend towards higher vaccine efficacy is observed in subjects who are monotypic dengue immune compared to dengue naïve subjects and also in subjects who are multitypic dengue immune compared to monotypic dengue immune.

Example 3

Integrated Analysis of Data from the Clinical Trials Reported in Examples 1 and 2

In the following example, certain data from the Latin American and Asian Phase III clinical trials described in Examples 1 and 2 have been combined in order to increase the statistical power of the analysis and to provide a more global picture of the efficacy of the tetravalent CYD vaccine.

The post dose 3 vaccine efficacy (PP population) against virologically-confirmed dengue (of any severity) in respect of any serotype and in respect of each serotype for each trial and pooled across both trials is shown in the following table:

TABLE 8

Pooled data for vaccine efficacy (PP population) across Latin American and Asian trials

| | Vaccine Efficacy % (95% CI) | | | | |
|---|---|---|---|---|---|
| Trial | Any serotype | ST1 | ST2 | ST3 | ST4 |
| LatAm (Ex. 1) | 60.8<br>(52.0; 68.0)<br>(n = 397) | 50.3<br>(29.1; 65.2)<br>(n = 132) | 42.3<br>(14.0; 61.1)<br>(n = 108) | 74.0<br>(61.9; 82.4)<br>(n = 125) | 77.7<br>(60.2; 88.0)<br>(n = 58) |
| Asia (Ex. 2) | 56.5<br>(43.8; 66.4)<br>(n = 251) | 50.0<br>(24.6; 66.8)<br>(n = 101) | 35.0<br>(−9.2; 61.0)<br>(n = 67) | 78.4<br>(52.9; 90.8)<br>(n = 33) | 75.3<br>(54.5; 87.0)<br>(n = 51) |
| Pooled | 59.2<br>(52.3; 65.0)<br>(n = 647) | 50.2<br>(35.6; 61.5)<br>(n = 233) | 39.6<br>(18.7; 55.2)<br>(n = 175) | 74.9<br>(65.1; 82.0)<br>(n = 158) | 76.6<br>(65.0; 84.4)<br>(n = 109) |

The vaccine efficacy (ITT population, active phase) against virologically-confirmed dengue (of any severity) in respect of any serotype and in respect of each serotype for each trial and pooled across both trials is shown in the following table:

TABLE 9

Pooled data for vaccine efficacy (ITT population, active phase) across Latin American & Asian trials

| | Vaccine Efficacy % (95% CI) | | | | |
|---|---|---|---|---|---|
| Trial | Any serotype | ST1 | ST2 | ST3 | ST4 |
| Pooled | 60.3 (55.7; 64.5) (n = 1257) | 54.7 (45.4; 62.3) (n = 450) | 43.0 (29.4; 53.9) (n = 339) | 71.6 (63.0; 78.3) (n = 221) | 76.9 (69.5; 82.0) (n = 365) |

A similar pooled analysis of the vaccine efficacy against severe dengue (IDMC definition), DHF and hospitalised dengue cases during the active phase (any serotype) is shown in the following table. The data are shown in respect of the population who received at least one dose (i.e. the ITT population). The data in respect of the PP population were consistent.

TABLE 10

Pooled data across Latin American and Asian trials for vaccine efficacy against severe forms of dengue disease (ITT population, active phase)

| | Vaccine Efficacy % (95% CI) | | |
|---|---|---|---|
| Trial | Severe dengue | DHF | Hospitalised dengue* |
| LatAm (Ex. 1) | 95.5 (68.8; 99.9) (n = 12) | 95.0 (64.9; 99.9) (n = 11) | 80.3 (64.7; 89.5) (n = 60) |
| Asia (Ex. 2) | 70.0 (35.7; 86.6) (n = 32) | 80.0 (52.7; 92.4) (n = 28) | 67.2 (50.3; 78.6) (n = 101) |
| Pooled | 79.1 (60.0; 89.0) (n = 44) | 85.0 (68.5; 92.9) (n = 39) | 72.7 (62.3; 80.3) (n = 161) |

*= The relative risk (RR) of hospital admissions for virologically-confirmed dengue was calculated as the ratio of annual incidence in the vaccine and control groups and presented here as vaccine efficacy (1-RR).

The vaccine efficacy against severe dengue per serotype (IDMC definition) based on pooled data from both clinical trials was estimated by adding together the number of cases from both trials and comparing the numbers in the vaccine and control groups (this calculation assumes a 2 to 1 randomisation and good compliance with the trial protocol). The data are shown in the following table.

TABLE 11

Pooled data across Latin American and Asian trials for vaccine efficacy against severe dengue disease per serotype (ITT population, active phase)

| | Vaccine Group Cases | Control Group Cases | VE (95% CI) |
|---|---|---|---|
| Serotype 1 | 6 | 12 | 75% (16.0; 91.0) |
| Serotype 2 | 3 | 8 | 81.3% (21.9; 96.8) |
| Serotype 3 | 2 | 6 | 83% (24; 98) |
| Serotype 4 | 2 | 6 | 83% (24; 98) |
| All Dengue Cases | 13 | 31 | 79.1% (60.0; 89.0) |

The vaccine efficacy against hospitalised dengue per serotype based on pooled data from both clinical trials (active phase, ITT analysis) is shown in the following table.

TABLE 12

Pooled data across Latin American and Asian trials for vaccine efficacy against hospitalised dengue disease per serotype (ITT population, active phase)

| | Vaccine Group Cases | Control Group Cases | VE (95% CI) |
|---|---|---|---|
| Serotype 1 | 22 | 39 | 72.1 (82.9; 83.4) |
| Serotype 2 | 20 | 29 | 65.7 (39.3; 80.6) |
| Serotype 3 | 10 | 22 | 77.4 (52.2; 89.3) |
| Serotype 4 | 5 | 15 | 83.5 (54.5; 94.0) |
| All Dengue Cases | 57 | 104 | 73.2 (27.8; 91.0) |

The vaccine efficacy against symptomatic virologically-confirmed dengue due to any serotype for the individual and pooled trial datasets (active phase, ITT analysis) for all trial subjects aged at least 9 years old at baseline and for the same age group as a function of their baseline dengue sero-status is shown in the following table.

TABLE 13

Pooled data across Latin American and Asian trials for vaccine efficacy against dengue disease in the ≥9 years age group by serostatus (ITT population, active phase)

| | Vaccine Efficacy % (95% CI) | | |
|---|---|---|---|
| Trial | All patients ≥9 years old | Patients seropositive at baseline* ≥9 years old | Patients seronegative at baseline* ≥9 years old |
| LatAm (Ex. 1) | 64.7 (58.7; 69.8) (n = 962) | 83.7 (62.2; 93.7) (n = 31) | 43.2 (−61.6; 80.0) (n = 18) |
| Asia (Ex. 2) | 67.8 (57.7; 75.6) (n = 226) | 79.2 (47.2; 92.7) (n = 24) | 61.9 (−21.1; 88.1) (n = 15) |
| Pooled | 65.6 (60.7; 69.9) (n = 1188) | 81.9 (67.2; 90.0) (n = 55) | 52.5 (5.9; 76.1) (n = 33) |

*= Data generated from the patients in the immunogenicity subset.

As can be seen from Table 13, in the integrated analysis, the lower bound of the 95% confidence interval was above zero in sero-negative individuals aged years.

Further analyses of the pooled vaccine efficacy data in individuals aged years (all patients in this sub-population) demonstrated the following: efficacy against serotype 1 was 58.4% (47.7; 66.9); efficacy against serotype 2 was 47.1%

(31.3; 59.2); efficacy against serotype 3 was 73.6% (64.4; 80.4); efficacy against serotype 4 was 83.2% (76.2; 88.2); efficacy against hospitalized dengue was 80.8 (70.1; 87.7); efficacy against severe (IDMC-defined) dengue was 93.2 (77.3; 98.0) and efficacy against DHF was 92.9 (96.1; 97.9). In each case, the figures in brackets represent the 95% confidence intervals and the data is taken from the ITT population.

The relative risk (RR) for having >1 episode of symptomatic virologically-confirmed dengue due to any serotype for the individual and pooled trial datasets in the intention-to-treat analysis set (active phase) is shown in the following table.

TABLE 14

| | Vaccine Group Cases | Control Group Cases | RR (95% CI) |
|---|---|---|---|
| LatAm (Ex. 1) | 3 | 3 | 0.50 (0.07; 3.72) |
| Asia (Ex. 2) | 4 | 10 | 0.20 (0.05; 0.69) |
| Pooled | 7 | 13 | 0.27 (0.10; 0.66) |

The data in Table 14 show that the risk of having >1 episode of symptomatic virologically-confirmed dengue due to any serotype was lower in the vaccine group, i.e. following an initial infection during the active surveillance phases of the trials, there was a reduced risk of subsequent infections in the vaccine group compared to the control group.

Example 4

Long Term Follow Up Data

The trials described in Examples 1 and 2 have a four-year on-going, long-term follow-up (LTFU) phase to further investigate safety using the incidence of hospitalization for VCD of any severity due to any serotype. In addition, the participants in a further trial involving the vaccine described in Examples 1 and 2 (a single-centre phase IIb trial involving 4,002 participants aged 4-11 years in Thailand as described in Sabchareon et al., The Lancet, v. 380: 1559-1567 (2012), which has a similar design as the active phases of the trials described in Examples 1 and 2), also has a four-year LTFU phase to further investigate safety in the same way as the trials described in Examples 1 and 2. In each of the trials, the LTFU phase follows on immediately from the active phase, i.e. year 1 of the LTFU phase commences 25 months after the first dose of vaccine.

The long-term follow-up analyses presented here are based on data collected in the first year of the 4-year LTFU phase of the Phase 3 efficacy trials that were conducted in five Asian Pacific countries (Example 2) and five Latin American countries (Example 1) and the first two years of the 4-year LTFU phase of the Phase IIb trial in Thailand. The trials' sponsor was unblinded to treatment allocation during the LTFU phase analyses. However, all participants, their parents and the site staff remain blinded to minimize any bias during the long-term follow-up.

During the LTFU phase, all participants attend yearly visits, with regular contact (1 contact every three months, by phone, SMS or home visit) between visits. Hospitalization for acute fever is recorded during study contacts and visits, and by self-report and surveillance of identified non-study hospitals; acute blood samples are taken for virological confirmation of dengue infection. Ages refer to age at initial enrollment.

The objectives were to describe the occurrence of VCD of any severity due to any serotype requiring hospitalization and, among those hospitalized, the occurrence of severe dengue (IDMC assessment) and DHF (WHO 1997 definition) for four years after the end of the active surveillance periods.

Annual incidence rates and 95% CIs were calculated for hospitalized VCD cases (any severity, severe (IDMC), DHF (WHO)) due to any serotype and each serotype occurring annually during the LTFU phase, for each study, for all participants and for those participants aged <9 years and >9 years at inclusion. RRs were calculated as the ratio of annual incidence rates in the vaccine and control groups. The data are shown in the following table.

TABLE 15

Annual incidence rates of hospitalization (%) for virologically-confirmed dengue of any severity due to any serotype in the safety analysis sets for the Phase 3 trial in Asia (Example 2), the Phase 3 trial in Latin America (Example 1) and the Phase 2b trial in Thailand (active and LTFU phases).

| | Vaccine group | | Control Group | | Relative risk |
|---|---|---|---|---|---|
| Study, period | Cases | M | Cases | M | (95% CI) |
| Ph. 3 Asia - all participants Active surveillance phase | | | | | |
| Year 1 (Day 0 to Dose 3) | 20 | 6,848 | 26 | 3,424 | 0.39 (0.20; 0.72) |
| Year 2 (Dose 3 to Month 25) | 20 | 6,812 | 35 | 3,407 | 0.29 (0.16; 0.51) |
| Long-term follow-up phase | | | | | |
| Year 3 # (Year 1 of LTFU) | 27 | 6,778 | 13 | 3,387 | 1.04 (0.52; 2.19) |
| Cumulative results to date | | | | | |
| Day 0 to Year 3 | 67 | 6,813 | 73* | 3,406 | 0.46 (0.32; 0.65) |
| Ph. 3 Asia - participants <9 years Active surveillance phase | | | | | |
| Year 1 (Day 0 to Dose 3) | 13 | 3,533 | 18 | 1,767 | 0.36 (0.16; 0.78) |
| Year 2 (Dose 3 to Month 25) | 17 | 3,508 | 16 | 1,754 | 0.53 (0.25; 1.12) |

TABLE 15-continued

Annual incidence rates of hospitalization (%) for virologically-confirmed dengue of any severity due to any serotype in the safety analysis sets for the Phase 3 trial in Asia (Example 2), the Phase 3 trial in Latin America (Example 1) and the Phase 2b trial in Thailand (active and LTFU phases).

| | Vaccine group | | Control Group | | Relative risk |
|---|---|---|---|---|---|
| Study, period | Cases | M | Cases | M | (95% CI) |
| Long-term follow-up phase | | | | | |
| Year 3 (Year 1 of LTFU) | 19 | 3,493 | 6 | 1,741 | 1.58 (0.61; 4.83) |
| Cumulative results to date | | | | | |
| Day 0 to Year 3 | 49 | 3,511 | 40 | 1,754 | 0.61 (0.39; 0.95) |
| Ph. 3 Asia - participants ≥9 years | | | | | |
| Active surveillance phase | | | | | |
| Year 1 (Day 0 to Dose 3) | 7 | 3,315 | 8 | 1,657 | 0.44 (0.14; 1.38) |
| Year 2 (Dose 3 to Month 25) | 3 | 3,304 | 19 | 1,653 | 0.08 (0.01; 0.27) |
| Long-term follow-up phase | | | | | |
| Year 3 (Year 1 of LTFU) | 8 | 3,285 | 7 | 1,646 | 0.57 (0.18; 1.86) |
| Cumulative results to date | | | | | |
| Day 0 to Year 3 | 18 | 3,301 | 33* | 1,652 | 0.27 (0.14; 0.50) |
| Ph. 3 LatAm - all participants (all aged ≥9 years) | | | | | |
| Active surveillance phase | | | | | |
| Year 1 (Day 0 to Dose 3) | 5 | 13,915 | 15 | 6,939 | 0.17 (0.05; 0.48) |
| Year 2 (Dose 3 to Month 25) | 12 | 13,522 | 28 | 6,749 | 0.21 (0.10; 0.43) |
| Long-term follow-up phase | | | | | |
| Year 3 # (Year 1 of LTFU) | 16 | 13,268 | 15 | 6,630 | 0.53 (0.25; 1.16) |
| Cumulative results to date | | | | | |
| Day 0 to Year 3 | 33 | 13,568 | 58 | 6,773 | 0.28 (0.18; 0.44) |
| Ph. 2b Thai - all participants | | | | | |
| Active surveillance phase | | | | | |
| Year 1 (Day 0 to Dose 3) | 8 | 2,666 | 7 | 1,331 | 0.57 (0.18; 1.85) |
| Year 2 (Dose 3 to Month 25) | 24 | 2,576 | 23 | 1,292 | 0.52 (0.28; 0.97) |
| Long-term follow-up phase | | | | | |
| Year 1 (equivalent to Year 3) # | 22 | 2,131 | 11 | 1,072 | 1.01 (0.47; 2.30) |
| Year 2 (equivalent to Year 4) # | 16 | 2,131 | 17 | 1,072 | 0.47 (0.22; 1.00) |
| Cumulative results up to Year 3 | | | | | |
| Day 0 to Year 3 | 54 | 2,458 | 41 | 1,232 | 0.66 (0.43; 1.02) |
| Ph. 2b Thai - participants <9 years | | | | | |
| Active surveillance phase | | | | | |
| Year 1 (Day 0 to Dose 3) | 5 | 1,634 | 5 | 809 | 0.50 (0.11; 2.15) |
| Year 2 (Dose 3 to Month 25) | 21 | 1,572 | 14 | 783 | 0.75 (0.36; 1.59) |
| Long-term follow-up phase | | | | | |
| Year 1 (equivalent to Year 3) | 19 | 1,338 | 6 | 665 | 1.57 (0.60; 4.80) |
| Year 2 (equivalent to Year 4) | 13 | 1,338 | 12 | 665 | 0.54 (0.23; 1.29) |
| Cumulative results up to Year 3 | | | | | |
| Day 0 to Year 3 | 45 | 1,515 | 25 | 753 | 0.89 (0.54; 1.52) |
| Ph. 2b Thai - participants ≥9 years | | | | | |
| Active surveillance phase | | | | | |
| Year 1 (Day 0 to Dose 3) | 3 | 1,032 | 2 | 522 | 0.76 (0.09; 9.08) |
| Year 2 (Dose 3 to Month 25) | 3 | 1,004 | 9 | 509 | 0.17 (0.03; 0.68) |

TABLE 15-continued

Annual incidence rates of hospitalization (%) for virologically-confirmed dengue of any severity due to any serotype in the safety analysis sets for the Phase 3 trial in Asia (Example 2), the Phase 3 trial in Latin America (Example 1) and the Phase 2b trial in Thailand (active and LTFU phases).

| | Vaccine group | | Control Group | | Relative risk |
|---|---|---|---|---|---|
| Study, period | Cases | M | Cases | M | (95% CI) |
| Long-term follow-up phase | | | | | |
| Year 1 (equivalent to Year 3) | 3 | 793 | 5 | 407 | 0.31 (0.05; 1.58) |
| Year 2 (equivalent to Year 4) | 3 | 793 | 5 | 407 | 0.31 (0.09; 0.93) |
| Cumulative results up to Year 3 | | | | | |
| Day 0 to Year 3 | 9 | 943 | 16 | 479 | 0.29 (0.11; 0.69) |

M: number of participants present at the beginning of each year or mean of number of participants followed during the years included in the considered period.
*One participant had two episodes, in Year 1 and Year 3.
Overall number of each serotype (ST) identified (vaccine vs. control - randomization 2:1) in the first year of long-term follow-up phase: Ph. 3 - Asia: ST1: 11 vs. 1; ST2: 3 vs. 0; ST3: 13 vs. 7, ST4: 0 vs. 5; Ph. 3 - LatAm: ST1: 5 vs. 5; ST2: 8 vs. 11; ST3: 3 vs. 0, ST4: 0 vs. 0; Ph. 2b - Year 1: ST1: 5 vs. 5; ST2: 17 vs. 4; ST3: 1 vs. 1, ST4: 0 vs. 0; Ph, 2b - Year 2, ST1: 4 vs. 3; ST2: 4 vs. 6; ST3: 6 vs. 3, ST4: 2 vs. 4.

The pooled RR for the first year of LTFU across all three studies was 0.84 (95% CI: 0.56; 1.24). The majority of cases were serotype 1 or serotype 2; serotype 4 was the least frequent. In the Phase 3 Asian trial, analyses by pre-defined age groups showed a clear trend for higher RR for this outcome in younger children, although the number of cases was low (subjects aged 2-5 years: RR=7.45, 95% CI: 1.15; 313.80). This observation led to age-specific analyses in the Phase 2b Thai trial that showed an RR of 2.44 (95% CI: 0.27; 115.34) in those aged 4-5 years for the first year of follow-up. In the second year of LTFU in the Phase 2b Thai trial, the RR was 0.81 for those aged 4-5 years but the upper bound of the 95% CI remained >1 (95% CI: 0.16; 5.24). Further analyses in the Phase 3 Latin American trial, that enrolled participants aged 9-16 years, showed no trend between age groups for those aged 9-11 years and 12-16 years. The observations in lower-aged groups and in CYD15 led to ad hoc analyses, on two subgroups aged <9 years and ≥9 years in all three studies.

In the first year of LTFU in the two Asian studies, RRs for participants <9 years were similar with a pooled estimated RR of 1.58 (95% CI: 0.83; 3.02), suggesting an overall trend to an increased risk in the vaccine group, although the lower bound of the 95% CI was <1. RRs for those aged ≥9 years were 0.57 (95% CI: 0.18; 1.86) in the Phase 3 Asian trial and 0.31 (95% CI: 0.05; 1.58) in in the Phase 2bThai trial, similar to that for the Phase 3 Latin American trial where all the participants were aged ≥9 years (RR=0.53, 95% CI: 0.25; 1.16). For the Phase 3 Asian trial, an exploratory analysis showed that in those aged 9-11 years, the RR was 1.01 (95% CI: 0.22; 6.23) compared with 0.25 (95% CI: 0.02; 1.74) in those aged 12-14 years. This trend was not observed in CYD15 and CYD57. Pooled RR for participants aged ≥9 years across all three studies was 0.50 (95% CI: 0. 29; 0.86).

In the second year of LTFU in the Phase 2b Thai trial, the RR for participants aged ≥9 years (0.31, 95% CI: 0.09; 0.93) was similar to that in the first year (0.31, 95% CI: 0.05; 1.58), while the RR for the participants <9 years (in the second year of LTFU) had decreased (0.54, 95% CI: 0.23; 1.29).

The IDMC classified 12 and 8 hospitalized VCD cases as severe in Year 1 of the LTFU of the Phase 3 Asian and Latin American trials respectively (11/27 and 1/13 in the Asian trial and 3/16 and 5/15 in the Latin American trial, in the vaccine and control groups, respectively). In the Asian trial, 8/19 and 0/6 cases in the vaccine and placebo groups, respectively, in participants aged <9 years vs. 3/8 and 1/7 in those aged ≥9 years were classified as severe by the IDMC. The three Asian trial vaccine group cases occurred in participants aged 9-11 years at enrolment. All cases were classified as grade I/II DHF.

The IDMC classified 4/22 cases of hospitalized VCD in Year 1 of the LTFU of the Thai Phase 2b trial as severe, all in the vaccine group. In Year 2 of the LTFU of the Thai Phase 2b trial, they classified 1/16 and 2/17 cases as severe in the vaccine and control groups, respectively. All severe cases occurred in participants aged <9 years. Two cases in the vaccine group in year 1 were classified as grade III DHF and both had clinical shock while the others were grade I/II.

The length of hospitalization and duration of fever and clinical symptoms were similar for those hospitalized during the active surveillance and the LTFU phases in all three trials (data not shown). No clinically important differences in the frequencies of various signs and symptoms presented by the hospitalized participants were observed between the active surveillance and LTFU phases in any of the studies, or between vaccine and control groups, suggesting no changes in the clinical picture of hospitalized cases during the LTFU.

Discussion

During the first year of the LTFU phase in the Phase 3 Asian trial, the RR shifted to 1.0 for hospitalized VCD despite the low number of cases observed. Further analyses showed that this shift was due to a higher RR in younger children, particularly in those aged ≤5 years, compared with that in participants aged ≥9 years. The combined analysis of the first year of LTFU in the three trials showed a lower risk of hospitalized VCD in participants aged ≥9 years in the vaccine group, compared with those in the control group. However, variability of the RRs for Years 1 (1.01, 95% CI: 0.47; 2.30) and 2 (0.47, 95% CI: 0.22; 1.00) in the Thai Phase 2b trial suggests that results from the first years of LTFU in CYD14 and CYD15 should be interpreted with caution.

TABLE 16

| Sequence Listing | |
|---|---|
| SEQ ID NO. | Sequence |
| 1 | prM-E nucleotide sequence of the serotype 1 vaccinal strain which is derived from the PUO 359 (TVP-1140) wild type strain |
| 2 | prM-E nucleotide sequence of the serotype 2 vaccinal strain which is derived from the PUO 218 wild type strain |
| 3 | prM-E nucleotide sequence of the serotype 3 vaccinal strain which is derived from the PaH881/88 wild type strain |
| 4 | prM-E nucleotide sequence of the serotype 4 vaccinal strain which is derived from the 1228 (TVP 980) wild type strain |
| 5 | prM-E nucleotide sequence of the serotype 2 vaccinal strain derived from the MD1280 wild type strain (CYD-2V) |
| 6 | Entire nucleotide sequence of the VDV1 strain |
| 7 | Entire nucleotide sequence of the VDV2 strain |

The above listed nucleotide sequences constitute the positive strand RNA of the listed dengue viruses (i.e. the nucleotide sequence which is found in the corresponding viral particles). The equivalent DNA sequences (which may be used to manipulate and express the corresponding virus and which also form part of the disclosure of the present application), can be generated by replacing the nucleotide U with the nucleotide T. Such DNA sequences constitute the cDNA sequences of the corresponding dengue viruses.

The invention claimed is:

1. A method of protecting a dengue immune human subject against dengue disease caused by a dengue virus of serotype 2, comprising A) administering only 2 doses of an effective amount of a vaccine composition to the dengue immune human subject, wherein the doses are 6 months apart, and wherein said composition comprises:

a dengue antigen of each of serotypes 1 to 4, wherein said dengue antigens of serotypes 1 to 4 are each a live attenuated chimeric dengue virus comprising a yellow fever virus genome whose prM-E sequence has been substituted with the prM-E sequence of a dengue virus;

wherein the prM-E sequence of the dengue antigen of serotype 1 comprises SEQ ID NO: 1, the prM-E sequence of the dengue antigen of serotype 2 comprises SEQ ID NO: 2, the prM-E sequence of the dengue antigen of serotype 3 comprises SEQ ID NO: 3 and the prM-E sequence of the dengue antigen of serotype 4 comprises SEQ ID NO: 4:

wherein each dose of tetravalent vaccine comprises 5±1 $\log_{10}$ $CCID_{50}$ of each live attenuated chimeric dengue virus;

wherein the route of administration is subcutaneous; and wherein said dengue immune human subject is aged between 2 and 60 years old; and B) protecting the dengue immune human subject against dengue disease caused by a dengue virus of serotype 2.

2. The method of claim 1, wherein said dengue disease is severe dengue disease.

3. The method of claim 1, wherein said method results in a reduction in the incidence or likelihood of hospitalization due to said dengue disease.

4. The method of claim 1, wherein said method also protects said human subject against dengue disease caused by a dengue virus of serotype 1, dengue disease caused by a dengue virus of serotype 3 and dengue disease caused by a dengue virus of serotype 4.

5. The method of claim 4, wherein said dengue disease caused by a dengue virus of serotype 1 is severe dengue disease, said dengue disease caused by a dengue virus of serotype 2 is severe dengue disease, said dengue disease caused by a dengue virus of serotype 3 is severe dengue disease and said dengue disease caused by a dengue virus of serotype 4 is severe dengue disease.

6. The method of claim 1, wherein said subject is aged between 6 and 60 years old, between 9 and 60 years old, or between 12 and 60 years old.

7. The method of claim 1, wherein said subject is at least 9 years of age.

8. The method of claim 6, wherein said subject is aged between 2 and 16 years old, between 6 and 16 years old, or between 9 and 16 years old.

9. The method of claim 1, wherein said subject is yellow fever immune.

10. The method of claim 1, wherein said subject resides in a dengue endemic area.

11. The method of claim 1, wherein said dengue disease caused by a dengue virus of serotype 2 is dengue disease caused by a dengue virus of serotype 2 having an American, Asian/American, or a Cosmopolitan genotype.

12. The method of claim 1, wherein said composition further comprises a pharmaceutically acceptable carrier or excipient.

13. The method of claim 1, wherein said method of protecting results in a statistically significant reduction in the incidence or likelihood of repeated symptomatic virologically-confirmed dengue cases.

14. The method of claim 1, wherein the human subject is protected against dengue disease caused by a dengue virus of serotype 2 after a first dose of the vaccine composition.

15. The method of claim 1, wherein the human subject is monotypic dengue immune.

16. The method of claim 1, wherein the human subject is multitypic dengue immune.

17. The method of claim 12, wherein the pharmaceutically acceptable carrier is 0.4% NaCl buffer containing excipients consisting of essential amino acids, non-essential amino acids, L-arginine chlorhydrate, saccharose, D-trehalose, dehydrate, sorbitol, tris (hydroxymethyl) aminoethane and urea.

18. The method of claim 1, wherein the vaccine composition is administered in a volume between 0.1 and 1.0 ml.

19. The method of claim 1, wherein the vaccine composition is administered in a volume of 0.5 ml.

20. The method of claim 1, wherein the dengue immune human subject is in good health based on medical history and physical examination.

21. A method of protecting a dengue immune human subject against dengue disease caused by a dengue virus of serotype 2, comprising A) administering only 2 doses of an effective amount of a vaccine composition to the dengue immune human subject, wherein the doses are 6 months apart, and wherein said composition comprises:

a dengue antigen of each of serotypes 1 to 4, wherein said dengue antigens of serotypes 1 to 4 are each a live attenuated chimeric dengue virus comprising a yellow fever virus genome whose prM-E sequence has been substituted with the prM-E sequence of a dengue virus;

wherein the prM-E sequence of the dengue antigen of serotype 1 comprises SEQ ID NO: 1, the prM-E sequence of the dengue antigen of serotype 2 comprises SEQ ID NO: 2, the prM-E sequence of the dengue antigen of serotype 3 comprises SEQ ID NO: 3 and the prM-E sequence of the dengue antigen of serotype 4 comprises SEQ ID NO: 4;

wherein each dose of tetravalent vaccine comprises 5±1 $\log_{10}$ $CCID_{50}$ of each live attenuated chimeric dengue virus;

wherein the route of administration is subcutaneous;

wherein the vaccine composition further comprises a pharmaceutically acceptable carrier which is 0.4% NaCl buffer containing excipients consisting of essential amino acids, non-essential amino acids, L-arginine chlorhydrate, saccharose, D-trehalose, dehydrate, sorbitol, tris (hydroxymethyl) aminoethane and urea;

wherein the vaccine composition is administered in a volume between 0.1 and 1.0 ml;

wherein said subject is aged between 2 and 60 years old;

wherein the dengue immune human subject is in good health based on medical history and physical examination; and wherein said subject resides in a dengue endemic area; and B) protecting the dengue immune human subject against dengue disease caused by a dengue virus of serotype 2.

22. The method of claim 21, wherein the human subject is monotypic dengue immune.

23. The method of claim 21, wherein the human subject is multitypic dengue immune.

24. The method of claim 21, wherein the human subject is aged between 6 and 60 years old.

25. The method of claim 21, wherein the human subject is aged between 9 and 16 years old.

26. The method of claim 21, wherein the prM-E sequence of the dengue antigen of serotype 2 comprises SEQ ID NO: 2.

27. The method of claim 21, wherein the prM-E sequence of the dengue antigen of serotype 2 comprises SEQ ID NO: 2.

* * * * *

UNITED STATES PATENT AND TRADEMARK OFFICE

CERTIFICATE OF CORRECTION

PATENT NO. : 10,946,087 B2
APPLICATION NO. : 15/507952
DATED : March 16, 2021
INVENTOR(S) : Nadia Tornieporth et al.

It is certified that error appears in the above-identified patent and that said Letters Patent is hereby corrected as shown below:

In the Claims

In Claim 1, at Column 67, Line 56, "SEQ ID NO:2, the prM-E" should read --SEQ ID NO:2 or SEQ ID NO:5, the prM-E--;

In Claim 21, at Column 70, Line 4, "SEQ ID NO:2, the prM-E" should read --SEQ ID NO:2 or SEQ ID NO:5, the prM-E--;

In Claim 26, at Column 70, Line 36, "claim 21" should read --claim 1--.

Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*